United States Patent
Fox et al.

(10) Patent No.: US 11,447,786 B2
(45) Date of Patent: Sep. 20, 2022

(54) SYSTEMS AND METHODS FOR CELLULAR REPROGRAMMING OF A PLANT CELL

(71) Applicant: PIONEER HI-BRED INTERNATIONAL, INC., Johnston, IA (US)

(72) Inventors: Tim Fox, Des Moines, IA (US); William James Gordon-Kamm, Urbandale, IA (US); Rachel Carol Huegel, Ankeny, IA (US); Keith S Lowe, Johnston, IA (US); Jon Aaron Tucker Reinders, Clive, IA (US); Huaxun Ye, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 38 days.

(21) Appl. No.: 16/755,432

(22) PCT Filed: Oct. 12, 2018

(86) PCT No.: PCT/US2018/055561
§ 371 (c)(1),
(2) Date: Apr. 10, 2020

(87) PCT Pub. No.: WO2019/075295
PCT Pub. Date: Apr. 18, 2019

(65) Prior Publication Data
US 2020/0263189 A1     Aug. 20, 2020

Related U.S. Application Data

(60) Provisional application No. 62/572,007, filed on Oct. 13, 2017.

(51) Int. Cl.
| | | |
|---|---|---|
| C12N 15/82 | (2006.01) | |
| A01H 1/08 | (2006.01) | |
| C12N 9/22 | (2006.01) | |

(52) U.S. Cl.
CPC ............. *C12N 15/823* (2013.01); *A01H 1/08* (2013.01); *C12N 9/22* (2013.01); *C12N 2310/20* (2017.05)

(58) Field of Classification Search
None
See application file for complete search history.

(56) References Cited

U.S. PATENT DOCUMENTS

2016/0212956 A1 * 7/2016 Boutilier ................ A01N 37/28

FOREIGN PATENT DOCUMENTS

| WO | 2005/063990 A2 | 7/2005 |
|---|---|---|
| WO | 2005/075655 A2 | 8/2005 |
| WO | 2006/116876 A1 | 9/2006 |
| WO | 2016146552 A1 | 9/2016 |
| WO | 2017/017108 A1 | 2/2017 |
| WO | 2017153766 A1 | 9/2017 |

OTHER PUBLICATIONS

Kunz, C., et al.: "Assessment and Improvement of Wheat Microspore derived Embryo Induction and Regeneration", Journal of Plant Physiology, Feb. 1, 2000 (Feb. 1, 2000), vol. 156, No. 2, pp. 190-196.
Lowe, Keith, et al.: "Morphogenic Regulators Baby boom and Wuschel Improve Monocot Transformation", The Plant Cell, Sep. 10, 2016 (Sep. 10, 2016), vol. 28, No. 9, pp. 1998-2015.
International Search Report and Written Opinion for International Application PCT/US2018/055561, dated Mar. 8, 2019.
Copenhaver, et al.; "Tetrad Analysis in Higher Plants. A Budding Technology"; Plant Physiology (2000) 124:7-15.
Kunitake, et al.; "Isolation and Culture of Asparagus Microspore Protoplasts"; Japan J Breed (1993) 43:231-238.
Li, et al.; "Dissecting meiotic recombination based on tetrad analysis by single-microspore sequencing in maize"; Nature Communications (2015) 6:6648.
Murovec and Bohanec; "Haploids and Double Haploids in Plant Breeding" (2012) Plant Breeding 87-106.
Stieglitz; "Role of beta-1, 3-Glucanase in Postmeiotic Microspore Release"; Developmental Biology (1977) 57:87-97.

* cited by examiner

*Primary Examiner* — Elizabeth F McElwain

(57) ABSTRACT

Plant cell fate and development is altered by treating cells with cellular reprogramming factors. Embryogenesis inducing morphogenic developmental genes are used as cellular reprogramming factors, specifically comprising polypeptides or polynucleotides encoding gene products for generating doubled haploids or haploid plants from gametes. Maize microspores treated by contacting the isolated cells with an exogenous purified, recombinant embryogenesis inducing morphogenic developmental gene polypeptide results in embryogenesis. The gametes of a maize plant develop into embryoids when transformed with a genetic construct including regulatory elements and structural genes capable of acting in a cascading fashion to alter cellular fate of plant cells. Developmental morphogenic proteins expressed from a genetic construct are used for ex situ treatment methods and for in planta cellular reprogramming.

5 Claims, 14 Drawing Sheets
Specification includes a Sequence Listing.

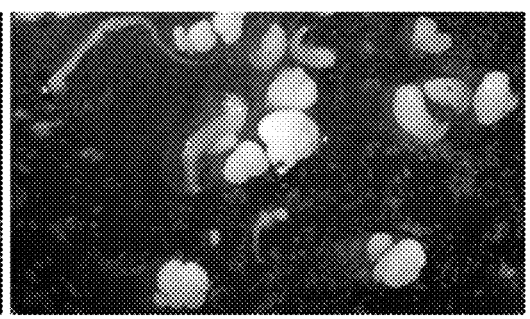
FIG. 1A      FIG. 1B
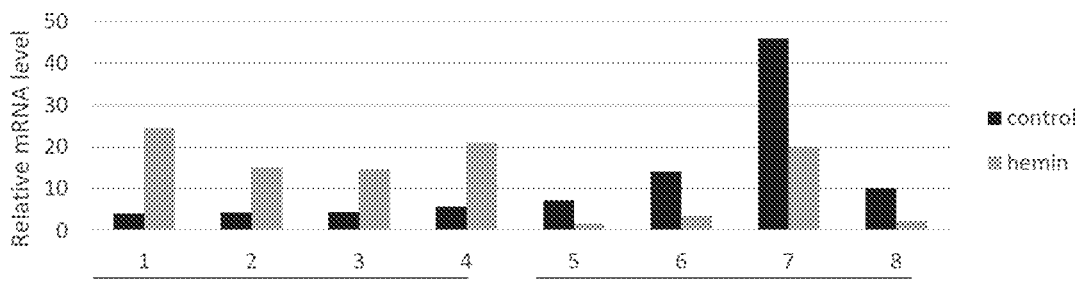
FIG. 1C
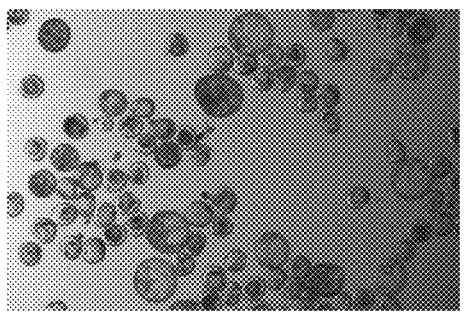
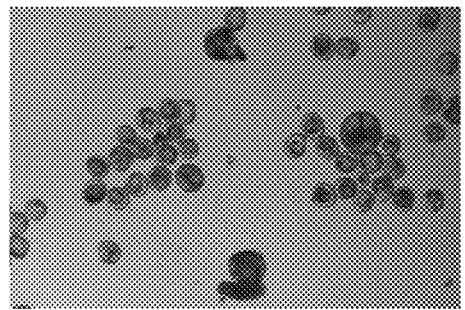
FIG. 1D      FIG. 1E
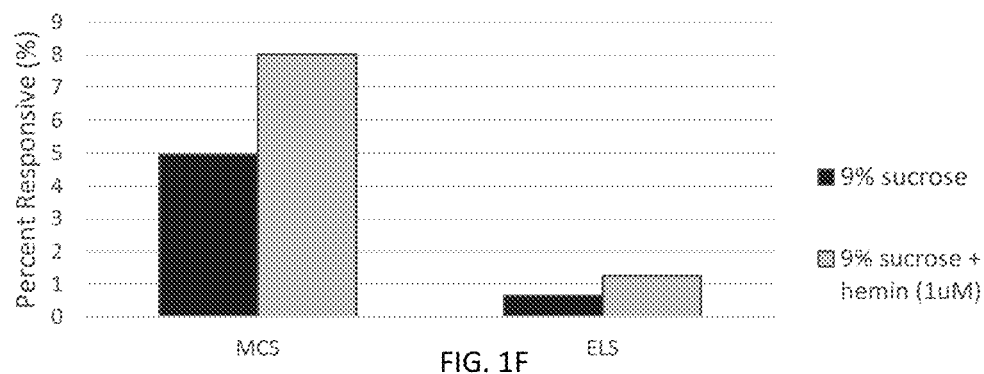
FIG. 1F

US 11,447,786 B2

SYSTEMS AND METHODS FOR CELLULAR REPROGRAMMING OF A PLANT CELL

CROSS-REFERENCE TO RELATED APPLICATIONS

This application claims the benefit of PCT Application Serial Number PCT/US2018/055561, filed Oct. 12, 2018, which claims the benefit of U.S. Provisional Application No. 62/572,007, filed Oct. 13, 2017, both of which are hereby incorporated herein by reference in their entireties.

FIELD OF THE DISCLOSURE

The present disclosure relates to the field of plant molecular biology, more particularly to developing recombinant inbred lines.

REFERENCE TO SEQUENCE LISTING SUBMITTED ELECTRONICALLY

The official copy of the sequence listing is submitted electronically via EFS-Web as an ASCII formatted sequence listing with a file named 20200410_7488-US-PCT_SequenceListingTXT created on Apr. 10, 2020 and having a size of 98,777 bytes and is filed concurrently with the specification. The sequence listing contained in this ASCII formatted document is part of the specification and is herein incorporated by reference in its entirety.

BACKGROUND OF THE DISCLOSURE

Plant breeding programs identify new cultivars by screening numerous plants to identify individuals with desirable characteristics. Large numbers of progeny from crosses are typically grown and evaluated, ideally across multiple years and environments, to select the plants with the most desirable characteristics.

Typical breeding methods cross two parental plants and the filial 1 hybrid ($F_1$ hybrid), is the first filial generation. Hybrid vigor in a commercial $F_1$ hybrid is observed when two parental strains, (typically inbreds), from different heterotic groups are intercrossed. Hybrid vigor, the improved or increased function of any biological quality resulting after combining the genetic contributions of its parents, is important to commercial maize seed production and commercial hybrid performance improvements require continued development of new inbred parental lines.

Maize inbred line development methods use maternal (gynogenic) doubled haploid production, in which maternal haploid embryos are selected following the fertilization of the ear of a plant resultant from a first-generation cross that has been fertilized with pollen from a so-called "haploid inducer" line. Pollination of a female flower with pollen of a haploid inducer strain results in elevated levels of ovules that contain only the haploid maternal genome, as opposed to inheriting a copy of both the maternal and paternal genome, thus, creating maternal haploid embryos. Ovules within the female flower are the products of meiosis and each maternal ovule is a unique meiotically recombined haploid genome, thereby allowing immature maternal haploid embryos to be isolated and treated using in vitro tissue culture methods that include chromosome doubling treatments to rapidly enable generating maternal doubled haploid recombinant populations. Many maize maternal haploid embryos resultant from fertilizing a target plant with pollen from a maize haploid inducer line fail to regenerate into a fertile, doubled haploid plant and few, if any, in vitro tissue culture and plantlet regeneration methods propagate multiple, fertile plants from one haploid embryo. Thus, there is a need for improving methods of producing doubled haploid plants applicable to maternal gamete doubled haploids in maize.

Most maize inbreds are recalcitrant to microspore isolation, in vitro tissue culture and plantlet regeneration methods to create paternal (androgenic) gamete doubled haploids. Thus, there is a need for a method of producing doubled haploid plants applicable to paternal gamete doubled haploids in maize.

Plant breeders would thus benefit from methods of developing a population of recombinant inbred lines that do not require extensive pollination control methods or the prolonged time required for propagating self-fertilized lines into isogenic states.

SUMMARY OF THE DISCLOSURE

In an aspect, a method of generating a haploid plant embryo comprising (a) obtaining an embryogenic microspore by providing a plant microspore to modulate microspore embryogenesis in the plant microspore, an embryogenesis modulation factor selected from the group consisting of (i) an embryogenesis inducing polypeptide; or (ii) an embryogenesis inducing compound; or (iii) a combination of (i) and (ii); and (b) producing the haploid plant embryo from the embryogenic microspore is provided. In an aspect, the embryogenesis inducing polypeptide is not produced by a stably integrated recombinant DNA construct in the microspore. In an aspect, the embryogenesis inducing compound is a kinase inhibitor selected from N-[(2R)-2,3-dihydroxypropoxy]-3,4-difluoro-2-(2-fluoro-4-iodoanilino) benzamide, anthra(1,9-cd)pyrazol-6(2H)-one:4-(4-Fluorophenyl)-2-(4-methylsulfinylphenyl)-5-(4-pyridyl)1H-imidazole, or N-benzyl-2-(pyrimidin-4-ylamino)-1,3-thiazole-4-carboxamide. In an aspect, the embryogenesis inducing compound is hemin. In an aspect, the embryogenesis inducing polypeptide is selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, the embryogenesis inducing polypeptide further comprises a cell penetrating peptide (CPP). In an aspect, the embryogenesis modulation factor is present in a tissue culture media. In an aspect, method comprising co-culturing the microspore with an embryogenesis inducing suspension feeder cell culture, wherein the embryogenesis inducing suspension feeder cell culture expresses an embryogenesis inducing polypeptide or co-culturing the microspore with the embryogenesis modulation factor in the culture media. In an aspect, the embryogenesis inducing polypeptide is selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, the method further comprising culturing the haploid plant embryo. In an aspect, the method comprising contacting the haploid plant embryo with a chromosome doubling agent for a period sufficient to generate a doubled haploid plant embryo. In an aspect, the method wherein the microspore is obtained from maize, rice, sorghum, *brassica*, soybean, wheat, and cotton. In an aspect, the method wherein the embryogenesis modulation factor comprises a cell penetrating peptide.

In an aspect, a method of generating a haploid plant embryo comprising (a) providing a plant comprising an expression cassette, wherein the expression cassette comprises a tapetum cell preferred regulatory element operably linked to a polynucleotide encoding an embryogenesis inducing polypeptide; (b) crossing the plant of (a) with a wild type inbred plant to provide an $F_1$ hybrid; (c) recovering an embryogenic microspore from the $F_1$ hybrid of (b); and (d) producing the haploid plant embryo from the embryogenic microspore is provided. In an aspect, the embryogenesis inducing polypeptide is a morphogenic developmental polypeptide. In an aspect, the morphogenic developmental polypeptide is selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, the method further comprising modifying genomic DNA by a site-specific nuclease. In an aspect, the expression cassette further comprises a polynucleotide encoding a site-specific nuclease. In an aspect, the site-specific nuclease is selected from the group consisting of a zinc finger nuclease, a meganuclease, TALEN, and a CRISPR-Cas endonuclease. In an aspect, the CRISPR-Cas nuclease is Cas9 or Cpf1 nuclease. In an aspect, the modification of genomic DNA is made by a Cas endonuclease during microspore embryogenesis. In an aspect, the modification of DNA is an insertion, a deletion, or a substitution mutation. In an aspect, the Cas endonuclease is expressed from the expression cassette, the Cas endonuclease further comprising a cell penetrating peptide. In an aspect, the method further comprising providing a guide RNA expressed from the expression cassette. In an aspect, the modification of DNA is performed by providing a guide RNA and Cas endonuclease as a ribonucleoprotein complex exogenously to the embryogenic microspore. In an aspect, the plant is homozygous for the expression cassette. In an aspect, the expression cassette further comprises a signal peptide. In an aspect, the expression cassette further comprises a cell penetrating peptide (CPP). In an aspect, the method further comprising contacting the haploid plant embryo with a chromosome doubling agent for a period sufficient to generate a doubled haploid plant embryo. In an aspect, the plant is maize, rice, sorghum, brassica, soybean, wheat, or cotton. In an aspect, the method further comprising regenerating a doubled haploid plant from the doubled haploid plant embryo.

In an aspect, a method of generating a doubled haploid plant comprising (a) providing a plant comprising an expression cassette, wherein the expression cassette comprises an endosperm cell preferred regulatory element operably linked to a polynucleotide encoding an embryogenesis inducing polypeptide; (b) crossing the plant of (a) with a wild type $F_1$ hybrid; (c) recovering a haploid embryo from the cross of (b); (d) contacting the haploid embryo with a chromosome doubling agent for a period sufficient to generate a doubled haploid embryo; and (e) regenerating the doubled haploid plant from the doubled haploid embryo of (d) is provided. In an aspect, the embryogenesis inducing polypeptide is a morphogenic developmental polypeptide. In an aspect, the morphogenic developmental polypeptide is selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, the expression cassette further comprises a polynucleotide encoding a gene-editing nuclease. In an aspect, the method further comprising modifying genomic DNA by a site-specific nuclease. In an aspect, the expression cassette further comprises a polynucleotide encoding a site-specific nuclease. In an aspect, the site-specific nuclease is selected from the group consisting of a zinc finger nuclease, a meganuclease, TALEN, and a CRISPR-Cas endonuclease. In an aspect, the CRISPR-Cas nuclease is Cas9 or Cpf1 nuclease. In an aspect, the modification of genomic DNA is made by a Cas endonuclease during haploid embryo embryogenesis. In an aspect, the modification of DNA is an insertion, deletion, or a substitution mutation. In an aspect, the Cas endonuclease is expressed from the expression cassette, the Cas endonuclease further comprising a cell penetrating peptide. In an aspect, the method further comprising providing a guide RNA expressed from the expression cassette. In an aspect, the modification of DNA is performed by providing a guide RNA and Cas endonuclease as a ribonucleoprotein complex exogenously to the embryogenic haploid embryo. In an aspect, the plant is homozygous for the expression cassette. In an aspect, the expression cassette further comprises a signal peptide. In an aspect, the expression cassette further comprises a cell penetrating peptide (CPP). In an aspect, the expression cassette further comprises a polynucleotide encoding a color marker or a fluorescent marker operably linked to regulatory element. In an aspect, recovering the haploid embryo comprises screening for the presence or the absence of the color marker, the fluorescent marker, or the regulatory element. In an aspect, the screening occurs in a cell viability and cell sorting microfluidics device for automated fluorescence detection for identifying, sorting, and selecting a haploid embryo comprising the expression cassette from a haploid embryo not comprising the expression cassette.

In an aspect, an embryogenic microspore comprising an increased amount of an embryogenesis inducing polypeptide compared to a control microspore, wherein the polypeptide is not produced in the microspore is provided. In an aspect, an embryoid or embryogenic tissue produced from the embryogenic microspore is provided. In an aspect, an embryogenic microspore comprising a heterologous cellular reprogramming agent, wherein the heterologous cellular reprogramming agent is not produced in the microspore is provided. In an aspect, the cellular reprogramming agent is selected from the group consisting of (i) an embryogenesis inducing polypeptide; or (ii) an embryogenesis inducing compound; or (iii) a combination of (i) and (ii). In an aspect, the embryogenesis inducing polypeptide is selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, the embryogenesis inducing compound is hemin or a kinase inhibitor or a combination thereof. In an aspect, the embryogenic microspore is capable of producing a haploid embryo. In an aspect, the embryogenic microspore is a maize embryogenic microspore. In an aspect, the embryogenic microspore is from rice, sorghum, brassica, soybean, wheat, or cotton. In an aspect, a plant cell comprising an expression cassette, wherein the expression cassette comprises a tapetum cell preferred regulatory element operably linked to a polynucleotide encoding an embryogenesis inducing polypeptide, and wherein the embryogenesis inducing polypeptide is capable of being secreted or transported into a microspore is provided. In an aspect, the embryogenesis inducing polypeptide comprises a cell penetrating peptide. In an aspect, the embryogenesis inducing polypeptide is a morphogenic developmental polypeptide selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii). In an aspect, a plant cell comprising an expression cassette, wherein the expression cassette comprises an endosperm cell preferred regulatory element operably linked to a polynucleotide encoding an embryogenesis inducing polypeptide and wherein the embryogenesis inducing polypeptide is produced in an endosperm cell, the embryo surrounding region (ESR), the Basal Endosperm Transfer Layer (BETL) or a combination thereof and capable of being secreted or transported into an embryo cell is provided. In an aspect, a population of plant cells comprising the plant cell and the embryo cell, wherein the embryo cell comprises the secreted or transported embryogenesis inducing polypeptide is provided. In an aspect, the embryogenesis inducing polypeptide is a morphogenic developmental polypeptide selected from the group consisting of (i) a WUS/WOX homeobox polypeptide; (ii) a Babyboom (BBM) polypeptide or an Ovule Development Protein 2 (ODP2) polypeptide; (iii) a LEC1 polypeptide; (iv) a combination of (i) and (ii); and (v) a combination of (i) and (iii).

DESCRIPTION OF THE FIGURES

FIG. 1A shows a stereo microscope micrograph of pro-embryo development of ATCC40520 cells cultured for 21 days post isolation in a 9% sucrose induction medium (control).

FIG. 1B shows a stereo microscope micrograph of pro-embryo development of ATCC40520 cells cultured for 21 days post isolation in a 9% sucrose induction medium supplemented with hemin (1 µM final concentration).

FIG. 1C shows a bar graph of embryo-like structure expression response (relative mRNA level) of four (4) embryogenesis biomarker genes (1-GRMZM2G145440; 2-GRMZM2G057852; 3-GRMZM2G162184; and 4-GRMZM2G037368) and of four (4) pollen maturation biomarker genes (5-GRMZM2G177391; 6-GRMZM2G176595; 7-GRMZM2G469689; and 8-GRMZM2G126196) at a 99% confidence level ($p<0.01$) of ATCC40520 cells after 8 days in vitro tissue culture in a 9% sucrose induction medium supplemented with 1 µM hemin.

FIG. 1D shows a stereo microscope micrograph of pro-embryo development of cells derived from inbred EH microspores cultured for 21 days post isolation in a 9% sucrose induction medium (control).

FIG. 1E shows a stereo microscope micrograph of pro-embryo development of cells derived from inbred EH microspores cultured for 21 days post isolation in a 9% sucrose induction medium supplemented with hemin (1 µM final concentration).

FIG. 1F shows a bar graph of microspore developmental response representing the percent responsiveness of multicellular structures (MCS) and embryo-like structures (ELS) derived from inbred EH microspores cultured for 21 days post isolation in a 9% sucrose induction medium (control) and in a 9% sucrose induction medium supplemented with hemin (1 µM final concentration).

DETAILED DESCRIPTION

Figure 2A:
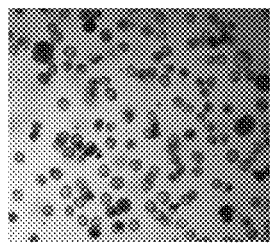
FIG. 2A shows a stereo microscope micrograph of ATCC40520 cells cultured for 7 days post isolation in a 9% sucrose induction medium without PD0325901 (N-[(2R)-2,3-dihydroxypropoxy]-3,4-difluoro-2-(2-fluoro-4-iodoanilino)benzamide) (negative control).

The disclosures herein will be described more fully hereinafter with reference to the accompanying figures, in which some, but not all possible aspects are shown. Indeed, disclosures may be embodied in many different forms and should not be construed as limited to the aspects set forth herein; rather, these aspects are provided so that this disclosure will satisfy applicable legal requirements.

Many modifications and other aspects disclosed herein will come to mind to one skilled in the art to which the disclosed methods and compositions pertain having the benefit of the teachings presented in the following descriptions and the associated figures. Therefore, it is to be understood that the disclosures are not to be limited to the specific aspects disclosed and that modifications and other aspects are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed methods and compositions belong. In this specification and in the claims which follow, reference will be made to a number of terms which shall be defined herein.

As used herein the singular forms "a", "an", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

All patents, publications and patent applications mentioned in the specification are indicative of the level of those skilled in the art to which this disclosure pertains. All patents, publications and patent applications are herein incorporated by reference in the entirety to the same extent as if each individual patent, publication or patent application was specifically and individually indicated to be incorporated by reference in its entirety.

The oxidized form of iron protoporphyrin IX, hemin, is an essential regulator of gene expression in mammalian cells, and promotes the growth of hematopoietic progenitor cells by acting as a nonprotein prosthetic group forming part of or combined with proteins including respiration cytochromes, gas sensors, P450 enzymes (CYPs), catalases, peroxidases, nitric oxide synthases (NOS), guanyl cyclases, and even transcriptional factors (Tsiftsoglou et al., (2006) Pharmacol Ther. 111:327-45). Furthermore, in mammalian cells heme has been reported to act like a signaling ligand in cell respiration and metabolism, suggesting that in addition to being a key regulator of gene expression hemin may be a useful co-factor alone or in combination with other treatments to improve stress responses, adaptive processes, and even transcription of genes to prevent cell damage.

For plant cells and maize microspores in particular, methods of improving cellular reprogramming developmental fate toward embryogenesis include the need to improve stress adaptive processes caused by cell separation and isolation techniques. Methods to inhibit proplastids within microspores from developing to amyloplast, or methods to dedifferentiate an amyloplast to a proplastid, or to promote autophagy within maize microspores are desirable.

Based on experiments in cultured cells, hemin blocks nuclear gene expression. A regulatory system of nuclear gene expressions was modulated by a plastid signal during differentiation of plastids into amyloplasts. A retrograde signaling from the plastid was blocked using heme.

The disclosure provides efficient and effective methods of producing populations of recombinant inbred lines including, but not limited to, methods of initiating embryogenesis in plant cells to enable generating doubled haploid recombinant populations. The disclosure also provides methods of enabling cellular reprogramming and embryogenic growth stimulation in non-transformed cells, and particularly in gametes or haploid cells during the development of the gametes or haploid cells The present disclosure provides methods of promoting microspore embryogenesis in a cell, tissue or organ of a plant by contacting the cell, tissue or organ with an embryogenesis modulation factor capable of reprogramming the cell, tissue or organ wherein embryogenesis is induced in the cell, tissue or organ, such as, for example, an embryogenesis inducing exogenous morphogenic developmental gene protein product and/or an embryogenesis inducing compound. Embryogenesis inducing agents useful in the methods of the disclosure include, but are not limited to protein kinase inhibitor small molecules, such as N-[(2R)-2,3-dihydroxypropoxy]-3,4-difluoro-2-(2-fluoro-4-iodoanilino)benzamide, anthra(1,9-cd)pyrazol-6(2H)-one:4-(4-Fluorophenyl)-2-(4-methylsulfinylphenyl)-5-(4-pyridyl)1H-imidazole, or N-benzyl-2-(pyrimidin-4-ylamino)-1,3-thiazole-4-carboxamide. Hemin is also useful in the methods of the disclosure for inducing embryogenesis.

Also provided in many aspects are methods of generating microspore-derived doubled haploid populations by ectopically expressing in a plant tissue or organ a fusion protein gene product of embryogenesis inducing morphogenic developmental gene and a translocation signal enabling cellular reprogramming and embryogenic growth stimulation in non-transformed cells, and particularly in gametes or haploid cells during the development of the gametes or haploid cells. In another aspect, the disclosure provides methods for generating in a plant tissue or organ microspore-derived doubled haploid population using embryogenesis inducing morphogenic developmental gene operably linked to a translocation signal and a fluorescent protein and selecting based on the presence or absence of the embryogenesis inducing morphogenic developmental gene/translocation signal/fluorescent protein fusion enabling cellular reprogramming and embryogenic growth stimulation in non-transformed cells, and particularly in gametes or haploid cells during the development of the gametes or haploid cells. The disclosure provides in many aspects methods for reprogramming microspores by co-culturing microspores with a purified protein, such as a morphogenic developmental embryogenesis inducing gene product with and without an embryogenesis inducing compound treatment. In another aspect, methods are provided for reprogramming microspores by co-culturing microspores in the presence of cells expressing a morphogenic developmental embryogenesis inducing gene product. Periods of co-cultivation (contact) with the embryogenesis inducing cellular reprogramming agents will vary depending on the recalcitrance of the microspores being treated. For example, in an aspect, microspore embryogenesis is evidenced by the presence of multicellular structures (MCS) within the sporopollenin coat and/or rupturing of the exine of the microspore and/or the presence of embryo-like structures (ELS). In an aspect, the microspores are co-cultured with the embryogenesis inducing cellular reprogramming agents until certain characteristics such as MCS and/or ELS are observed. Alternatively, in an aspect other phenotypic and/or genotypic markers are also used to determine the embryogenic state or the cellular reprogramming state. Generally, in many aspects co-cultivation for periods of less than an hour, an hour, two hours, three hours, four hours, five hours, six hours, seven hours, eight hours, nine hours, ten hours, eleven hours, twelve hours, thirteen hours, fourteen hours, fifteen hours, sixteen hours, seventeen hours, eighteen hours, nineteen hours, twenty hours, twenty one hours, twenty two hours, twenty three hours, twenty four hours, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty one days, twenty two days, twenty three days, twenty four days, twenty five days, twenty six days, twenty seven days, twenty eight days, twenty nine days, thirty days, thirty one days, thirty two days, thirty three days, thirty four days, thirty five days, thirty six days, thirty seven days, thirty eight days, thirty nine days, forty days, forty one days, forty two days, forty three days, forty four days, forty five days, forty six days, forty seven days, forty eight days, forty nine days, fifty days, fifty one days, fifty two days, fifty three days, fifty four days, fifty five days, fifty six days, fifty seven days, fifty eight days, fifty nine days, or sixty days or longer are sufficient for the cultured microspores to form MCS and/or ELS. Incubation or culturing period for inducing embryogenesis is optimized based on the type and the concentration of the embryogenesis inducing agent based on the guidance provided in this disclosure. The present disclosure also provides in many aspects methods of generating microspore-derived doubled haploid populations, using the methods described above to promote microspore embryogenesis from a tissue or organ of a filial plant resultant from a genetic cross of two different strains, such as a first generation $F_1$ hybrid or alternatively in later filial generations or back-cross generations, in a hemizygous transgenic condition.

The present disclosure also provides in many aspects methods to promote microspore embryogenesis from a tissue or organ of a first generation $F_1$ hybrid derived from transforming an $F_1$ embryo per se into said $F_1$ hybrid regenerated directly in a hemizygous transgenic condition for the purpose of generating a microspore-derived doubled haploid population. In a further aspect, the generated and/or treated microspores and/or microspore-derived cells are brought into contact with a chromosome doubling agent to promote diploidization of the microspore-derived embryoids. A further aspect of the disclosure provides methods for clonal propagation of plantlets derived from cells of a maternal haploid embryo produced by ectopic expression in a plant tissue or organ of a morphological developmental gene with or without a translocation signal. Also provided are in many aspects methods for clonal propagation of multiple gene edited plantlets derived from cells of a maternal haploid embryo produced by ectopic expression in a plant tissue or organ of a morphological developmental gene with or without a translocation signal fused to a gene product of a nuclease gene with or without a translocation signal.

The disclosure also provides in maternally-derived haploid embryo cells in many aspects methods of promoting embryogenesis in endosperm cells and gene editing using a transformed haploid inducer line expressing an embryogenesis inducing gene product of a morphological developmental gene with or without a translocation signal and a nuclease gene with or without a fertilization translocation signal. In a further aspect, the treated maternal haploids embryos and/or embryo-derived cells are brought into contact with a chromosome doubling agent to promote diploidization and regeneration of the maternally-derived somatic embryos.

As used herein, "reprogram" or "reprogramming" or "reprogrammed" is a process of reverting or sensitizing mature, specialized cells into induced pluripotent stem cells or into cells in an embryonic/embryogenic state capable of being further developed into an embryo or embryo-like structure. In a population of cells that are being "reprogrammed" not all cells are expected to be "reprogrammed" to the same extent or at the same embryonic state. A mixture or mosaic nature of cells at various states of reprogramming is generally expected. Methods and compositions provided herein are expected to increase the ratio or percent of cells that are reprogrammed and in a desired embryogenic state compared to cells that have not been exposed to the methods and compositions provided herein. Reprogramming also refers to the re-establishment of germ cell development. Reprogramming can occur when an embryogenesis inducing polypeptide and/or a small molecule compound is contacted with plant cells rendering the plant cells embryogenic. In many aspects, the methods of the disclosure contact a haploid plant cell with an embryogenesis inducing agent such as for example, a polypeptide and/or a small molecule compound to reprogram cell fate and cause the cell to become embryogenic. Alternatively, in many aspects a polynucleotide encoding an embryogenesis inducing polypeptide may be introduced and expressed in a plant cell wherein the embryogenesis inducing polypeptide impacts surrounding/adjacent cells thereby rendering the cells embryogenic. The cells may be reprogrammed in planta or ex situ. Morphogenic (morphological) developmental genes and their embryogenesis inducing polypeptide products are useful in the disclosed methods. As used herein, the term "morphogenic developmental gene" or "morphological developmental gene" means a gene involved in plant embryogenesis, cellular reprogramming, metabolism, organ development, stem cell development, cell growth stimulation, organogenesis, regeneration, somatic embryogenesis initiation, accelerated somatic embryo maturation, initiation and/or development of the apical meristem, initiation and/or development of shoot meristem, initiation and/or development of shoots, or a combination thereof. Morphogenic developmental genes when ectopically expressed stimulate formation of a somatically-derived structure that can produce a plant. Ectopic expression of the morphogenic developmental gene stimulates the de novo formation of a somatic embryo or an organogenic structure, such as a shoot meristem, that can produce a plant. This stimulated de novo formation occurs either in the cell in which the morphogenic developmental gene is expressed, or in a neighboring cell. A morphogenic developmental gene can be a transcription factor that regulates expression of other genes, or a gene that influences hormone levels in a plant tissue, both of which can stimulate morphogenic changes. A morphogenic developmental gene may be stably incorporated into the genome of a plant or it may be transiently expressed. Embryogenesis inducing morphogenic developmental genes include, but are not limited to WUS/WOX genes (WUS1, WUS2, WUS3, WOX2A, WOX4, WOX5, or WOX9) see U.S. Pat. Nos. 7,268,271, 7,309,813, 7,348,468, 7,256,322, 7,994,391. 8,383,891, 8,581,037, and 9,029,641 and United States Patent Application Publications 20170121722, 20110258741, 20100100981, 20040166563, and 20070271628, incorporated herein by reference in their entireties; Laux et al. (1996) Development 122:87-96; and Mayer et al. (1998) Cell 95:805-815; van der iGraaff et al., 2009, Genome Biology 10:248; Dolzblasz et al., 2016, Mol. Plant 19:1028-39. Modulation of WUS/WOX is expected to modulate plant and/or plant tissue phenotype including plant embryogenesis, cellular reprogramming, metabolism, organ development, stem cell development, cell growth stimulation, organogenesis, regeneration, somatic embryogenesis initiation, accelerated somatic embryo maturation, initiation and/or development of the apical meristem, initiation and/or development of shoot meristem, initiation and/or development of shoots, or a combination thereof. Also of interest in this regard would be a MYB118 gene (see U.S. Pat. No. 7,148,402), MYB115 gene (see Wang et al. (2008) Cell Research 224-235), a BABYBOOM gene (BBM; see Boutilier et al. (2002) Plant Cell 14:1737-1749), an OVULE DEVELOPMENT PROTEIN 2 (ODP2) gene (see US20110010795, US20090328252, and US20050257289 incorporated herein by reference in their entireties, or a CLAVATA gene (see, for example, U.S. Pat. No. 7,179,963).

Other embryogenesis inducing morphogenic developmental genes suitable for the present disclosure include, but are not limited to, LEC1 (Lotan et al., 1998, Cell 93:1195-1205), LEC2 (Stone et al., 2008, PNAS 105:3151-3156; Belide et al., 2013, Plant Cell Tiss. Organ Cult 113:543-553, and U.S. Pat. No. 8,865,971, incorporated herein by reference in its entirety), KN1/STM (Sinha et al., 1993. Genes Dev 7:787-795), the IPT gene from *Agrobacterium* (Ebinuma and Komamine, 2001, In vitro Cell. Dev Biol—Plant 37:103-113), MONOPTEROS-DELTA (Ckurshumova et al., 2014, New Phytol. 204:556-566), the *Agrobacterium* AV-6b gene (Wabiko and Minemura 1996, Plant Physiol. 112:939-951), the combination of the *Agrobacterium* IAA-h and IAA-m genes (Endo et al., 2002, Plant Cell Rep., 20:923-928), the *Arabidopsis* SERK gene (Hecht et al., 2001, Plant Physiol. 127:803-816), the Arabiopsis AGL15 gene (Harding et al., 2003, Plant Physiol. 133:653-663).

As used herein, the term "transcription factor" means a protein that controls the rate of transcription of specific genes by binding to the DNA sequence of the promoter and either up-regulating or down-regulating expression. Examples of transcription factors, which may also serve as embryogenesis inducing morphogenic developmental genes, include members of the AP2/EREBP family (including the BBM (ODP2), plethora and ainteguenta sub-families, CAAT-box binding proteins such as LEC1 and HAP3, and members of the MYB, bHLH, NAC, MADS, bZIP, RKD (US Patent Application Publication No. 2013/0180010), and WRKY families.

The present disclosure in an aspect also includes plants obtained by any of the disclosed methods or compositions herein. In many aspects, the present disclosure also includes seeds from a plant obtained by any of the disclosed methods or compositions herein. As used herein, the term "plant" refers to whole plants, plant organs (e.g., leaves, stems, roots, etc.), plant tissues, plant cells, plant parts, seeds, propagules, embryos and progeny of the same. As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. Plant cells include, without limitation, cells from seeds, suspension cultures, explants, immature embryos, embryos, zygotic embryos, somatic embryos, embryogenic callus, meristem, somatic meristems, organogenic callus, protoplasts, meristematic regions, embryos derived from mature ear-derived seed, leaf bases, leaves from mature plants, leaf tips, immature inflorescences, tassel, immature ear, silks, cotyledons, immature cotyledons, embryonic axes, meristematic regions, callus tissue, cells from leaves, cells from stems, cells from roots, cells from shoots, callus tissue, leaves, roots, shoots, gametophytes, sporophytes, pollen and microspores. Plant cells can be differentiated or undifferentiated (e.g. callus, undifferentiated callus, immature and mature embryos, immature zygotic embryo, immature cotyledon, embryonic axis, suspension culture cells, protoplasts, leaf, leaf cells, root cells, phloem cells and pollen). Plant parts include differentiated and undifferentiated tissues including, but not limited to, roots, stems, shoots, leaves, pollen, seeds, tumor tissue and various forms of cells in culture (e. g., single cells, protoplasts, embryos, and callus tissue). The plant tissue may be in a plant or in a plant organ, tissue, or cell culture. Grain is intended to mean the mature seed produced by commercial growers for purposes other than growing or reproducing the species. Progeny, variants and mutants of the regenerated plants are also included within the scope of the disclosure, provided these progeny, variants and mutants are made using the methods and compositions disclosed herein and/or comprise the introduced polynucleotides.

As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of a heterologous nucleic acid including those transgenics initially so altered as well as those created by sexual crosses or asexual propagation from the initial transgenic. A transgenic plant is defined as a mature, fertile plant that contains a transgene.

A transgenic "event" is produced by transformation of plant cells with a heterologous DNA construct, including a nucleic acid expression cassette that comprises a gene of interest, the regeneration of a population of plants resulting from the insertion of the transferred gene into the genome of the plant and selection of a plant characterized by insertion into a particular genome location. An event is characterized phenotypically by the expression of the inserted gene. At the genetic level, an event is part of the genetic makeup of a plant. The term "event" also refers to progeny produced by a sexual cross between the transformant and another plant wherein the progeny include the heterologous DNA.

The compositions and methods of the present disclosure are applicable to a broad range of plant species, including dicotyledonous plants and monocotyledonous plants. Representative examples of plants that can be treated in accordance with the methods disclosed herein include, but are not limited to, wheat, cotton, sunflower, safflower, tobacco, *Arabidopsis*, barley, oats, rice, maize, triticale, sorghum, rye, millet, flax, sugarcane, banana, cassava, common bean, cowpea, tomato, potato, beet, grape, *Eucalyptus*, wheat grasses, turf grasses, alfalfa, clover, soybean, peanuts, citrus, papaya, *Setaria* sp, cacao, cucumber, apple, *Capsicum*, bamboo, melon, ornamentals including commercial garden and flower bulb species, fruit trees, vegetable species, *Brassica* species, as well as interspecies hybrids. In a preferred embodiment, the compositions and methods of the disclosure are applied to maize plants.

The methods of the disclosure involve introducing a polypeptide, polynucleotide (i.e., DNA or RNA), or nucleotide construct (i.e., DNA or RNA) into a plant. As used herein, "introducing" means presenting to the plant the polynucleotide, polypeptide, or nucleotide construct in such a manner that the polynucleotide, polypeptide, or nucleotide construct gains access to the interior of a cell of the plant.

The methods of the disclosure do not depend on a particular method for introducing the polynucleotide, polypeptide, or nucleotide construct into a plant, only that the polynucleotide, polypeptide, or nucleotide construct gains access to the interior of at least one cell of the plant. Methods for introducing polynucleotides, polypeptides, or nucleotide constructs into plants are known in the art including, but not limited to, stable transformation methods, transient transformation methods and virus-mediated methods.

As used herein, a "stable transformation" is a transformation in which the polynucleotide or nucleotide construct introduced into a plant integrates into the genome of the plant and is capable of being inherited by the progeny thereof. "Transient transformation" means that a polynucleotide or nucleotide construct is introduced into the plant and does not integrate into the genome of the plant or a polypeptide is introduced into a plant. In addition, "transient", in certain embodiments may represent the presence of an embryogenesis inducing agent in a cell where such an agent has been exogenously applied or secreted into from a neighboring cell or being produced from an extrachromosomal location (e.g., plasmid or another independently replicating origin), or not produced by a stably integrated recombinant DNA construct within the same cell.

As used herein, "contacting", "comes in contact with" or "in contact with" are used to mean "direct contact" or "indirect contact" and means that the cells are place in a condition where the cells can come into contact with any of the embryogenesis inducing substances disclosed herein including, but not limited to, an embryogenesis inducing morphogenic developmental gene, a small molecule or a doubling agent. Such substance is allowed to be present in an environment where the cells survive (for example, medium or expressed in the cell or an adjacent cell) and can act on the cells. For example, the medium comprising a doubling agent may have direct contact with the haploid cell or the medium comprising the doubling agent may be separated from the haploid cell by filter paper, plant tissues, or other cells thus the doubling agent is transferred through the filter paper or cells to the haploid cell.

The methods provided herein rely upon the use of bacteria-mediated and/or biolistic-mediated gene transfer to produce regenerable plant cells. Bacterial strains useful in the methods of the disclosure include, but are not limited to, a disarmed *Agrobacteria*, an *Ochrobactrum* bacteria or a *Rhizobiaceae* bacteria. Standard protocols for particle bombardment (Finer and McMullen, 1991, In Vitro Cell Dev. Biol.—Plant 27:175-182), *Agrobacterium*-mediated transformation (Jia et al., 2015, Int J. Mol. Sci. 16:18552-18543; US2017/0121722 incorporated herein by reference in its entirety), or Ochrobactrum-mediated transformation (US2018/0216123 incorporated herein by reference in its entirety) can be used with the methods and compositions of the disclosure. Numerous methods for introducing heterologous genes into plants are known and can be used to insert a polynucleotide into a plant host, including biological and physical plant transformation protocols. See, e.g., Miki et al., "Procedure for Introducing Foreign DNA into Plants," in Methods in Plant Molecular Biology and Biotechnology, Glick and Thompson, eds., CRC Press, Inc., Boca Raton, pp. 67-88 (1993). The methods chosen vary with the host plant and include chemical transfection methods such as calcium phosphate, microorganism-mediated gene transfer such as *Agrobacterium* (Horsch, et al., (1985) Science 227:1229-31), electroporation, micro-injection and biolistic bombardment. Expression cassettes and vectors and in vitro culture methods for plant cell or tissue transformation and regeneration of transgenic plants are known and available. See, e.g., Gruber, et al., "Vectors for Plant Transformation," in Methods in Plant Molecular Biology and Biotechnology, supra, pp. 89-119.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) Biotechniques 4:320-334), electroporation (Riggs, et al., (1986) Proc. Natl. Acad. Sci. USA 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) Biotechnology 6:923-926) and Lec1 transformation (WO 00/28058). See also, Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) *Bio/Technology* 6:923-926 (soybean); Finer and McMullen, (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783 and 5,324,646; Klein, et al., (1988) Plant Physiol. 91:440-444 (maize); Fromm, et al., (1990) Biotechnology 8:833-839 (maize); Hooykaas-Van Slogteren, et al., (1984) *Nature* (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford, (1995) Annals of Botany 75:407-413 (rice); Ishida, et al., (1996) *Nature Biotechnology* 14:745-750 (maize via *Agrobacterium tumefaciens*), all of which are herein incorporated by reference in their entirety. Methods and compositions for rapid plant transformation are also found in U.S. 2017/0121722, herein incorporated in its entirety by reference. Vectors useful in plant transformation are found in U.S. patent application Ser. No. 15/765,521, herein incorporated by reference in its entirety.

Methods for harvesting tassels, including sterilization methods, as well as tassel pretreatments, for example, temperature pretreatments, are known in the art and will vary depending on the intended tassel use. Specifically, prior to selecting tassels for microspore culture, microspores must be staged to an appropriate stage typically, between the uninucleate to binucleate stage. Typically, for tassels with anthers and microspores at the appropriate stage, the tassels were detached and each tassel is individually wrapped in for example, aluminum foil.

Isolation of microspores typically occurs after a tassel pretreatment in a reduced temperature environment to improve the androgenic response. A commonly used technique is to place foil wrapped tassels at 10° C. for between 1 to 21 days. Additionally, preculture of anthers in a mannitol solution, for example 0.3M liquid mannitol plus 50 mg/L ascorbic acid, can be practiced (U.S. Pat. Nos. 5,322, 789 and 5,445,961 incorporated herein by reference in their entireties).

Prior to use, tassels can be surface-sterilized in a 40% Clorox (8.25% Sodium Hypochlorite diluted v/v) solution plus two drops of Tween 80 for approximately fifteen minutes, with gentle agitation on a reciprocal shaker. The tassels are then rinsed three or more times in sterile water at room temperature and placed in a large petri dish and typically left uncovered for 1-1.5 hours under aseptic conditions to allow any excess water to evaporate. Another method known in the art includes placing spikelets detached from the tassel into permeable baskets that are then submerged in a 40% Clorox (8.25% Sodium Hypochlorite diluted v/v) solution plus two drops of Tween 80 for fifteen minutes followed by rinsing as described above. The spikelets are placed in a large petri dish and typically left uncovered for 1-1.5 hours to allow excess water to evaporate prior to microspore isolation.

A variety of isolation procedures for maize anthers and spikelets are known in the art, including, but not limited to, glass rod maceration methods (Pescitelli, et al., (1990) Plant Cell Rep. 8:628-31), blending methods, razor blade tissue cutting methods (see U.S. Pat. No. 5,445,961 incorporated herein by reference in its entirety), tissue homogenizer methods (Gaillard, et al., (1991) Plant Cell Rep. 10:55-8), and tissue grinder methods (Mandaron et al., (1990) Theor Appl Genet 80: 134-138.

Following isolation of microspores from the surrounding somatic tissue, the microspores are typically immediately after separating the microspores from any anther debris placed into a fresh isolation medium. Numerous media compositions are known in the art. A common method of separating microspores from anther debris is to pass a blended microspore anther debris slurry from the isolation procedure through a sieve (Pescitelli (1989) Plant Cell Rep. 7:673-6, Gaillard, et al., (1991), and U.S. Pat. No. 5,445,961 incorporated herein by reference in its entirety). Alternatively, the microspore anther debris slurry is passed through several layers of cheesecloth or a mesh filter (Coumans, (1989) Plant Cell Rep. 7:618-21). Further separation can be performed using a discontinuous density centrifugation method or additional filtration methods, including but not limited, to methods using a sucrose or Percoll gradient (Coumans, (1989), Pescitelli et al., (1990)). Alternatively, selection of cells captured at the 20-30% interface of a Percoll gradient ranging from 20-50% after centrifugation at 225 g for 3 min can be further separated using a final, high sucrose (0.44M) centrifugation method (Gaillard, et al., (1991)). Further variations to separation methods are known in the art (Vergne et al., (1991) In: Negrutiu I. (ed) BioMethods. Birkhauser, Basel, Boston, Bedinger and Edgerton, (1990) Plant Physiol. 92:474-9, Gaillard, et al., (1991)) and can be optimized as needed.

Specific media used during isolation, for example, typically consists of 6% sucrose, 50 mg/L acorbic acid, 400 mg/L proline, 0.05 mg/L biotin and 10 mg/L nicotinic acid (see Petolino and Genovesi (1994) The Maize Handbook, Freeling, M., Walbot, V. (eds) Springer-Verlag, New York). Various other media and solutions used for the culturing of maize microspores are similar to those used for other cereal tissue culture procedures and various modifications can be used (see Genovesi and Magill, (1982) Plant Cell Rep. 1:257-60, Martin and Widholm, (1996) Plant Cell Rep. 15:781-85, Magnard et al., (2000) Plant Mol Biol 44:559-74, Testillano et al., (2002) Int J Dev Biol 46:1035-47, Testillano et al., (2004) Chromosoma 112:342-9, Shariatpanahi et al., (2006) Plant Cell Rep 25:1294-9, Shim et al., (2006) Protoplasma 228:79-86, Soriano et al., (2008) Plant Cell Rep 27:805-11, Cistue et al., (2009) Plant Cell Rep 28:727-35, Jacquard et al., (2009) Planta 229:393-402, Jacquard et al., (2009) Plant Cell Rep 28:1329-39, Shim et al., (2009) Genome 52:166-74, Sanchez-Diaz et al., (2013) Plant Reprod 26: 287-96). As evidenced in the citations above, common features for maize culture media typically include the use of N6, NLN, or YP basal salt formulations with relatively high sugar concentrations (6-12%) that may have constituents including triiobenzoic acid, various phytohormones, and/or proline.

The compositions and methods of the present disclosure include producing doubled haploid plants from gametes by contacting a plant cell with a morphogenic developmental embryogenesis inducing gene protein product that can induce cellular reprogramming and activate embryogenesis within the cell. An ex situ cellular reprogramming method for androgenic induction by treating isolated microspores with a morphogenic developmental embryogenesis inducing gene protein product, such as a WUSCHEL hexahistidine-tagged protein ("WUS-HISTAG") (SEQ ID NO: 1 and SEQ ID NO: 2) is also provided. In another aspect, the present disclosure provides methods of treating isolated microspores with a translational fusion protein comprising a morphogenic developmental embryogenesis inducing gene protein product and a cell penetrating peptide, more specifically a gamma-zein cell penetrating peptide (CPP) WUSCHEL hexahistidine-tagged translational fusion protein ("WUS-HISTAG-GZCPP") (SEQ ID NO: 46 and SEQ ID NO: 47).

Also provided is an ex situ cellular reprogramming method for androgenic induction by treating a plant cell with a morphogenic developmental embryogenesis inducing gene protein product and/or an embryogenesis inducing small molecule compound, or combinations thereof, enabling improved cellular reprogramming and embryogenic growth stimulation in wild type plant cells, including, but not limited to, gametic cells.

Methods of in planta cellular reprogramming for androgenic induction are also provided by expressing a morphogenic developmental embryogenesis inducing gene protein product in a tissue-specific manner. Specifically, by expressing a morphogenic developmental embryogenesis inducing gene protein product within tapetum cells of anthers, and more specifically using the Zea mays Ms44 promoter ("ZM-Ms44 PRO"; SEQ ID NO:3) and Ms44 N-terminus secretion signal peptide ("Ms44$^{SP}$"; SEQ ID NO: 4 and SEQ ID NO: 5) fused to Zea mays WUSCHEL2 sequence ("ZM-WUS2"; SEQ ID NO: 6 and SEQ ID NO: 7) to induce cellular reprogramming and activate embryogenesis within microspores.

In planta cellular reprogramming methods are also provided by transforming a plant tissue or organ with a construct comprised of a WUSCHEL gene, a translocation signal, and linker sequence ("L3"; SEQ ID NO: 8 and SEQ ID NO: 9), which may also be fused to fluorescent protein gene, for example AC-GFP1 (SEQ ID NO: 10 and SEQ ID NO: 11), and a terminator sequence ("ZM-Ms44 TERM"; SEQ ID NO: 12) and then selecting within microspore-derived doubled haploid populations based on the presence or absence of the transgene.

The disclosure also provides translational fusion proteins comprising the WUSCHEL polypeptide (SEQ ID NO: 7) and a translocation peptide or a cellular localization signal sequence (SEQ ID NO: 13 ("WUS-virF$^{C36}$"), SEQ ID NO: 14 ("WUS-virF$^{C36}$"), SEQ ID NO: 15 ("WUS-virF$^{C127}$"), SEQ ID NO: 16 ("WUS-virF$^{C127}$"), SEQ ID NO: 17 ("WUS-GALLS (GS$^{C27}$)"), SEQ ID NO: 18 ("WUS-GALLS (GS$^{C27}$)")) to create WUSCHEL variants for use in the present methods as cellular reprogramming factors to induce embryogenesis in treated cells.

In certain aspects, the in planta cellular reprogramming methods disclosed herein also provide a construct comprised of a WUSCHEL gene and a glucocorticoid receptor (GR)-based fusion protein ("WUS-GR"; SEQ ID NO: 48 and SEQ ID NO: 49) to conditionally localize protein activity to the nucleus by external application of animal hormone analogs into the in vitro tissue culture media.

The present disclosure also uses combinations of morphogenic developmental genes and their embryogenesis inducing gene protein products, such as a WUSCHEL protein and Z. mays ODP2 (ZM-ODP2; SEQ ID NO: 19 and SEQ ID NO: 20), an AP2/ERF transcription factor, or other morphogenic developmental genes and their embryogenesis inducing gene protein products known in the art. The present disclosure includes use of a translational fusion protein comprising a N-terminal Ms44 N-terminus secretion signal peptide (ZM-Ms44$^{SP}$; SEQ ID NO: 5) with the Z. mays ODP2 polypeptide (ZM-ODP2; SEQ ID NO: 20) with a C-terminal cell penetrating peptide, including, but not limited to, the Z. mays knotted1 CPP (ZM-KNT1 CPP; SEQ ID NO: 21 and SEQ ID NO: 22), the Saccharomyces pombe TP10 CPP (SP-TP10 CPP; SEQ ID NO: 23 and SEQ ID NO: 24), the Candida albicans Zebra CPP (CA-Zebra CPP; SEQ ID NO: 25 and SEQ ID NO: 26), the PEP1 CPP (PEP1 CPP; SEQ ID NO: 27 and SEQ ID NO: 28), the HIV-1 TAT CPP (HIV-1 TAT CPP; SEQ ID NO: 29 and SEQ ID NO: 30). Any signal peptide or another moiety that is capable of transporting/transferring/secreting the embryogenesis inducing polypeptide into developing microspores or one or more of the embryo cells in a maternal tissue is suitable for use with the compositions disclosed herein.

The present disclosure provides an ex situ cellular reprogramming method for androgenic induction by treating isolated microspores with a translational fusion protein comprising an embryogenesis inducing morphogenic developmental gene protein, such as a WUSCHEL hexahistidine-tagged protein and C-terminal fusion using CPPs, including, but not limited to the CPP sequences described above. Androgenic induction can be obtained by treating isolated microspores with a translational fusion protein comprising an embryogenesis inducing morphogenic developmental protein, such as a WUSCHEL protein and C-terminal fusion of a translocation signal, such as a WUSCHEL-virF$^{C36}$ translational fusion, a WUSCHEL-virF$^{C127}$ translational fusion, or a WUSCHEL-GALLS (GS$^{C27}$) translational fusion protein.

Optionally, the ex situ methods of the present disclosure use isolated microspores co-cultured with suspension "feeder cells" expressing an embryogenesis inducing morphogenic developmental polypeptide to further promote cellular reprogramming to activate microspore embryogenesis.

Optionally, the ex situ cellular reprogramming methods of the present disclosure can be combined with and used with microspores isolated from plant tissues generated using an in planta cellular reprogramming method disclosed herein.

The present disclosure provides an in planta cellular reprogramming method for regenerating maternal haploid embryos by transforming a maize haploid inducer line to stably integrate and express a heterologous expression cassette encoding a morphological developmental polypeptide that stimulates somatic embryogenesis and also encoding a second component including genes useful for gene editing purposes. Both components may comprise fusion peptides using secretion signal peptides operably linked to a promoter expressed within the endosperm. Secretion signal peptides useful in the present disclosure include, but are not limited to the Basal Endosperm Transfer Layer 9 (BETL9) secretion signal peptide ("BETL9$^{SP}$"; SEQ ID NO: 31 and SEQ ID NO: 32) operably linked to the BETL9 promoter ("ZM-BETL9 PRO"; SEQ ID NO: 33) or the Basal Endosperm Transfer Layer9-like (BETL9-like) secretion signal peptide ("BETL9-like$^{SP}$"; SEQ ID NO: 34 and SEQ ID NO: 35) operably linked to the BETL9-like promoter ("ZM-BETL9-like PRO"; SEQ ID NO: 36). The in planta cellular reprogramming methods may optionally use a fluorescent color marker expressed within the endosperm, for example the polynucleotide encoding the Anemonia majano Cyan Fluorescent Protein (CFP) operably linked to the Zea mays FEM2 promoter ("AM-CFP-ZM-FEM2"; SEQ ID NO: 39).

Other reporter genes or selectable marker genes may also be included in the expression cassettes of the present disclosure. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) EMBO J. 2:987-992); methotrexate (Herrera Estrella, et al., (1983) Nature 303:209-213; Meijer, et al., (1991) Plant Mol. Biol. 16:807-820); hygromycin (Waldron, et al., (1985) Plant Mol. Biol. 5:103-108 and Zhijian, et al., (1995) Plant Science 108:219-227); streptomycin (Jones, et al., (1987) Mol. Gen. Genet. 210:86-91); spectinomycin (Bretagne-Sagnard, et al., (1996) Transgenic Res. 5:131-137); bleomycin (Hille, et al., (1990) Plant Mol. Biol. 7:171-176); sulfonamide (Guerineau, et al., (1990) Plant Mot. Biol. 15:127-36); bromoxynil (Stalker, et al., (1988) Science 242:419-423); glyphosate (Shaw, et al., (1986) Science 233:478-481 and U.S. patent application Ser. Nos. 10/004,357 and 10/427,692); phosphinothricin (DeBlock, et al., (1987) EMBO J. 6:2513-2518), herein incorporated by reference in their entirety.

Other genes that could serve utility in the recovery of transgenic events would include, but are not limited to, examples such as GUS (beta-glucuronidase; Jefferson, (1987) Plant Mol. Biol. Rep. 5:387), GFP (green fluorescence protein; Chalfie, et al., (1994) Science 263:802), luciferase (Riggs, et al., (1987) Nucleic Acids Res. 15(19): 8115 and Luehrsen, et al., (1992) Methods Enzymol. 216: 397-414) and the maize genes encoding for anthocyanin production (Ludwig, et al., (1990) Science 247:449), herein incorporated by reference in their entirety.

The methods of the disclosure also provide for expression of multiple morphological developmental genes in one expression cassette using a polycistronic linker ("TA-T2A"; SEQ ID NO: 40 and SEQ ID NO: 41) operably linked to a promoter and a second component including genes useful for gene editing purposes, including, but not limited to, a Streptococcus pyogenes (CRISPR) CAS9 nuclease ("SP- CAS9"; SEQ ID NO: 42 and SEQ ID NO: 43), or a Cpf1 nuclease ("AC-Cpf1"; SEQ ID NO: 44 and SEQ ID NO: 45), or other nuclease proteins, including, but not limited to, zinc finger nucleases, meganucleases, or transcription activator-like effector nucleases. The use of the first component in a transformed maize haploid inducer line for fertilizing the maternal ear of a target plant is useful for improving doubled haploid production while the second component enables improving the regeneration of gene-edited, maize doubled haploids.

The present disclosure also provides methods of contacting haploid cells with an amount of a chromosome doubling agent before, during, after, or overlapping with any portion of the isolation and embryogenesis induction process used for generating a paternal gamete (androgenic) or a maternal gamete (gynogenic) doubled haploid populations.

As used herein, the use of a cellular reprogramming agent (an embryogenesis inducing polypeptide or an embryogenesis inducing compound) or a cellular reprogramming treatment of a plant cell outside of the tissue of the organism, for example, extracted cells that have been isolated for experimentation and/or measurement done in an external environment, is referred to as an "ex situ" treatment or treatment method.

As used herein "recombinant" means a cell or vector, that has been modified by the introduction of a heterologous nucleic acid or a cell derived from a cell so modified. Thus, for example, a recombinant cell is a cell expressing a gene that is not found in identical form or location within the native (non-recombinant) cell or a cell that expresses a native gene in an expression pattern that is different from that of the native (non-recombinant) cell for example, the native gene is abnormally expressed, under expressed, has reduced expression or is not expressed at all because of deliberate human intervention. The term "recombinant" as used herein does not encompass the alteration of a cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein, the polypeptides useful in the methods of the disclosure can be further engineered with a cell penetrating peptide, herein referred to as a "CPP". CPPs useful in the present methods are a class of short peptides with a property to translocate across cell membranes and act as nanocarriers for protein delivery into plant cells. Exemplary CPP families include, but are not limited to, CPPs derived from protein transduction domains, amphipathic peptides, and synthetic cationic polypeptides, such as polylysine, polyhistidine, and polyarginine, or dendrimeric polycationic molecules. Exemplary CPPs useful in the methods of the disclosure include, but are not limited to, the peptide vascular endothelial-cadherin CPP, the transportan CPP, the monomer and dimer of HIV-1 TAT basic domain Cpp, the penetratin CPP, synthetic cationic homoarginine oligopeptide CPPs (see Eudes and Chugh. (2008) Plant Signal Behav. 3:549-550) and the gamma zein CPP (see U.S. Pat. No. 8,581,036, incorporated herein by reference in its entirety). The present disclosure provides methods of using a gamma-zein CPP morphological developmental protein translational fusion protein for use in contacting the gamma-zein linked structure with a plant cell and allowing uptake of the gamma-zein linked structure into the plant cell to alter cell fate of the plant cell.

As used herein, a "cellular reprogramming factor" or an "embryogenesis inducing agent" includes, but is not limited to, small molecules, compounds, and morphological developmental embryogenesis inducing gene products that function in cell fate reprogramming either independently or in concert, including for example, microspore embryogenesis induction. When a cell is contacted with a small molecule, it is believed that these reprogramming molecules activate expression of endogenous genes within the cell eliciting an embryogenesis response in the contacted cell. As used herein, a "cellular reprogramming treatment" is any of the treatments disclosed herein that elicits an embryogenesis response in the contacted cell.

As used herein, the use of a cellular reprogramming agent (an embryogenesis inducing polypeptide or an embryogenesis inducing compound) or a cellular reprogramming treatment of a plant cell inside of the tissue of the organism, prior to cell isolation or cell extraction for experimentation and/or measurements done in an external environment is referred to as an "in planta" treatment or treatment method.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

As used herein "promoter" is an exemplary regulatory element and generally refers to a nucleotide sequence capable of controlling the expression of a coding sequence or functional RNA. In general, a coding sequence is located 3' to a promoter sequence. The promoter sequence comprises proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different regulatory elements may direct the expression of a gene in different tissues or cell types, or at different stages of development, or in response to different environmental conditions.

A "plant promoter" is a promoter capable of initiating transcription in plant cells. Exemplary plant promoters include, but are not limited to, those that are obtained from plants, plant viruses and bacteria which comprise genes expressed in plant cells such as *Agrobacterium* or *Rhizobium*. Examples are promoters that preferentially initiate transcription in certain tissues, such as leaves, roots, seeds, fibers, xylem vessels, tracheids or sclerenchyma. Such promoters are referred to as "tissue preferred" promoters. A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters are members of the class of "non-constitutive" promoters. A "constitutive" promoter is a promoter that causes a nucleic acid fragment to be expressed in most cell types at most times under most environmental conditions and states of development or cell differentiation.

A "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) Mol. Biotechnol. 3:225-236).

As discussed above, one of skill will recognize the appropriate promoter to use to modulate paternal or maternal embryogenesis. For paternal embryogenesis, exemplary promoters include tassel-preferred promoters, anther-preferred promoters, and tapetum-preferred promoters. Known tissue-specific, tissue-preferred or stage-specific regulatory elements further include the anther-specific LAT52 (Twell, et al., (1989) Mol. Gen. Genet. 217:240-245), microspore-specific promoters such as the apg gene promoter (Twell, et al., (1993) Sex. Plant Reprod. 6:217-224) and tapetum-specific promoters such as the TA29 gene promoter (Mariani, et al., (1990) Nature 347:737; U.S. Pat. No. 6,372,967), stamen-specific promoters such as the MS26 gene promoter, MS44 gene promoter, MS45 gene promoter, the 5126 gene promoter, the BS7 gene promoter, the PG47 gene promoter (U.S. Pat. Nos. 5,412,085; 5,545,546; Zheng et al., (1993) Plant J 3(2):261-271), the SGB6 gene promoter (U.S. Pat. No. 5,470,359), G9 gene promoter (U.S. Pat. Nos. 5,8937, 850; 5,589,610), the SB200 gene promoter (WO 2002/26789), and the like. A tissue-preferred promoter active in cells of male reproductive organs is particularly useful in certain aspects of the present disclosure.

For maternal embryogenesis, exemplary promoters include seed-preferred promoters. "Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, the Cim1 (cytokinin-induced message) promoter; the cZ19B1 (maize 19 kDa zein) promoter; and the milps (myo-inositol-1-phosphate synthase) promoter (see WO 00/11177 and U.S. Pat. No. 6,225,529 incorporated herein by reference in it entirety). Other promoters useful in the methods of the disclosure include, but are not limited to, are endosperm-specific promoters, such as the Gamma-zein promoter (Boronat et al. (1986) Plant Science 47:95-102) and embryo-specific promoters, such as the Globulin-1 (Glob-1) promoter. For monocots, seed-specific promoters include, but are not limited to, the maize 15 kDa promoter, ther 22 kDa zein promoter, the 27 kDa zein promoter, the gamma-zein promoter, the waxy promoter, the shrunken 1 promoter, the shrunken 2 promoter, the globulin 1 promoter, and the like. See also WO 00/12733, disclosing seed-preferred promoters from the end1 and end2 genes. Additional seed-preferred promoters include the oleosin promoter (WO 00/0028058), the lipid transfer protein (LTP) promoter (U.S. Pat. No. 5,525,716), the Lec1 promoter, the Jip1 promoter, and the milps3 promoter (see, WO 02/42424).

As used herein, a "signal peptide" or "secretion signal peptide" sequence refers to a region of a protein interacting with a protein transport system and translocates or targets a protein for delivery to a particular destination. Examples of signal peptides or secretion signal peptides useful in the methods of the disclosure include, but are not limited to, signal-peptides targeting proteins to the extracellular matrix of the plant cell, such as the *Nicotiana plumbaginifolia* extension gene signal peptide (DeLoose, et al., (1991) Gene 99:95-100); signal peptides which cause proteins to be secreted, such as the PRIb signal peptide (Lind, et al., (1992) Plant Mol. Biol. 18:47-53) or the barley alpha amylase (BAA) signal peptide (Rahmatullah, et al., (1989) Plant Mol. Biol. 12:119).

Secretion signal peptides containing domains found in the superfamily of bifunctional inhibitor/plant lipid transfer protein/seed storage helical domain proteins that characteristically encode eight conserved cysteine residues important for secondary structure include, but are not limited to, lipid transfer proteins such as LILY-LIM2 (Q43534), Sorghum (XP_002445754), Barley (BAK05897), Rice-OSC4 (BAD09233), Rice-MEN-8 (XP_006660357) and Maize-MZm3-3 (NP_001105123) which are useful for engineering male-expressed plant-specific proteins useful in the methods of the disclosure. Secretion signal-peptides targeting proteins from the endosperm to the embryo are useful for engineering female-expressed translational fusion proteins useful in the methods of the disclosure.

As used herein, "heterologous" refers to a nucleic acid that originates from a foreign species, or, if from the same species, is substantially modified from its native form in composition and/or genomic locus by deliberate human intervention. For example, a promoter operably linked to a heterologous structural gene that is from a species different from that from which the structural gene was derived, or, if from the same species, one or both are substantially modified from their original form and/or genomic location.

In an aspect, the embryogenesis inducing morphogenic developmental genes useful in the methods of the disclosure can be provided in expression cassettes for expression in the plant of interest. The cassette can include 5' and 3' regulatory sequences operably linked to an embryogenesis inducing morphogenic developmental gene sequence disclosed herein. "Operably linked" is intended to mean a functional linkage between two or more elements. For example, an operable linkage between a polynucleotide of interest and a regulatory sequence (i.e., a promoter) is functional link that allows for expression of the polynucleotide of interest.

Operably linked elements may be contiguous or non-contiguous. When used to refer to the joining of two protein coding regions (fusion proteins), by operably linked it is intended that the coding regions are in the same reading frame. The cassette may additionally contain at least one additional gene to be co-transformed into the organism. Alternatively, the additional embryogenesis inducing morphogenic developmental gene(s) can be provided on multiple expression cassettes. Such an expression cassette is provided with a plurality of restriction sites for insertion of the embryogenesis inducing morphogenic developmental gene sequence to be under the transcriptional regulation of the regulatory regions (promoter(s)). The expression cassette may additionally contain selectable marker genes.

As used herein, a chimeric signal peptide-morphogenic developmental gene fusion can be further engineered with a translocation or a nuclear localization signal sequence on the C-terminus of the polypeptide to promote improved cellular reprogramming efficiency and embryogenesis induction. The methods of the present disclosure provide a genetic construct encoding a WUSCHEL protein fused with a polypeptide derived from bacterial virulence proteins conferring in planta translocation of secreted proteins. *Agrobacterium tumefaciens* and *Agrobacterium rhizogenes* are examples of plant pathogens that can transfer plasmid-encoded bacterial genes located on the transferred DNA (T-DNA) into plant cells in a manner dependent on the translocation of bacterial virulence (Vir) proteins. Translocations of fusions between Cre recombinase with Vir protein polypeptides, specifically VirE2 or VirF peptide sequences, directly demonstrated a role conferred by the Vir peptides for protein translocation into plant cells (Vergunst et al., (2000) Science 290: 979-82). Further, the C-terminal 27 amino acids of the *A. rhizogenes* GALLS protein was shown to have a role in protein transport and nuclear localization (Hodges et al., (2006) J. Bacteriol. 188:8222-30). The use of peptides encoding translocation or nuclear localization signals are known in the art (see U.S. Pat. No. 6,800,791 incorporated herein by reference in its entirety).

As used herein, expression cassettes useful in the methods of the disclosure may contain a polynucleotide encoding a Ms44 signal peptide-WUSCHEL fusion with a translocation or a nuclear localization signal sequence or a similar Ms44 signal peptide-ODP2 fusion with a translocation fusion peptide which can be further engineered with a cell penetrating peptide, herein referred to herein as a "CPP". CPPs useful in the present methods are a class of short peptides with a property to translocate across cell membranes and act as nanocarriers for protein delivery into plant cells. Exemplary CPP families include, but are not limited to, CPPs derived from protein transduction domains, amphipathic peptides, and synthetic cationic polypeptides, such as polylysine, polyhistidine, and polyarginine, or dendrimeric polycationic molecules. Exemplary CPPs useful in the methods of the disclosure include, but are not limited to, the peptide vascular endothelial-cadherin CPP, the transportan CPP, the monomer and dimer of HIV-1 TAT basic domain Cpp, the penetratin CPP, synthetic cationic homoarginine oligopeptide CPPs (see Eudes and Chugh. (2008) Plant Signal Behav. 3:549-550) and the gamma zein CPP (see U.S. Pat. No. 8,581,036, incorporated herein by reference in its entirety). The present disclosure provides methods of using a gamma-zein CPP morphological developmental protein translational fusion protein for use in contacting the gamma-zein linked structure with a plant cell and allowing uptake of the gamma-zein linked structure into the plant cell to alter cell fate of the plant cell. Also provided for use in the methods of the disclosure are engineered embryogenesis inducing morphogenic developmental proteins comprising a CPP fused to the ODP2 protein for use in combination with a chimeric signal peptide-WUSCHEL fusion protein. These genetic constructs are engineered to deliver and contact a microspore with an embryogenesis inducing morphogenic developmental protein comprising a CPP fused to the ODP2 protein for use in combination with the chimeric signal peptide-WUSCHEL fusion proteins operably linked to an anther-specific promoter, or more specifically a tapetum-specific promoter.

As used herein, such genetic constructs can also be engineered to deliver and contact an embryo with an embryogenesis inducing morphogenic developmental protein, more specifically a maize haploid embryo. Also provided for use in the methods of the disclosure are expression cassettes comprising a CPP fused to the ODP2 protein for use in combination with the chimeric signal peptide-WUSCHEL fusion protein operably whereby the proteins are engineered using genetic constructs designed with a chimeric endosperm or a transfer cell layer signal peptide-WUSCHEL fusion protein operably linked to a endosperm-specific promoter and polynucleotides encoding an endosperm or a transfer cell layer signal peptide-ODP2-CPP fusion peptide to translocate the expressed proteins from the endosperm to the embryo.

As used herein, the "anther" is part of the stamen containing the microsporangia that is attached to the filament. In angiosperms (flowering plants), the microsporangia produce microsporocyte, also known as the microspore mother cell, which then produces four microspores through meiosis. The microspores divide through mitosis to create pollen grains.

As used herein, the "locule" is a compartment within anthers containing the male gametes during microgametogenesis.

The term "microgametogenesis" is the process in plant reproduction where a microgametophyte, herein called a "microspore", develops into a tricellular pollen graint.

As used herein, the "microsporangium" or plural "microsporangia" is a sporangium that produces spores that give rise to male gametophytes. In nearly all land plants, sporangia are the site of meiosis and produce genetically distinct haploid spores.

The term "microspore embryogenesis" means the activation of androgenic embryogenesis of microspores that results or induces microspores to be in an embryogenic state.

The term "microspore-derived embryo" or "microspore-derived embryoid" means a cell or cells derived from a microspore with a cell fate and development characteristic of cells undergoing embryogenesis.

The term "androgenic" means induction of androgenesis in which the embryo contains only paternal chromosomes (parthenogenesis) for haploid or diploid cells.

As used herein, a "haploid" plant has a single set (genome) of chromosomes and the reduced number of chromosomes (n) in the haploid plant is equal to that in the gamete.

As used herein, a "diploid" plant has two sets (genomes) of chromosomes and the chromosome number (2n) is equal to that in the zygote.

As used herein, a "doubled haploid" or a "doubled haploid plant or cell" is one that is developed by the doubling of a haploid set of chromosomes. A plant or seed that is obtained from a doubled haploid plant that is selfed any number of generations may still be identified as a doubled haploid plant. A doubled haploid plant is considered a homozygous plant. A plant is a doubled haploid if it is fertile, even if the entire vegetative part of the plant does not consist of the cells with the doubled set of chromosomes. For example, a plant will be considered a doubled haploid plant if it contains viable gametes, even if it is chimeric.

As used herein, a "doubled haploid embryo" is an embryo that has one or more cells containing 2 sets of homozygous chromosomes that can then be grown into a doubled haploid plant.

The term "medium" includes compounds in liquid, gas, or solid state.

The present disclosure provides methods in which the chromosomes may be doubled at the microspore stage, at the embryo stage, at the mature seed stage, or anytime between pollination of the plant and before the germination of the haploid seed. Alternatively, spontaneous doubling may also occur.

The ex situ methods of the present disclosure promote microspore embryogenesis and cellular reprogramming by contacting an isolated microspore with a embryogenesis inducing morphogenic developmental protein. Isolated microspores may be specifically contacted with an exogenous embryogenesis inducing morphogenic developmental protein to improve maize microspore embryogenesis. For example, as disclosed herein the ex situ embryogenesis inducing morphogenic developmental protein treatment cellular reprogramming method uses a heterologous expression system to produce a purified, recombinant WUSCHEL protein (SEQ ID NO: 2). The methods of the present disclosure include delivery of the protein to the plant cell, for example using transfection reagents to further promote delivery of the exogenous WUSCHEL protein to the isolated microspore cells. In some aspects, the protein delivery method, with or without transfection reagents, can include electroporation methods and/or sonication methods, performed in the presence of agents such as dimethyl sulfoxide (DMSO), adjuvants, surfactants, and the like, that further promote delivery of an exogenous embryogenesis inducing morphogenic developmental protein into the microspore cells.

Also provided are, ex situ methods comprising contacting or treating an isolated microspore with an agent such as a small molecule or compound that enables cell fate reprogramming and stimulates embryogenic cell proliferation. The present disclosure provides methods comprising co-culturing isolated microspores in an induction media supplemented with a small molecule or compound. In some aspects, small-molecule inhibitors of protein kinases are used in the methods of the disclosure to cellularly reprogram a plant cell.

The methods of the disclosure also provide combining the protein delivery cellular reprogramming method, with or without transfection reagents, with and without electroporation methods and/or sonication methods, which may be performed in the presence of agents such as dimethyl sulfoxide (DMSO), adjuvants, surfactants, and the like described above and the cellular reprogramming treatments using a small molecule or compound described above to improve cellular reprogramming of a plant cell.

The methods of the disclosure also provide that the ex situ and/or in planta methods can subsequently include co-culturing the isolated microspores in contact with maize suspension "feeder cells" possessing embryogenic and cellular reprogramming properties. In particular, the method comprises co-culturing isolated microspores in the presence of transgenic maize suspension cell cultures transformed with a genetic construct expressing an embryogenesis inducing morphogenic developmental gene, such as the WUSCHEL protein (SEQ ID NO:7, and or ODP2 (SEQ ID NO:20).

In an aspect, the feeder cells are engineered to express polynucleotides encoding polypeptides involved in growth stimulation, embryogenesis, cellular reprogramming, and/or cell cycle stimulation to increase the frequency of haploid embryos, to increase the frequency of initiation of microspore-derived embryos, and/or to stimulate and increase chromosomal doubling efficiency. Polynucleotides useful in the methods of the disclosure include, but are not limited to, embryogenesis inducing morphogenic developmental genes and cell cycle genes including Cyclin A, Cyclin B, Cyclin C, Cyclin D, Cyclin E, Cyclin F, Cyclin G, and Cyclin H; Pin1; E2F; Cdc25; RepA genes and similar plant viral polynucleotides encoding replication-associated proteins. See U.S. Patent Publication No. 2002/0188965 incorporated herein by reference in its entirety.

In an aspect, the disclosure provides methods comprising co-culturing isolated microspores in the presence of non-transgenic maize suspension cell cultures (feeder cells), more specifically using feeder cells derived from genotypes with responsive androgenic phenotypes, such as for example ATCC40520 or ATCC40519 (see U.S. Pat. No. 5,306,864 A incorporated herein by reference in its entirety), or non-transgenic, responsive inbred strains such as HF1 (Martin and Widholm, (1996)).

The in planta method of the disclosure promotes embryogenesis from a tissue or organ of a plant by ectopically expressing a morphological developmental protein in a tissue or organ or in an adjacent tissue or organ. Genetic elements providing spatiotemporal expression and localization to particular tissues or organs of a plant are useful in the methods of the disclosure.

In an aspect, a promoter employed in the methods of the disclosure is the native *Z. mays* Ms44 promoter (SEQ ID NO:3) resulting in exploitation of the spatiotemporal expression and localization characteristic properties of Ms44, an anther-specific gene that is first detected in the tapetum cells during meiosis that persists through uninucleate microspore development (see Figure S1b in Fox et al., (2017) Plant Biotechnol. J., doi:10.1111/pbi.12689).

A signal peptide useful in the methods of the disclosure is the native *Z. mays* Ms44 signal peptide (SEQ ID NO:5; see also U.S. application Ser. Nos. 14/384,715, 14/384,743, 14/384,854 and 14/384,890 incorporated herein by reference in their entireties).

In the present disclosure, a heterologous expression cassette encoding the Ms44 promoter (SEQ ID NO: 3) regulating the anther-specific Ms44signal peptide (SEQ ID NO: 5) is fused to a polynucleotide encoding the WUSCHEL peptide (SEQ ID NO:7), thereby ectopically expressing the embryogenesis inducing morphogenic developmental gene during microgametogenesis. The methods of the disclosure allow embryogenesis inducing morphogenic developmental gene protein synthesis and processing in the tapetum cells for secretion into the locule, thus resulting in contact with the microspores and activity of the embryogenesis inducing morphogenic developmental protein to induce cellular reprogramming and activate microspore embryogenesis.

As used herein, a "chimeric gene expression cassette" is an expression cassette comprising a coding sequence operably linked to a transcription initiation region that is heterologous to the coding sequence and can include in the 5'-3' direction of transcription, a transcriptional initiation region (i.e., a promoter) and translational initiation region, a secretion signal peptide, an embryogenesis inducing morphogenic developmental gene sequence, a fluorescent protein sequence, and a transcriptional and translational termination region (i.e., termination region) functional in plants.

In an aspect, genetic constructs useful in the methods of the disclosure in a polynucleotide encoding a Ms44 promoter and Ms44 secretion signal peptide fused to a WUSCHEL protein which is also fused with a C-terminal 36 amino acid VirF translocation peptide sequence (SEQ ID NO:14), herein called "virF$^{c36}$", or is optionally fused to a C-terminal 127 amino acid VirF translocation peptide sequence (SEQ ID NO:16), herein called "virF$^{C127}$", or is is optionally fused to a 27 amino acid translocation signal peptide from the *A. rhizogenes* GALLS protein (SEQ ID NO:18), herein called "GS$^{C27}$", to promote increased morphogenic activity and cellular reprogramming.

In an aspect, genetic constructs useful in the methods of the disclosure with embryogenesis inducing morphogenic developmental gene protein activity (cellular reprogramming and embryogenesis induction activity) can also include fusion of the embryogenesis inducing morphogenic developmental gene with a cell penetrating peptide to increase cellular delivery and activity in a cell non-autonomous manner (increasing the embryogenesis inducing impact on surrounding/adjacent cells).

In an aspect, genetic constructs useful in the methods of the disclosure with embryogenesis inducing morphogenic developmental gene protein activity (cellular reprogramming and embryogenesis induction activity) can also include fusion of the embryogenesis inducing morphogenic developmental gene with a glucocorticoid receptor (GR)-based fusion protein system (SEQ ID NO: 48 and SEQ ID NO: 49) to conditionally localize protein activity to the nucleus by external application of animal hormone analogs into the in vitro tissue culture.

Promoters useful in the methods of the disclosure include the ZmBETL9 and 5' untranslated region or ZmBETL9-like promoter and 5' untranslated region (SEQ ID NO: 33 and SEQ ID NO:36, respectively) is fused to a polynucleotide encoding an embryogenesis inducing morphogenic developmental gene, such as, the WUSCHEL peptide (SEQ ID NO:7) or the OVULE DEVELOPMENT PROTEIN 2 (ODP2) (SEQ ID NO: 20), thereby ectopically regulating embryogenesis inducing morphogenic developmental gene expression during embryogenesis.

Endosperm secretion signal peptides, such as the N-terminal ZmBETL9 secretion signal peptide or ZmBETL9-like secretion signal peptide (SEQ ID NO: 32 and SEQ ID NO: 35, respectively) which are fused to an embryogenesis inducing morphogenic developmental gene protein thereby enabling protein translocation from the endosperm to the embryo cells during embryogenesis are useful in the method of the disclosure. Optionally, a translational fusion protein comprising a secretion signal peptide and an embryogenesis inducing morphogenic developmental gene protein can be fused to a translocation signal peptide. In an aspect, a translational fusion protein can comprise a cell penetrating peptide. The methods disclosed herein enable improved embryogenesis and cellular reprogramming in plant cells which also improve cellular responses in subsequent plant tissue culture methods.

The in planta cellular reprogramming methods of the disclosure improve maternal haploid embryo regeneration productivity and enable gene editing to provide regenerated gene-edited, maize doubled haploids wherein the treated cells, while not transgenic, are in contact with a embryogenesis inducing morphogenic developmental gene protein derived from triploid endosperm cells comprising one paternal allele expressing a trait that is a stable transformant.

In some aspects, a heterologous expression cassette encoding the ZmBETL9 promoter, 5' untranslated region (SEQ ID NO 33), and the N-terminal ZmBETL9 secretion signal peptide (SEQ ID NO: 31) or the ZmBETL9-like promoter, 5' untranslated region (SEQ ID NO: 36), and the N-terminal ZmBETL9-like secretion signal peptide (SEQ ID NO: 34) is fused to a polynucleotide encoding an embryogenesis inducing morphogenic developmental gene protein such as, the WUSCHEL peptide (SEQ ID NO:7) or the OVULE DEVELOPMENT PROTEIN 2 (ODP2) peptide (SEQ ID NO: 20), is used in the methods of the disclosure thereby ectopically regulating embryogenesis inducing morphogenic developmental gene expression during embryogenesis.

In an aspect, haploid cells can be contacted with an amount of a chromosome doubling agent to promote chromosome doubling followed by regenerating homozygous diploid plants from the treated haploid cells. The haploid microspore cells can be in contact with the doubling agent before, during, or after initiation of microspore embryogenesis or embryo maturation. After chromosome doubling, the doubled haploid embryo will contain 2 copies of paternally derived chromosomes. The efficiency of the process for obtaining doubled haploid plants from haploid embryos may be greater than 10%, 20%, 30%, 50%, 60%, 70%, 80%, or 90%. The duration of contact between the haploid cells and the chromosomal doubling agent may vary. Contact may be from less than 24 hours, for example 4-12 hours, to about a week. The duration of contact is generally from about 8 hours to 2 days.

Methods of chromosome doubling are disclosed in Antoine-Michard, S. et al., Plant cell, tissue organ cult., Cordrecht, the Netherlands, Kluwer Academic Publishers, 1997, 48(3):203-207; Kato, A., Maize Genetics Cooperation Newsletter 1997, 36-37; and Wan, Y. et al., TAG, 1989, 77: 889-892. Wan, Y. et al., TAG, 1991, 81: 205-211. The disclosures of which are incorporated herein by reference. Typical doubling methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% of amiprophos-methyl (APM) (5-225 µM) may be used. The amount of colchicine can range from approximately 400-600 mg/L or approximately 500 mg/L. The amount of pronamide in medium is approximately 0.5-20 µM. Examples of mitotic inhibitors are included in Table 1. Other agents may be used with the mitotic inhibitors to improve doubling efficiency. Such agents include dimethyl sulfoxide (DMSO), adjuvants, surfactants, and the like.

TABLE 1

| Common Name/Trade name | CAS | IUPAC |
|---|---|---|
| Colchicine and Colchicine Derivatives | | |
| colchicine/ acetyltrimethyl- colchicinic acid colchicine derivatives | | (S)-N-(5,6,7,9-tetrahydro-1,2,3,10-tetramethoxy-9-oxobenzo (a) heptalen-7-yl) acetamide |
| Carbamates | | |
| Carbetamide | (R)-1-(ethylcarbamoyl)ethyl carbanilate | (2R)-N-ethyl-2-[[(phenylamino)carbonyl]oxy]pro-panamide |
| chloropropham Propham | | |
| Benzamides | | |
| Pronamide/ propyzamide | 3,5-dichloro-N-(1,1-dimethylpropynyl)benz-amide | 3,5-dichloro-N-(1,1-dimethyl-2-propynyl)benzamide |
| Tebutam | | |
| Benzoic Acids | | |
| Chlorthal dimethyl (DCPA), Dicamba/dianat/ disugran (dicamba-methyl) (BANVEL, CLARITY) | 3,6-dichloro-o-anisic acid | 3,6-dichloro-2-methoxybenzoic acid |
| Dinitroaniline chromosome doubling agents | | |
| benfluralin/benefin/ (BALAN) | N-butyl-N-ethyl-α,α,α-trifluoro-2,6-dinitro-p-toluidine | N-butyl-N-ethyl-2,6-dinitro-4-(trifluoromethyl)benzenamine |
| Butralin | (RS)-N-sec-butyl-4-tert-butyl-2,6-dinitroaniline | 4-(1,1-dimethylethyl)-N-(1-methylpropyl)-2,6-dinitrobenzenamine |
| Chloralin | | |
| dinitramine | N1,N1-diethyl-2,6-dinitro-4-trifluoromethyl-m-phenylenediamine | N3,N3-diethyl-2,4-dinitro-6-(trifluoromethyl)-1,3-benzenediamine |
| ethalfluralin (Sonalan) | N-ethyl-α,α,α-trifluoro-N-(2-methylallyl)-2,6-dinitro-p-toluidine | N-ethyl-N-(2-methyl-2-propenyl)-2,6-dinitro-4-(trifluoromethyl)benzenamine |
| fluchloralin | N-(2-chloroethyl)-2,6-dinitro-N-propyl-4-(trifluoromethyl)aniline or N-(2-chloroethyl)-α,α,α-trifluoro-2,6-dinitro-N-propyl-p-toluidine | N-(2-chloroethyl)-2,6-dinitro-N-propyl-4-(trifluoromethyl)benzenamine |
| isopropalin | 4-isopropyl-2,6-dinitro-N,N-dipropylaniline | 4-(1-methylethyl)-2,6-dinitro-N,N-dipropylbenzenamine |
| methalpropalin | α,α,α-trifluoro-N-(2-methylallyl)-2,6-dinitro-N-propyl-p-toluidine | N-(2-methyl-2-propenyl)-2,6-dinitro-N-propyl-4-(trifluoromethyl)benzenamine |
| nitralin | 4-methylsulfonyl-2,6-dinitro-N,N-dipropylaniline | 4-(methylsulfonyl)-2,6-dinitro-N,N-dipropylbenzenamine |
| oryzalin (SURFLAN) | 3,5-dinitro-N4,N4-dipropylsulfanilamide | 4-(dipropylamino)-3,5-dinitrobenzenesulfonamide |
| pendimethalin (PROWL) | N-(1-ethylpropyl)-2,6-dinitro-3,4-xylidine | N-(1-ethylpropyl)-3,4-dimethyl-2,6-dinitrobenzenamine |
| prodiamine | 5-dipropylamino-α,α,α-trifluoro-4,6-dinitro-o-toluidine or 2,6-dinitro-N1,N1-dipropyl -4-trifluoromethyl-m-phenylenediamine | 2,4-dinitro-N3,N3-dipropyl-6-(trifluoromethyl)-1,3-benzenediamine |
| profluralin | N-cyclopropylmethyl-α,α,α-trifluoro-2,6-dinitro-N-propyl-p-toluidine or N-cyclopropylmethyl-2,6-dinitro-N-propyl-4-trifluoromethylaniline | N-(cyclopropylmethyl)-2,6-dinitro-N-propyl-4-(trifluoromethyl)benzenamine |
| trifluralin (TREFLAN, TRIFIC, TRILLIN) | α,α,α-trifluoro-2,6-dinitro-N,N-dipropyl-p-toluidine | 2,6-dinitro-N,N-dipropyl-4-(trifluoromethyl)benzenamine |

TABLE 1-continued

| Common Name/Trade name | CAS | IUPAC |
|---|---|---|
| Phosphoroamidates | | |
| APM (Amiprofos methyl); amiprophos-methyl | | |
| Butamifos | O-ethyl O-6-nitro-m-tolyl (RS)-sec-butylphosphoramidothioate | O-ethyl O-(5-methyl-2-nitrophenyl) (1-methylpropyl)phosphoramidothioate |
| Pyridines | | |
| Dithiopyr | | |
| Thiazopyr | methyl 2-difluoromethyl-5-(4,5-dihydro-1,3-thi azol -2-yl)-4-isobutyl-6-trifluoromethylnicotinate | methyl 2-(difluoromethyl)-5-(4,5-dihydro-2-thiazolyl)-4-(2-methylpropyl)-6-(trifluoromethyl)-3-pyridinecarboxylate |

The in planta methods of the disclosure provide stable transgenic "microspore activator" parental inbred lines useful in genetic crosses with a second, wild type parent inbred line to create a first generation $F_1$ hybrid.

The methods of the disclosure, in an aspect, use this hemizygous transgenic $F_1$ hybrid for generating an immature tassel that can produce florets with anthers containing developing microspores. The microspores are the products of meiosis, and thus, each male gamete has a unique combination of genes inherited from the parents along recombined chromosomes due to chromosomal crossover events during meiosis. A single copy transgene that is at a single locus in a hemizygous state can segregate in a 1:1 ratio during meiosis resulting in half of the gametes being wild type and the other half of the gametes having inherited the transgenic locus. After meiosis, the wild type and transgenic gametes continue to develop in planta with all developing microspores exposed to the embryogenesis inducing morphogenic developmental gene protein which is secreted from sporophytic tapetum cells originating from protein translation of the single copy of the transgene in the hemizygous $F_1$ genome. Upon isolation of the microspores from the tassel tissues, the methods of the disclosure induce cellular programming activity during microgametogenesis to improve microspore embryogenesis responsiveness and cellular reprograming in vitro. Selection of non-transgenic microspore-derived embryoids is performed using methods known to those skilled in the art.

In an aspect, two different inbred strains are cross-fertilized to create first generation $F_1$ zygotic embryos developing within the fertilized ear of the maternal parent. Each $F_1$ zygotic embryo has two sets (genomes) of chromosomes, one from each parent. The immature $F_1$ zygotic embryos can be subsequently isolated from the maternal ear after fertilization, for example 8 to 16 days after fertilization, for transformation purposes to stably integrate into the $F_1$ plant genome a polynucleotide encoding an embryogenesis inducing morphogenic developmental cellular reprogramming factor. In this manner, selection of $F_1$ plants with a single copy of the embryogenesis inducing morphogenic developmental cellular reprogramming genetic construct in a hemizygous state can be performed for sampling tassel tissues producing microspores within anthers. In respect to the inserted embryogenesis inducing morphogenic developmental cellular reprogramming transgene, the microspores will segregate in a 1:1 ratio during gametogenesis resulting in half of the gametes being wild type and the other half of the gametes having inherited the transgenic embryogenesis inducing morphogenic developmental cellular reprogramming locus. The methods of the disclosure thereby allow for selecting $F_2$ generation wild-type microspores with improved embryogenesis responsiveness from a hemizygous $F_1$ hybrid for creating doubled haploid populations.

In an aspect, the methods of the disclosure also provide in planta protein delivery. The methods comprise transforming a maize haploid inducer line to stably integrate and express a heterologous expression cassette, or cassettes, encoding two major functional activities: one activity comprising proteins for inducing somatic embryogenesis and cellular reprogramming and a second activity comprising proteins useful for gene editing purposes. Both components are operably linked to a promoter, or promoters, expressed within the endosperm, specifically the embryo surrounding region (ESR) and or the Basal Endosperm Transfer Layer (BETL). The methods of the disclosure use the transformed haploid inducer line for fertilizing the maternal ear of a target plant to generate haploid embryos with improved doubled haploid plantlet regeneration and/or improved regeneration of gene-edited, doubled haploid progeny. In these methods, expression of a heterologous expression cassette comprising an embryogenesis inducing morphogenic developmental gene protein from the paternal allele within triploid endosperm cells results in the proteins being translocated through transfer cells into the haploid embryo using secretion signal peptides characteristic of endosperm transfer cells. The present methods provide maternal haploid embryo having increased levels of embryogenesis and plantlet regeneration capabilities once rescued haploid embryos are cultured in vitro.

A summary of SEQ ID NOS: 1-49 is presented in Table 2.

TABLE 2

Summary of SEQ ID NOS: 1-49.

| SEQ ID NO: | Polynucleotide (DNA) or Polypeptide (PRT) | Name | Description |
|---|---|---|---|
| 1 | DNA | WUS-histag | WUS-hexahistidine-tagged coding sequence |
| 2 | PRT | WUS-histag | WUS-hexahistidine-tagged amino acid sequence |
| 3 | DNA | ZM-Ms44 PRO | Zea mays Ms44 promoter sequence |
| 4 | DNA | ZM-Ms44SP | Zea mays Ms44 signal peptide coding sequence |
| 5 | PRT | ZM-Ms44SP | Zea mays Ms44 signal peptide amino acid sequence |
| 6 | DNA | ZM-WUS2 | Zea mays WUS2 coding sequence |
| 7 | PRT | ZM-WUS2 | Zea mays WUS2 amino acid sequence |
| 8 | DNA | L3 | Linker3 coding sequence |
| 9 | PRT | L3 | Linker3 amino acid sequence |
| 10 | DNA | AC-GFP1 | Aequorea coerulescens GFP1 coding sequence |
| 11 | PRT | AC-GFP1 | Aequorea coerulescens GFP1 amino acid sequence |
| 12 | DNA | ZM-Ms44 TERM | Zea mays Ms44 terminator coding sequence |
| 13 | DNA | WUS-virFC36 | WUS-virFC36 translational fusion coding sequence |
| 14 | PRT | WUS-virFC36 | WUS-virFC36 translational fusion amino acid sequence |
| 15 | DNA | WUS-virFC127 | WUS-virFC127 translational fusion coding sequence |
| 16 | PRT | WUS-virFC127 | WUS-virFC127 translational fusion amino acid sequence |
| 17 | DNA | WUS-GALLS (GSC27) | WUS-GALLS (GSC27) translational fusion coding sequence |
| 18 | PRT | WUS-GALLS (GSC27) | WUS-GALLS (GSC27) translational fusion amino acid sequence |
| 19 | DNA | ZM-ODP2 | Zea mays ODP2 coding sequence |
| 20 | PRT | ZM-ODP2 | Zea mays ODP2 amino acid sequence |
| 21 | DNA | ZM-KNT1 CPP | Zea mays knotted 1 CPP coding sequence |
| 22 | PRT | ZM-KNT1 CPP | Zea mays knotted 1 CPP amino acid sequence |
| 23 | DNA | SP-TP10 CPP | Saccharomyces pombe TP10 CPP coding sequence |
| 24 | PRT | SP-TP10 CPP | Saccharomyces pombe TP10 CPP amino acid sequence |
| 25 | DNA | CA-Zebra CPP | Candida albicans Zebra CPP coding sequence |
| 26 | PRT | CA-Zebra CPP | Candida albicans Zebra CPP amino acid sequence |
| 27 | DNA | PEP1 CPP | PEP1 CPP coding sequence |
| 28 | PRT | PEP1 CPP | PEP1 CPP amino acid sequence |
| 29 | DNA | HIV-1 TAT CPP | HIV-1 TAT CPP coding sequence |
| 30 | PRT | HIV-1 TAT CPP | HIV-1 TAT CPP amino acid sequence |
| 31 | DNA | ZM-BETL9SP | Zea mays Basal Endosperm Transfer Layer 9 secretion signal peptide coding sequence |
| 32 | PRT | ZM-BETL9SP | Zea mays Basal Endosperm Transfer Layer 9 secretion signal peptide amino acid sequence |
| 33 | DNA | ZM-BETL9 PRO | Zea mays Basal Endosperm Transfer Layer 9 promoter coding sequence |
| 34 | DNA | ZM-BETL9-likeSP | Zea mays Basal Endosperm Transfer Layer9-like secretion signal peptide coding sequence |
| 35 | PRT | ZM-BETL9-likeSP | Zea mays Basal Endosperm Transfer Layer9-like secretion signal peptide amino acid sequence |
| 36 | DNA | ZM-BETL9-like PRO | Zea mays Basal Endosperm Transfer Layer9-like promoter coding sequence |
| 37 | DNA | ODP2C445 | ODP2C445-GALLSC27-FLAG coding sequence |
| 38 | PRT | ODP2C445 | ODP2C445-GALLSC27-FLAG amino acid sequence |
| 39 | DNA | AM-CFP-ZM-FEM2 | Anemonia majano Cyan Fluorescent Protein (CFP) operably linked to the Zea mays FEM2 promoter coding sequence |
| 40 | DNA | TA-T2A | Thosea asigna virus T2A coding sequence |
| 41 | PRT | TA-T2A | Thosea asigna virus T2A amino acid sequence |

TABLE 2-continued

Summary of SEQ ID NOS: 1-49.

| SEQ ID NO: | Polynucleotide (DNA) or Polypeptide (PRT) | Name | Description |
|---|---|---|---|
| 42 | DNA | SP-CAS9 | *Streptococcus pyogenes* (CRISPR) CAS9 nuclease coding sequence |
| 43 | PRT | SP-CAS9 | *Streptococcus pyogenes* (CRISPR) CAS9 nuclease amino acid sequence |
| 44 | DNA | AC-Cpf1 MO | Maize optimized *Acidaminococcus* sp. strain BV3L6 Cpf1 nuclease coding sequence |
| 45 | PRT | AC-Cpf1 | *Acidaminococcus* sp. strain BV3L6 Cpf1 nuclease amino acid sequence |
| 46 | DNA | WUS-histag-GZCPP | WUS-hexahistidine-tagged Gamma-zein CPP translational fusion protein coding sequence |
| 47 | PRT | GZCPP-WUS-histag | WUS-hexahistidine-tagged Gamma-zein CPP translational fusion protein amino acid sequence |
| 48 | DNA | WUS-GR | WUS glucocorticoid receptor (GR) fusion protein coding sequence |
| 49 | PRT | WUS-GR | WUS glucocorticoid receptor (GR) fusion protein amino acid sequence |

In an aspect, the disclosed methods and compositions can be used to introduce into plant cells and organs with increased efficiency and speed polynucleotides useful to target a specific site for modification in the genome of a plant derived from the somatic embryo. Site specific modifications that can be introduced with the disclosed methods and compositions include those produced using any method for introducing site specific modification, including, but not limited to, through the use of gene repair oligonucleotides (e.g. US Publication 2013/0019349), or through the use of site-specific DNA cleaving technologies such as TALENs, meganucleases, zinc finger nucleases, CRISPR-Cas, and the like. For example, the disclosed methods and compositions can be used to introduce a CRISPR-Cas system into a plant cell or plant, for the purpose of genome modification of a target sequence in the genome of a plant or plant cell, for selecting plants, for deleting a base or a sequence, for gene editing, and for inserting a polynucleotide of interest into the genome of a plant or plant cell. Thus, the disclosed methods and compositions can be used together with a CRISPR-Cas system to provide for an effective system for modifying or altering target sites and nucleotides of interest within the genome of a plant, plant cell or seed. In an aspect, the Cas endonuclease gene is a plant optimized Cas9 endonuclease, wherein the plant optimized Cas9 endonuclease is capable of binding to and creating a double strand break in a genomic target sequence the plant genome.

Genome-editing techniques such as zinc finger nucleases (ZFNs), transcription activator-like effector nucleases (TALENs), or homing meganucleases, are available for producing targeted genome perturbations.

The Cas endonuclease is guided by the guide nucleotide to recognize and optionally introduce a double strand break at a specific target site into the genome of a cell. The CRISPR-Cas system provides for an effective system for modifying target sites within the genome of a plant, plant cell or seed. Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest. The disclosed compositions and methods can be used to introduce a CRISPR-Cas system for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene includes a gene that is generally coupled, associated or close to or in the vicinity of flanking CRISPR loci. The terms "Cas gene" and "CRISPR-associated (Cas) gene" are used interchangeably herein.

Cas endonuclease relates to a Cas protein encoded by a Cas gene, wherein the Cas protein is capable of introducing a double strand break into a DNA target sequence. The Cas endonuclease is guided by the guide polynucleotide to recognize and optionally introduce a double strand break at a specific target site into the genome of a cell. As used herein, the term "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide nucleotide, but only if the correct protospacer-adjacent motif (PAM) is approximately oriented at the 3' end of the target sequence (see FIG. 2A and FIG. 2B of WO/2015/026883, published Feb. 26, 2015). In an aspect, the Cas endonuclease gene is a Cas9 endonuclease.

In another aspect, the Cas endonuclease gene is plant, maize or soybean optimized Cas9 endonuclease, such as, but not limited to those shown in FIG. 1A of US2016/0208272, and incorporated herein by reference.

The term "Cas protein" or "Cas endonuclease" or "Cas nuclease" or "Cas polupeptide" refers to a polypeptide encoded by a Cas (CRISPR-associated) gene. A Cas protein includes but is not limited to Cas9 protein, Cas9 orthologs, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease", that when in complex with a suitable polynucleotide component, is capable of recognizing, binding to, and optionally nicking or cleaving all or part of a specific polynucleotide target sequence. A Cas endonuclease described herein comprises one or more nuclease domains. A Cas protein is further defined as a functional fragment or functional variant of a native Cas protein, or a protein that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native Cas protein, and retains at least partial activity.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", and "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site. In some aspects, the components are provided as a ribonucleoprotein complex ("RNP") of a Cas endonuclease protein and a guide RNA.

Described herein are methods for genome editing with CRISPR Associated (Cas) endonucleases during microspore embryogenesis or for portions of the microspore embryogenesis induction. Following characterization of the guide RNA (or guide polynucleotide) and PAM sequence, a ribonucleoprotein (RNP) complex comprising the Cas endonuclease and the guide RNA (or guide polynucleotide) may be utilized to modify a target polynucleotide, including but not limited to: synthetic DNA, isolated genomic DNA, or chromosomal DNA in other organisms, including plants. To facilitate optimal expression and nuclear localization (for eukaryotic cells), the gene comprising the Cas endonuclease may be optimized as described in WO2016186953 published 24 Nov. 2016, and then delivered into cells as DNA expression cassettes by methods known in the art. The components necessary to comprise an active RNP may also be delivered as RNA with or without modifications that protect the RNA from degradation or as mRNA capped or uncapped (Zhang, Y. et al., 2016, Nat. Commun. 7:12617) or Cas protein guide polynucleotide complexes (WO2017070032 published 27 Apr. 2017), or any combination thereof. Additionally, a part or part(s) of the complex may be expressed from a DNA construct while other components are delivered as RNA with or without modifications that protect the RNA from degradation or as mRNA capped or uncapped (Zhang et al. 2016 Nat. Commun. 7:12617) or Cas protein guide polynucleotide complexes (WO2017070032 published 27 Apr. 2017) or any combination thereof.

As related to the Cas endonuclease, the terms "functional fragment," "fragment that is functionally equivalent," and "functionally equivalent fragment" are used interchangeably herein. These terms refer to a portion or subsequence of the Cas endonuclease sequence of the present disclosure in which the ability to create a double-strand break is retained.

As related to the Cas endonuclease, the terms "functional variant," "variant that is functionally equivalent" and "functionally equivalent variant" are used interchangeably herein. These terms refer to a variant of the Cas endonuclease of the present disclosure in which the ability to create a double-strand break is retained. Fragments and variants can be obtained via methods such as site-directed mutagenesis and synthetic construction.

In addition to the double-strand break inducing agents, site-specific base conversions can also be achieved to engineer one or more nucleotide changes to create one or more edits into the genome. These include for example, a site-specific base edit mediated by an C•G to T•A or an A•T to G•C base editing deaminase enzymes (Gaudelli et al., Programmable base editing of A•T to G•C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. A catalytically "dead" or inactive Cas9 (dCas9), for example a catalytically inactive "dead" version of a Cas9 ortholog disclosed herein, fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA.

As used herein, the term "guide nucleotide" relates to a synthetic fusion of two RNA molecules, a crRNA (CRISPR RNA) comprising a variable targeting domain, and a tracrRNA. In an aspect, the guide nucleotide comprises a variable targeting domain of 12 to 30 nucleotide sequences and a RNA fragment that can interact with a Cas endonuclease.

As used herein, the term "guide polynucleotide" relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide nucleotide".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In an aspect, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In an aspect, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides.

In an aspect, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In an aspect, the RNA that guides the RNA Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In an aspect, the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide nucleotide" (when composed of a contiguous stretch of RNA nucleotides) or "single guide DNA" (when composed of a contiguous stretch of DNA nucleotides) or "single guide nucleotide-DNA" (when composed of a combination of RNA and DNA nucleotides). In an aspect of the disclosure, the single guide nucleotide comprises a cRNA or cRNA fragment and a tracrRNA or tracrRNA fragment of the type II CRISPR/Cas system that can form a complex with a type II Cas endonuclease, wherein the guide nucleotide Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In an aspect, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

In an aspect of the disclosure, the guide nucleotide comprises a cRNA (or cRNA fragment) and a tracrRNA (or tracrRNA fragment) of the type II CRISPR/Cas system that can form a complex with a type II Cas endonuclease, wherein the guide nucleotide Cas endonuclease complex can direct the Cas endonuclease to a plant genomic target site, enabling the Cas endonuclease to introduce a double strand break into the genomic target site. The guide nucleotide can be introduced into a plant or plant cell directly using any method known in the art such as, but not limited to, particle bombardment or topical applications. In an aspect, the guide nucleotide can be introduced indirectly by introducing a recombinant DNA molecule comprising the corresponding guide DNA sequence operably linked to a plant specific promoter that is capable of transcribing the guide nucleotide in the plant cell. The term "corresponding guide DNA" includes a DNA molecule that is identical to the RNA molecule but has a "T" substituted for each "U" of the RNA molecule. In an aspect, the guide nucleotide is introduced via particle bombardment or using the disclosed methods and compositions for *Agrobacterium* transformation of a recombinant DNA construct comprising the corresponding guide DNA operably linked to a plant U6 polymerase III promoter.

Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI—for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families. TAL effector nucleases are a new class of sequence-specific nucleases that can be used to make double-strand breaks at specific target sequences in the genome of a plant or other organism. (Miller, et al. (2011) Nature Biotechnology 29:143-148).

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a nonspecific endonuclease domain, for example nuclease domain from a Type Ms endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

The terms "target site," "target sequence," "target DNA," "target locus," "genomic target site," "genomic target sequence," and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature.

As used herein, terms "endogenous target sequence" and "native target sequence" are used interchangeably herein to refer to a target sequence that is endogenous or native to the genome of a plant and is at the endogenous or native position of that target sequence in the genome of the plant. In an aspect, the target site can be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site," "altered target sequence" "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The following examples are offered by way of illustration and not by way of limitation.

EXAMPLES

The aspects of the disclosure are further defined in the following Examples, in which parts and percentages are by weight and degrees are Celsius, unless otherwise stated. These Examples, while indicating aspects of the disclosure, are given by way of illustration only. From the above discussion and these Examples, one skilled in the art can ascertain the essential characteristics of the aspects of the disclosure, and without departing from the spirit and scope thereof, can make various changes and modifications of them to adapt to various usages and conditions. Thus, various modifications in addition to those shown and described herein will be apparent to those skilled in the art from the foregoing description. Such modifications are also intended to fall within the scope of the appended claims.

Example 1

Microspore Embryogenesis Improved after Embryogenesis Inducer Agent Treatment

Following microspore isolation, ATCC40520 microspores (see U.S. Pat. No. 5,602,310 incorporated herein by reference in its entirety) were cultured in a petri dish in a 9% sucrose induction medium as a control or a 9% sucrose induction medium supplemented with a 1 µM final concentration of hemin (Sigma-Aldrich, catalog # H9039) at 28° C. under dark conditions.

After 8 days of in vitro tissue culture, four biological replicates of proliferating embryo-like structures were sampled from each of the control and the hemin-treated ATCC40520 tissue cultures for embryogenesis induction and processed for gene expression analysis using methods known in the art (data not shown).

Following microspore isolation, ATCC40520 microspores and EH, anelite inbred, that is known to be less responsive relative to the ATCC40520 genotype, were each individually cultured in a petri dish in a 9% sucrose induction medium as a control or a 9% sucrose induction medium supplemented with a 1 µM final concentration of hemin at 28° C. under dark conditions.

Microspore phenotypes were scored for each of ATCC40520 and EH after 21 days of treatment (+/− hemin). A multicellular structure (MCS) phenotype was scored when a unicellular-derived structure resulting from randomly oriented divisions within a surrounding, intact exine wall was observed. If the surrounding exine was ruptured and a release of cells was observed, then the response was scored as a proliferative embryo-like structure (ELS).

As shown in FIG. 1A (control) and FIG. 1B (hemin treatment), hemin treatment of ATCC40520 microspores increased cellular proliferation and the development of embryo-like structures (ELS). The number of ELS approximately doubled in responsive cultures after 21 days of treatment (+/− hemin). Moreover, hemin treatment improved the quality of the embryo-like structures as evidenced by an increased proportion of spherical embryoids and a decreased proportion of non-spherical embryoids as shown in FIG. 1B.

As shown in FIG. 1C the corresponding gene expression analysis of the control and hemin treated ATCC40520 microspores shows an improved cellular reprogramming fate indicated by the increased expression of embryogenic transcripts relative to a correspondingly decreased expression of pollen associated transcripts.

As shown in FIG. 1D (control) and FIG. 1E (hemin treatment), hemin treatment of inbred EH microspores increased cellular proliferation in responsive cultures after 21 days of culture. As shown in FIG. 1F, hemin treatment increased in the percentage of inbred EH microspores scored with the MCS phenotype and the ELS phenotype over inbred control EH microspores.

Following microspore isolation, the ATCC40520 microspores were cultured in a petri dish in a 9% sucrose induction medium as the control or a 9% sucrose induction medium supplemented with varying concentrations of small molecule compounds including, N-[(2R)-2,3-dihydroxypropoxy]-3,4-difluoro-2-(2-fluoro-4-iodoanilino)benzamide, herein referred to as "PD0325901" (ESI BIO 1010 Atlantic Avenue, Suite 102, Alameda, Calif. 94501), anthra (1,9-cd)pyrazol-6(2H)-one, herein referred to as "SP600125" (ESI BIO 1010 Atlantic Avenue, Suite 102, Alameda, Calif. 94501), 4-(4-Fluorophenyl)-2-(4-methylsulfinylphenyl)-5-(4-pyridyl)1H-imidazole, herein referred to as "SB203580" (ESI BIO 1010 Atlantic Avenue, Suite 102, Alameda, Calif. 94501), and N-benzyl-2-(pyrimidin-4-ylamino)-1,3-thiazole-4-carboxamide, herein referred to as "thiazovivin" (ESI BIO 1010 Atlantic Avenue, Suite 102, Alameda, Calif. 94501). The in vitro tissue cultures were incubated at 28° C. under dark conditions and evaluated after 7 days.

Figure 2B:
FIG. 2B shows a stereo microscope micrograph of ATCC40520 cells cultured for 7 days post isolation in a 9% sucrose induction medium supplemented with PD0325901 (0.19 mM final concentration).
Figure 2C:
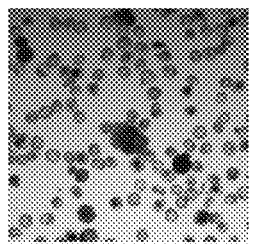
FIG. 2C shows a stereo microscope micrograph of ATCC40520 cells 7 cultured for days post isolation in a 9% sucrose induction medium supplemented with PD0325901 (0.39 mM final concentration).
Figure 2D:
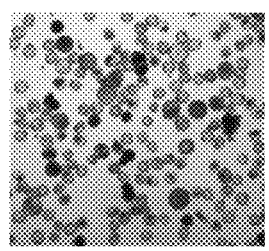
FIG. 2D shows a stereo microscope micrograph of ATCC40520 cells cultured for 7 days post isolation in a 9% sucrose induction medium supplemented with PD0325901 (1.5 mM final concentration).
Figure 2E:
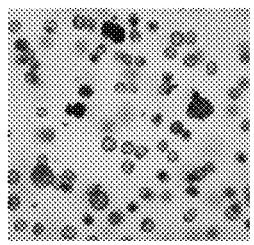
FIG. 2E shows a stereo microscope micrograph of ATCC40520 cells cultured for 7 days post isolation in a 9% sucrose induction medium without SP600125 (anthra(1,9-cd)pyrazol-6(2H)-one) (negative control).
Figure 2F:
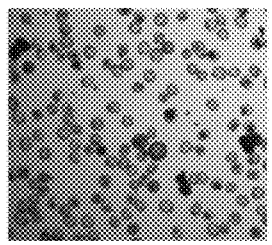
FIG. 2F shows a stereo microscope micrograph of ATCC40520 cells cultured for 7 days post isolation in a 9% sucrose induction medium supplemented with SP600125 (0.19 mM final concentration).
Figure 2G:
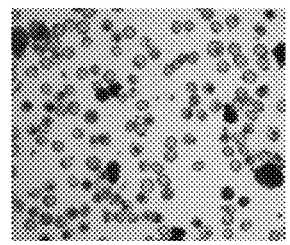
FIG. 2G shows a stereo microscope micrograph of ATCC40520 cells cultured for 7 days post isolation in a 9% sucrose induction medium supplemented with SP600125 (6.25 mM final concentration).
Figure 2H:
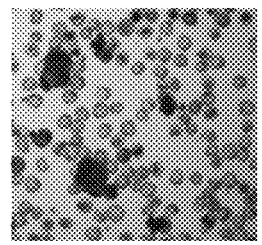
FIG. 2H shows a stereo microscope micrograph of ATCC40520 cells cultured for 7 days post isolation in a 9% sucrose induction medium supplemented with SP600125 (50 mM final concentration).
Figure 2I:
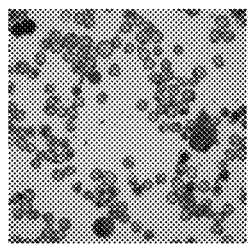
FIG. 2I shows a stereo microscope micrograph of ATCC40520 cells cultured for 7 days post isolation in a 9% sucrose induction medium without SB203580 (4-(4-Fluorophenyl)-2-(4-methylsulfinylphenyl)-5-(4-pyridyl)1H-imidazole) (negative control).
Figure 2J:
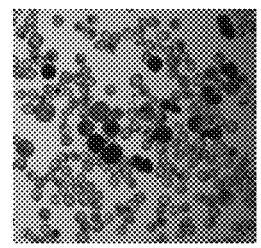
FIG. 2J shows a stereo microscope micrograph of ATCC40520 cells cultured for 7 days post isolation in a 9% sucrose induction medium supplemented with SB203580 (0.78 mM final concentration).
Figure 2K:
FIG. 2K shows a stereo microscope micrograph of ATCC40520 cells cultured for 7 days post isolation in a 9% sucrose induction medium supplemented with SB203580 (3.22 mM final concentration).
Figure 2L:
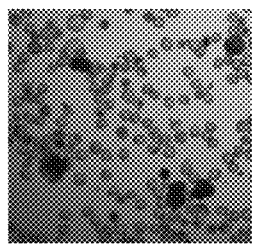
FIG. 2L shows a stereo microscope micrograph of ATCC40520 cells cultured for 7 days post isolation in a 9% sucrose induction medium supplemented with SB203580 (50 mM final concentration).
Figure 2M:
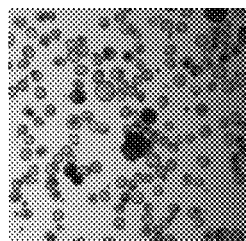
FIG. 2M shows a stereo microscope micrograph of ATCC40520 cells cultured for 7 days post isolation in a 9% sucrose induction medium without thiazovivin (N-benzyl-2-(pyrimidin-4-ylamino)-1,3-thiazole-4-carboxamide) (negative control).
Figure 2N:
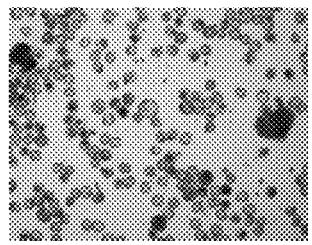
FIG. 2N shows a stereo microscope micrograph of ATCC40520 cells cultured for 7 days post isolation in a 9% sucrose induction medium supplemented with thiazovivin (0.39 mM final concentration).
Figure 2O:
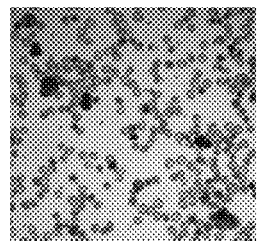
FIG. 2O shows a stereo microscope micrograph of ATCC40520 cells cultured for 7 days post isolation in a 9% sucrose induction medium supplemented with thiazovivin (12.5 mM final concentration).
Figure 2P:
FIG. 2P shows a stereo microscope micrograph of ATCC40520 cells cultured for 7 days post isolation in a 9% sucrose induction medium supplemented with thiazovivin (50 mM final concentration).

Increased cellular proliferation was observed in response to the small molecule compound treatments as shown in FIG. 2A-FIG. 2P show images captured at 2× magnification using an EVOS FL auto digital microscope (Thermo Fisher Scientific). FIG. 2A-FIG. 2P show improved proportions of multicellular structures, observed as dark cells with an increased spherical shape relative to non-treated control cells. Exine rupture, an important step in microspore embryo growth and further development, was observed within 7 days following in vitro culture initiation using each of the small molecule compound treatment kinase inhibitors, demonstrating an increased induction of microspore embryogenesis and an improved efficiency of cellular reprogramming.

Accordingly, the disclosure provides methods of inducing embryogenesis and producing reprogrammed cells from a differentiated cell or haploid gametic cell using embryogenesis inducing agents such as for example, small molecule compounds. As described more fully below, small molecule compound treatment kinase inhibitors may be used in combination with an embryogenesis inducing morphogenic developmental gene protein product to promote cellular reprogramming of cells and to increase microspore embryogenesis responsiveness.

Example 2

Co-Culturing Maize Microspores with Feeder Suspension Cell Cultures Expressing an Embryogenesis Inducing Polypeptide Induces Microspore Embryogenesis Methods for creating and maintaining maize suspension cell cultures are known to those skilled in the art. Isolated microspores were co-cultured with maize suspension cells stably expressing an embryogenesis inducing morphogenic developmental gene polypeptide, such as a WUSCHEL polypeptide (SEQ ID NO:2) and a ZmODP2 polypeptide (SEQ ID NO:20), an AP2/ERF transcription factor to determine if media conditioned with maize suspension cells expressing embryogenesis inducing morphogenic developmental polypeptides ("feeder cells") supported improved microspore embryogenesis responses in non-transgenic isolated microspores. Microspores were isolated as described above. The isolated wild type microspores and the transgenic suspension feeder cells were partition co-cultured in a 4% sucrose liquid induction media using Corning® brand 12 mm Transwell® 0.4 µm pore polycarbonate membrane cell culture inserts (Sigma-Aldrich catalog # CLS3401). Microspores, in isolation medium, were first added to a well followed by adding the Transwell 0.4 µm pore polycarbonate membrane cell culture insert, and lastly adding the feeder cells to the polycarbonate membrane cell culture insert. The final media volume was adjusted to ensure all cells were submerged in the 4% sucrose liquid induction media.

Conversely, the method can include adding the suspension cells first to a well followed by adding the polycarbonate membrane cell culture insert and finally adding the isolated microspores to the polycarbonate membrane cell culture insert.

After approximately one month of co-culture, the isolated wild type microspores were transferred from the co-culture conditions (4% sucrose liquid induction medium) to solidified 4% sucrose induction medium (0.6% agarose) for subsequent embryogenesis development. Wild type microspores co-cultivated with transgenic feeder cells expressing a combination of the WUSCHEL and ODP2 embryogenesis inducing morphogenic developmental gene polypeptides demonstrated enhanced development of multicellular structures within 14 days after placement on solidified 4% sucrose induction medium, while corresponding levels of development of multicellular structures were not observed in non-treated wells (wells lacking transgenic feed cells), even after 32 days on solidified 4% sucrose induction medium.

These results show that co-cultivation of wild type microspores with transgenic feeder cells expressing a combination of WUSCHEL and ODP2 embryogenesis inducing morphogenic developmental gene polypeptides and/or cultivation of wild type microspores in media conditioned with feeder cell supernatant supports improved microspore embryogenesis responses in non-transgenic microspores.

Example 3

Evaluation of Ex Situ Co-Culturing of Maize Microspores and an Exogenous Polypeptide on Microspore Embryogenesis WUSCHEL protein expression and purification was performed using a heterologous expression system expressing a plasmid encoding a ZmWUS2-hexa histidine-tag (SEQ ID NO:1) sequence transformed into DH10Bac cells (Thermo Fisher Scientific catalog #10361012) to generate baculoviruses. Baculovirus-infected SF9 insect cells (Thermo Fisher Scientific catalog #12552014) were incubated for 72 hours at 27° C. The infected insect cells were harvested by centrifugation.

Purification of the recombinant ZmWUS2-hexa histidine-tag protein (SEQ ID NO:2) was performed using commercially available protein purification methods Following microspore isolation from inbred EH, ZmWUS2-hexa histidine-tag protein treatments were performed for each culture by combining 505 μL of a 4% sucrose induction media, 37.5 μL of molecular grade bovine serum albumin (BSA; 20 mg/ml) (Sigma-Aldrich catalog # B8667) and 7.5 μL of protease inhibitor (Sigma-Aldrich catalog # P9599) and with 250 μL of the purified recombinant ZmWUS2-hexa histidine-tag protein. After gently mixing, the solution was filter sterilized within a sterile environment using a 0.2 μm filter (Pall Corporation catalog #4612). Optionally, an isolation medium was buffered with L-glutathione reduced (Sigma-Aldrich catalog #G4251). The L-glutathione reduced (1.5 mg/mL) stock solution was created by adding 0.075 g of L-glutathione reduced to 50 mL of sterile water, mixing, and then filter sterilizing the solution. A working solution was created by adding 15.63 μL of the L-glutathione reduced stock solution to 15.60 mL of isolation medium to create a final 1.5 mg/L concentration.

Figure 3A:
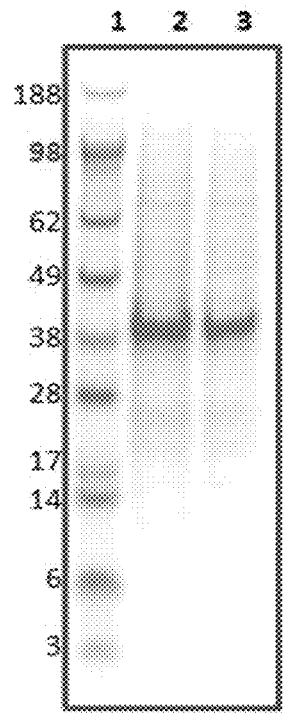
FIG. 3A shows Coomassie blue staining using a 12% Bis-tris gel with the SeeBlue® Plus2 Pre-Stained Standard (Thermo Fisher Scientific catalog #LC5925) (lane 1) and purified recombinant ZmWUS2-hexa histidine-tag protein samples, replicate 1 (lane 2) and replicate 2 (lane 3).
Figure 3B:
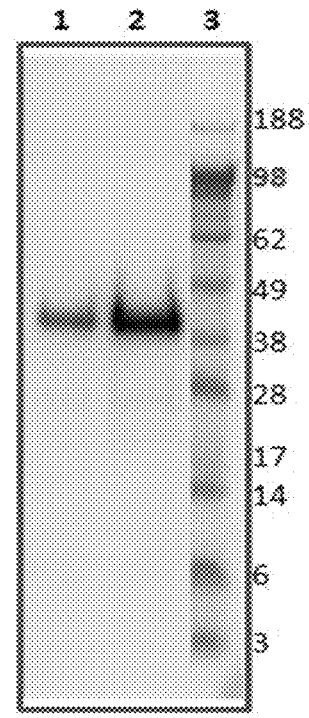
FIG. 3B shows a western blot analysis of the purified recombinant ZmWUS2-hexa histidine-tag proteins described in FIG. 3A using a primary anti-His monoclonal antibody and a secondary anti-mouse-HRP antibody (1:5, 000) with recombinant ZmWUS2-hexa histidine-tag protein replicate 1 (lane 1), recombinant ZmWUS2-hexa histidine-tag protein replicate 2 (lane 2) and the SeeBlue® Plus2 Pre-Stained Standard (lane 3).

As shown in FIG. 3A coomassie staining of the 12% Bis-tris SDS-PAGE electrophoresis gel of the purified recombinant ZmWUS2-hexa histidine-tag protein samples purified above in two respective replicates, replicate 1 (lane 2) and replicate 2 (lane 3) have similar total protein levels. As shown in FIG. 3B the Western blot analysis of the purified recombinant ZmWUS2-hexa histidine-tag protein samples using a primary anti-His monoclonal antibody (described above) and a secondary anti-mouse-HRP antibody (describes above) confirms the presence of the expected purified recombinant ZmWUS2-hexa histidine-tag protein. This purified recombinant ZmWUS2-hexa histidine-tag protein is used in the ex situ treatments described below.

Figure 3C:
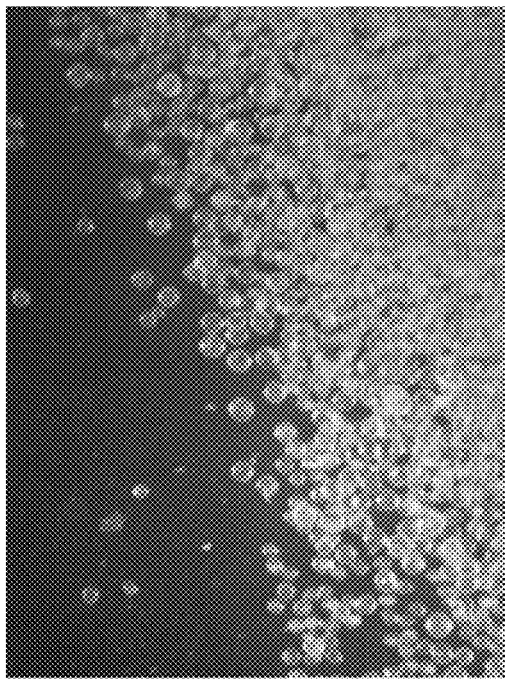
FIG. 3C shows wild type microspore embryogenesis without a recombinant ZmWUS2-hexa histidine-tag protein treatment.
Figure 3D:
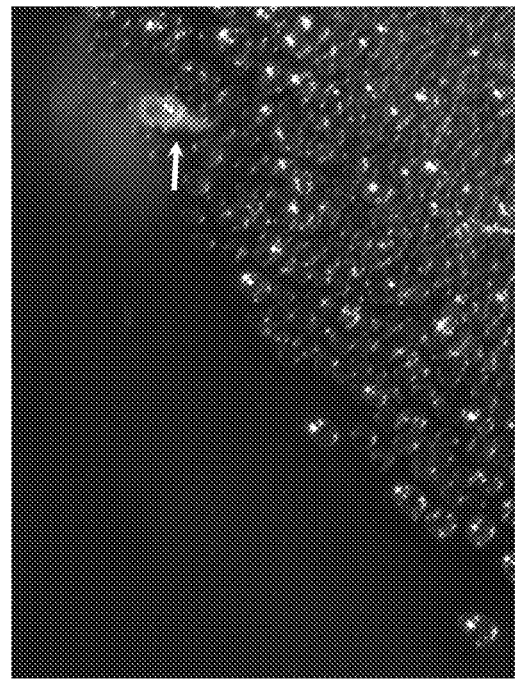
FIG. 3D shows biological activity for inducing cellular reprogramming to activate microspore embryogenesis in wild type microspores treated with a purified recombinant ZmWUS2-hexa histidine-tag protein. A microspore-derived embryo with a developed radicle and root hairs was observed.

As shown in FIG. 3D, isolated microspores of a recalcitrant elite inbred when treated with a purified ZmWUS2-hexa histidine-tag protein demonstrated improved microspore responsiveness and embryogenesis induction when compared to control (microspores cultured in the absence of the purified ZmWUS2-hexa histidine-tag protein) (FIG. 3C). Embryoid development revealed a suspensor with root hairs (FIG. 3D), demonstrating improved cellular reprogramming and activated microspore embryogenesis in wild type microspores.

Example 4

Evaluation of Ex Situ Co-Culturing of Maize Microspores and an Exogenous Polypeptide Fused with an Exogenous Cell Penetrating Peptide on Microspore Embryogenesis GAMMA ZEIN-ZmWUS2-hexa histidine-tag protein expression and purification is performed using a heterologous expression system expressing a plasmid encoding a GAMMA ZEIN-ZmWUS2-hexa histidine-tag (SEQ ID NO:46) sequence transformed into DH10Bac cells to generate baculoviruses. Baculovirus-infected SF9 insect cells are incubated for 72 hours at 27° C. The infected insect cells are harvested by centrifugation. Purification of the recombinant GAMMA ZEIN-ZmWUS2-hexa histidine-tag protein (SEQ ID NO:47) is performed as described in EXAMPLE 3.

Isolated microspores treated with a purified GAMMA ZEIN-ZmWUS2-hexa histidine-tag protein are expected to demonstrate improved microspore responsiveness and embryogenesis induction when compared to control (microspores cultured in the absence of the purified GAMMA ZEIN-ZmWUS2-hexa histidine-tag protein).

Example 5

Improved Exogenous Polypeptide Protein Delivery into Microspores Using Protein Transfection Transfection reagent preparation using the cationic lipid based Pro-Ject™ transfection reagent (Thermo Fisher Scientific catalog #89850) was performed by adding 250 μL of methanol to the tube containing the dried transfection reagent, vortexing for 30 seconds at top speed, and dispensing 10 μL of Pro-ject™ plus methanol to 1.5 mL Eppendorf tubes. The transfection reagent was evaporated from the tubes within a chemical fume hood for 4 hours drying time at room temperature and the tubes were stored the tubes at −20° C. until use.

Upon use, 100 μL of isolation medium containing 50 ng of the purified ZmWUS2-hexa histidine-tag protein was added to each tube and 900 μL microspore culture medium was dispensed into each transfection tube to re-hydrate the transfection reagent and encapsulate the protein. The 1 mL volume of this solution was combined with a 1 mL volume of microspores isolated from a $F_1$ hybrid tassel of an EHxGR genetic cross. The microspores were suspended in isolation medium and each 2 mL volume was dispensed into a well of a 24 well microtiter plate (Lab Safety Supply catalog #11L794).

The isolation medium was further supplemented with bovine serum albumin, protease inhibitor and L-glutathione reduced, with or without the cationic lipid-based Pro-Ject™ transfection reagent, and with or without the ZmWUS2-hexa histidine-tag protein treatments (ZmWUS2-hexa histidine-tag protein buffer as a control for comparison to the ZmWUS2-hexa histidine-tag protein).

Each plate was sealed with parafilm and incubated at 28° C. under dark conditions. After 72 hours, cells with a diameter greater than or equal to 70 μm were collected and washed using a Fisherbrand™ cell strainer (fisher scientific by Thermo Fisher Scientific catalog # FBH #22-363) and cultured in a 35 mm tissue culture petri dish with 1.5 mL of a 9% sucrose induction medium. Each plate was sealed with parafilm and incubated at 28° C. under dark conditions. After 18 days, all cells were collected and rinsed using 70 μm Fisherbrand™ cell strainer and evaluated for the activation of cellular reprogramming and the induction of microspore embryogenesis.

Microspore viability was scored by counting plasmolyzed, collapsed cells (i.e. "non-viable") and translucent, spherical cells corresponding to the original state (i.e. "viable"). After 72 hours post-isolation and in vitro culture growth using a 4% sucrose liquid induction medium, cell viability showed on average a 2.1-fold improvement was observed in the microspores cultured in the ZmWUS2-hexa histidine-tag protein buffer (control treatment) and on average a 5.1-fold improvement in cell viability was observed in the microspores cultured in the ZmWUS2-hexa histidine-tag protein (experimental treatment).

Figure 4A:
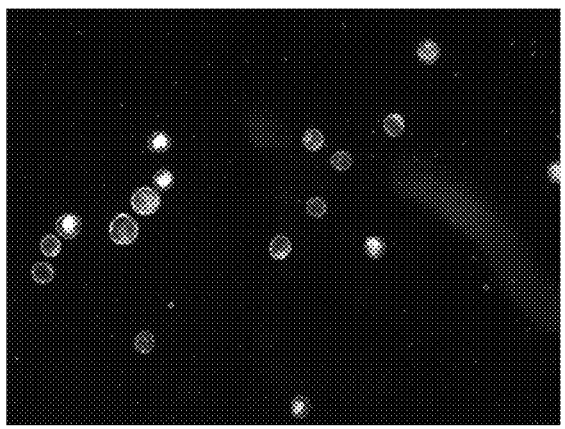
FIG. 4A shows a stereo microscope micrograph of microspore embryogenesis development without a purified recombinant WUSCHEL protein and without a transfection reagent treatment after 32 days of culture in a 4% sucrose induction medium under dark conditions.
Figure 4B:
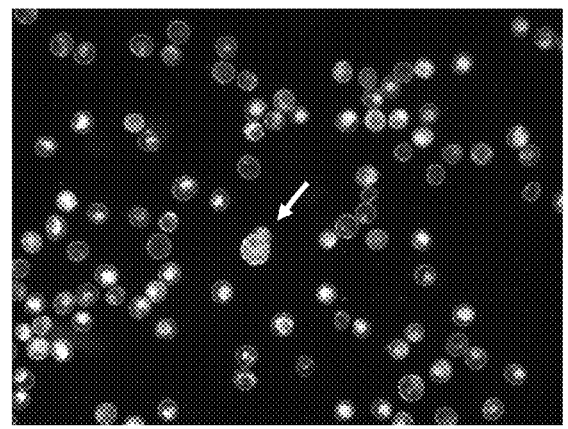
FIG. 4B shows a stereo microscope micrograph of microspore embryogenesis development with a purified recombinant WUSCHEL protein and without a transfection reagent treatment after 32 days of culture in a 4% sucrose induction medium under dark conditions.
Figure 4C:
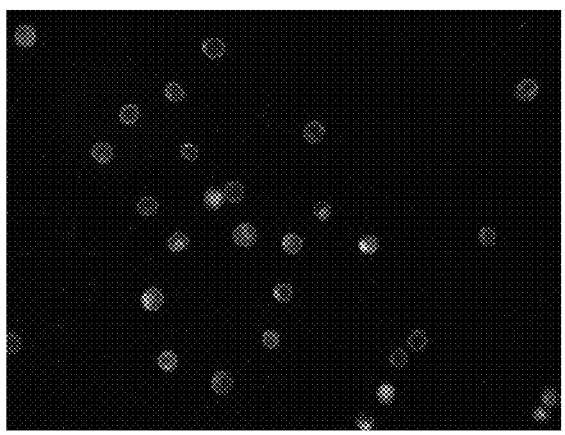
FIG. 4C shows a stereo microscope micrograph of microspore embryogenesis development without a purified recombinant WUSCHEL protein and with a transfection reagent treatment after 32 days of culture in a 4% sucrose induction medium under dark conditions.
Figure 4D:
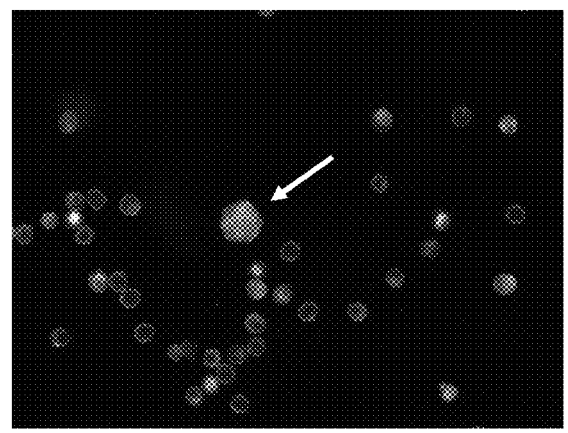
FIG. 4D shows a stereo microscope micrograph of microspore embryogenesis development with a purified recombinant WUSCHEL protein and a transfection reagent treatment after 32 days of culture in a 4% sucrose induction medium under dark conditions.

As shown in FIG. 4A, after 18 days of culture fewer cells were viable in the control treatment (absence of the ZmWUS2-hexa histidine-tag protein) relative to the ZmWUS2-hexa histidine-tag protein-treated cells (experimental treatment) (FIG. 4B). Use of the transfection reagents in the absence of the ZmWUS2-hexa histidine-tag protein failed to promote any further embryogenic development (FIG. 4C), while cell proliferation was seen in microspores cultured in the ZmWUS2-hexa histidine-tag protein combined with the cationic lipid-based Pro-Ject™ transfection reagent (FIG. 4D) resulting in improved activation of cellular reprogramming and the induction of microspore embryogenesis.

Example 6

Microspore Electroporation Provides Improved Exogenous Polypeptide Delivery

A Neon® Transfection System (Thermo Fisher Scientific catalog #MPK5000) and Neon® kit (Thermo Fisher Scientific catalog #MPK10025) is used per the manufacturer's instructions. The ex situ ZmWUS2-hexa histidine-tag protein treatment is prepared by mixing 12.5 µL of ZmWUS2-hexa histidine-tag protein (SEQ ID NO:2; 10 µg total, 0.8 µg/µL stock) with 12.5 µL Lipofectamin 3000 followed by 30 minutes incubation at room temperature. Sucrose is added to the resuspension buffer (buffer R) to a 0.4 M final concentration and filter sterilized.

Isolated microspores are resuspended in a 2% (V/V) dimethyl sulfoxide (DMSO)/9% suscrose induction medium solution and incubated for 15 minutes at room temperatures, the microspores are pelleted, and the supernatant is removed. The microspores are washed three times with phosphate buffered saline (PBS; Gibco™ 10010023), resuspended in Electrolytic Buffer E (Thermo Fisher Scientific catalog #MPK5000) and mixed with the ZmWUS2-hexa histidine-tag protein/Lipofectamine 3000 solution followed by room temperature incubation for 10 minutes and then incubation on ice for 10 minutes.

DMSO-mediated electroporation was used to increase ZmWUS2-hexa histidine-tag protein uptake into isolated microspores through multiple pulse conditions.

After electroporation, the microspores are incubated on ice for 10 min and then at room temperature for 5 minutes, followed by adding 100 µL of a 9% sucrose induction medium into each electroporated cell sample which was repeated three times at 5 minute intervals. Following de-plasmolysis, the cells are plated onto solidified isolation medium using SeaPlaque™ agarose (0.6%).

Isolated microspores treated with a purified ZmWUS2-hexa histidine-tag protein in combination with electroporation are expected to demonstrate improved microspore responsiveness and embryogenesis induction when compared to control (microspores cultured in the absence of the purified ZmWUS2-hexa histidine-tag protein and not subject to electroporation).

Example 7

Creation of a Maize Microspore Activator Strain

Figure 5A:
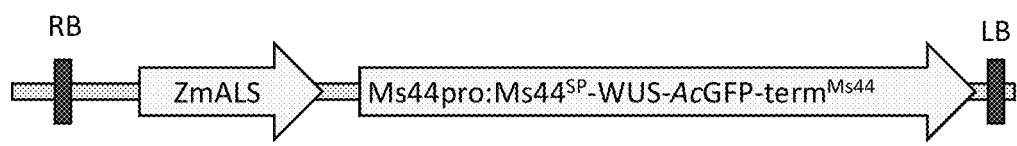
FIG. 5A is a schematic diagram of a construct for creating stable maize microspore activator strains expressing a WUSCHEL-GFP fusion protein.
Figure 5B:
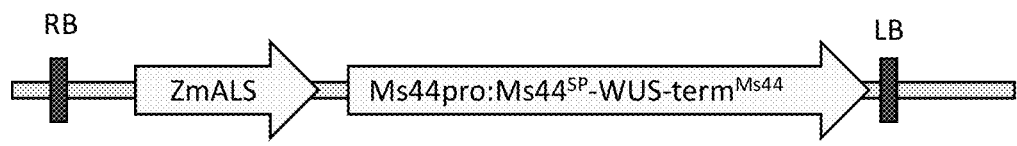
FIG. 5B is a schematic diagram of a construct for creating stable maize microspore activator strains expressing a WUSCHEL protein.
Figure 5C:
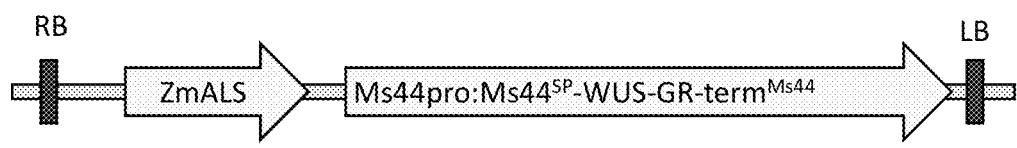
FIG. 5C is a schematic diagram of a construct for creating stable maize microspore activator strains expressing a WUSCHEL-GLUCOCORTICOID RECEPTOR (GR) fusion protein.

Expression cassettes were designed to increase microspore embryogenesis in planta prior to microspore isolation. Specifically, a polynucleotide encoding in operable linkage the Ms44 promoter (SEQ ID NO:3), the Ms44 signal peptide sequence (SEQ ID NO:4) fused to a WUSCHEL embryogenesis inducing morphogenic developmental gene sequence (SEQ ID NO:6) with a linker sequence (SEQ ID NO:8), the fluorescent AC-GFP1 gene (SEQ ID NO:10) and the Ms44 terminator sequence (SEQ ID NO:12) was used (FIG. 5A). This construct facilitated protein expression and transport of the embryogenesis inducing morphogenic developmental gene protein from the tapetum cells to the locule of the anther which induced cellular reprogramming and initiated microspore embryogenesis within the spatiotemporal localization of tapetum cells resulting in protein processing and secretion of the WUSCHEL embryogenesis modulation factor into the locule during microgametogenesis. Additional expression cassettes useful in the methods of the present disclosure are shown in FIG. 5B and FIG. 5C.

The expression cassette was incorporated into an *Agrobacterium* transformation vector. *Agrobacterium* transformation was preformed using standard protocols known in the art. Alternatively, transformation vectors can be introduced to plant cells by generally known biolistic transformation methods.

Figure 6A:
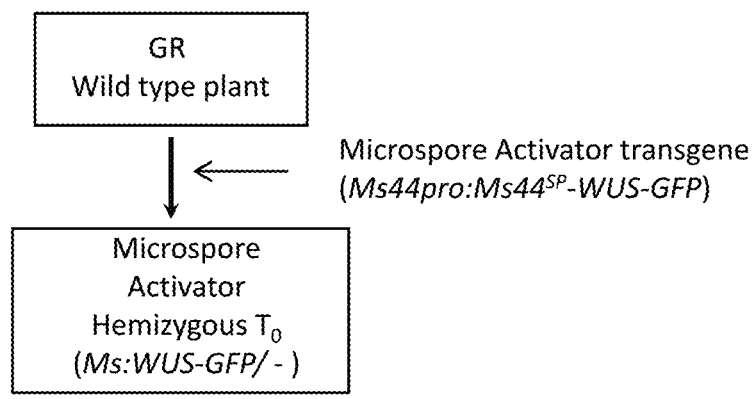
FIG. 6A is a schematic diagram depicting a transformation method schematic to create a $T_0$ microspore activator strain.

Following transformation and selection of hemizygous transformed plants (see FIG. 6A), anther and leaf samples were obtained from plants at anthesis to test for the presence of the embryogenesis inducing morphogenic developmental gene protein. Anther and leaf tissues from 2 to 3 $T_0$ hemizygous transformants were combined as pooled samples, protein was extracted from each pool, and a western blot was performed using a custom polyclonal antibody recognizing WUSCHEL epitopes and an anti-GFP antibody.

Figure 6B:
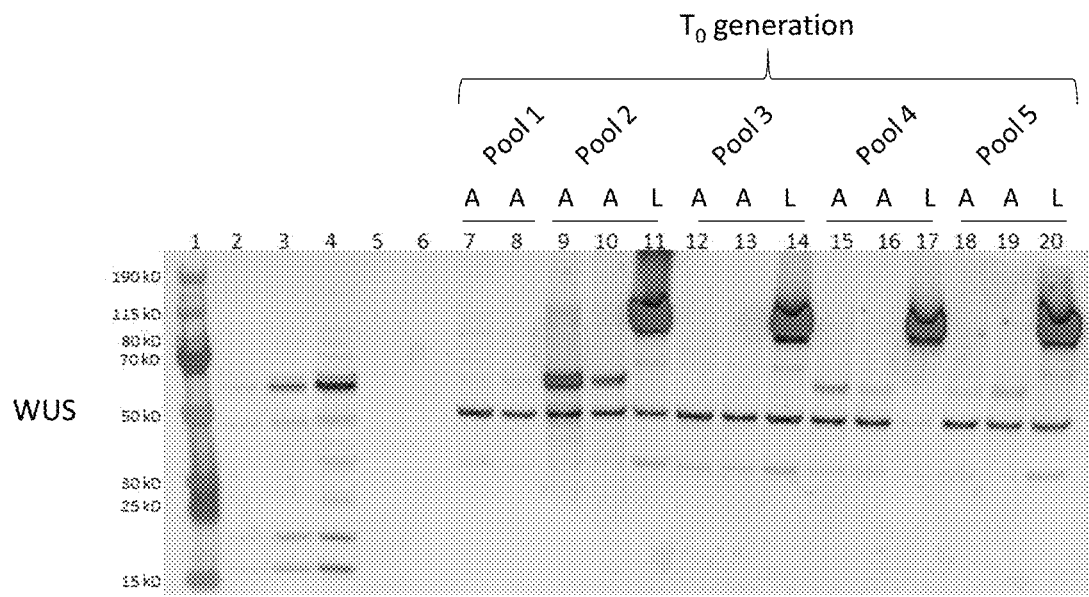
FIG. 6B shows a western blot of protein samples isolated from anther (A) and leaf (L) tissue using a custom polyclonal anti-WUSCHEL antibody (protein standard (lane 1), lanes of purified, recombinant WUS-GFP fusion protein (lanes, 2, 3, and 4), anther pools (pool 1, lanes 7 and 8; pool 2 lanes 9 and 10; pool 3, lanes 12 and 13; pool 4, lanes 15 and 16; and pool 5, lanes 18 and 19, leaf samples are shown in lanes 11, 14, 17, and 20).
Figure 6C:
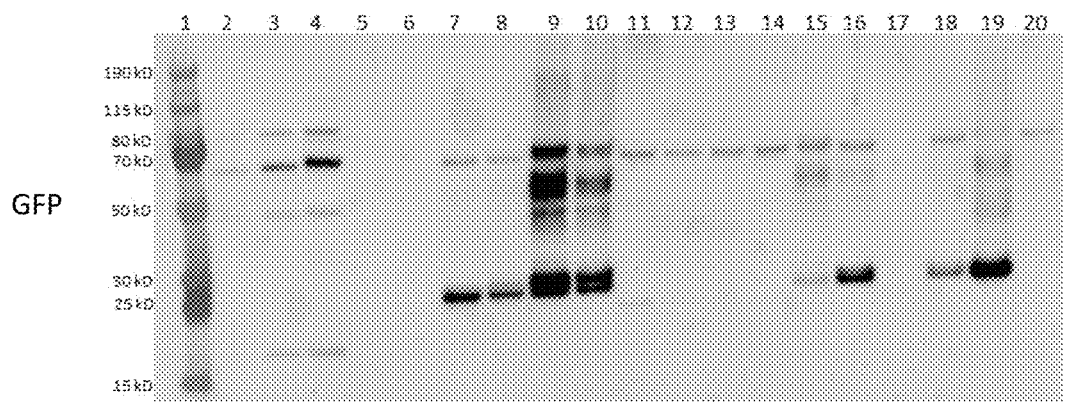
FIG. 6C shows a western blot of protein samples isolated from anther (A) and leaf (L) tissue using an anti-GFP antibody (protein standard (lane 1), lanes of purified, recombinant WUS-GFP fusion protein (lanes, 2, 3, and 4), anther pools (pool 1, lanes 7 and 8; pool 2 lanes 9 and 10; pool 3, lanes 12 and 13; pool 4, lanes 15 and 16; and pool 5, lanes 18 and 19, leaf samples are shown in lanes 11, 14, 17, and 20).

A western blot, (FIG. 6B), shows a band in the anther tissues at approximately 60 kD representing the expected protein size for the WUSCHEL-GFP fusion protein and confirmed tissue-specific expression of the WUSCHEL-GFP fusion protein in anthers and not in leaves and the spatial and temporal expression of the embryogenesis inducing morphogenic developmental gene protein.

Microspores were isolated from the $T_0$ hemizygous transformants and were cultured. After 6 days of culture the initiation of microspore embryogenesis was observed as evidenced by the presence of multicellular structures within the sporopollenin coat and/or rupturing of the exine of the microspore. After 11 days of culture, embryo-like structures were observed. These results confirmed that in planta expression of an embryogenesis inducing polynucleotide encoding a morphogenic developmental gene polypeptide induced cellular reprogramming and initiated microspore embryogenesis.

Example 8

Wild-Type Microspore Embryos Selected from a Hemizygous Microspore Activator Parent The microspore activator hemizygous $T_0$ plant (FIG. 6A) generated in Example 7 was self-pollinated and the genotypes were sorted. A single-copy homozygous $T_1$ microspore activator event was selected. Genetic crosses were made between the single-copy event, homozygous $T_1$ microspore activator and a parent 2 wild type inbred to create a hemizygous $F_1$ hybrid (see FIG. 7) and ultimately to create populations of paternal gamete-derived (androgenic) doubled haploids in maize. Alternatively, a single copy hemizygous $T_0$ microspore activator event is crossed with a parent 2 wild type inbred to create a hemizygous $F_1$ hybrid. Similarly, a single copy hemizygous $T_1$ microspore activator event is crossed with a parent 2 wild type inbred to create a hemizygous $F_1$ hybrid. A $F_1$ hybrid ("Null") was also created by a controlled cross of a null segregant plant (progeny of the microspore activator hemizygous $T_0$ transgenic plant) with an identical parental non-transgenic plant.

Upon growth of the hemizygous $F_1$ hybrids, microgametogenesis occurred in the reproductive tissues and the transgene insertion site segregated in a Mendelian fashion. Independently of gametogenesis, the diploid sporophytic tapetum cells transformed with a single copy of the heterologous expression cassette (FIG. 5A) encoding the embryogenesis inducing morphogenic developmental gene polypeptide in a hemizygous state expressed and secreted the embryogenesis inducing morphogenic developmental polypeptide within each tapetum cell. During microsporangium development the embryogenesis inducing WUSCHEL-GFP fusion polypeptide was delivered into the locule where all microspores were developing which allowed all microspores to be treated with the embryogenesis inducing morphogenic developmental polypeptide in vivo which improved microspore embryogenesis response in vitro following microspore isolation.

Figure 8A:
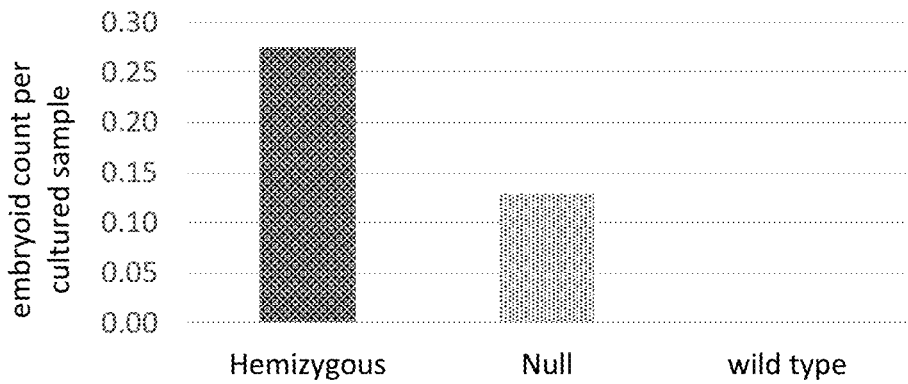
FIG. 8A shows a bar graph representing increased levels of embryogenic responsiveness of in vitro microspore cultures from a hemizygous Ms44-WUS activator hybrid cross in response to in vivo WUS-GFP activity.
Figure 8B:
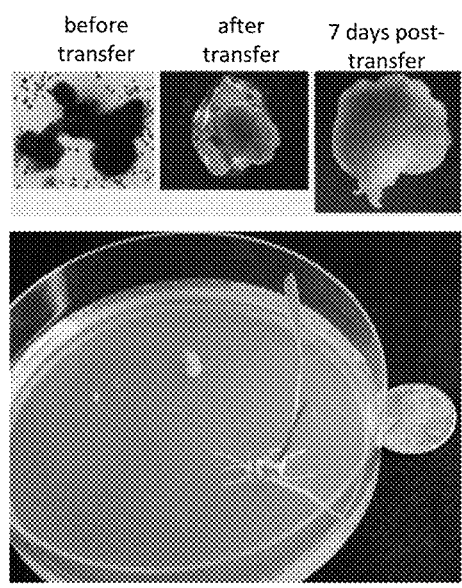
FIG. 8B shows images of a microspore-derived embryo-like structure before and after embryo regeneration resultant in a microspore-derived haploid plant.

As shown in FIG. 8A microspores isolated from the hemizygous $F_1$ hybrid and subjected to standard tissue culture conditions (induction media without any embryogenesis inducing compounds) post isolation exhibited an increased generation of embryoids and/or an increased generation of embryo-like structures when compared to the Null or wild type $F_1$ hybrid microspores subjected to the same post isolation tissue culture conditions. The only embryoid to germinate and develop into a plant was derived from a hemizygous $F_1$ hybrid donor plant (FIG. 8B), whereas no plants were generated from embryoids isolated from the Null or the wild type $F_1$ donor plants.

Figure 8C:
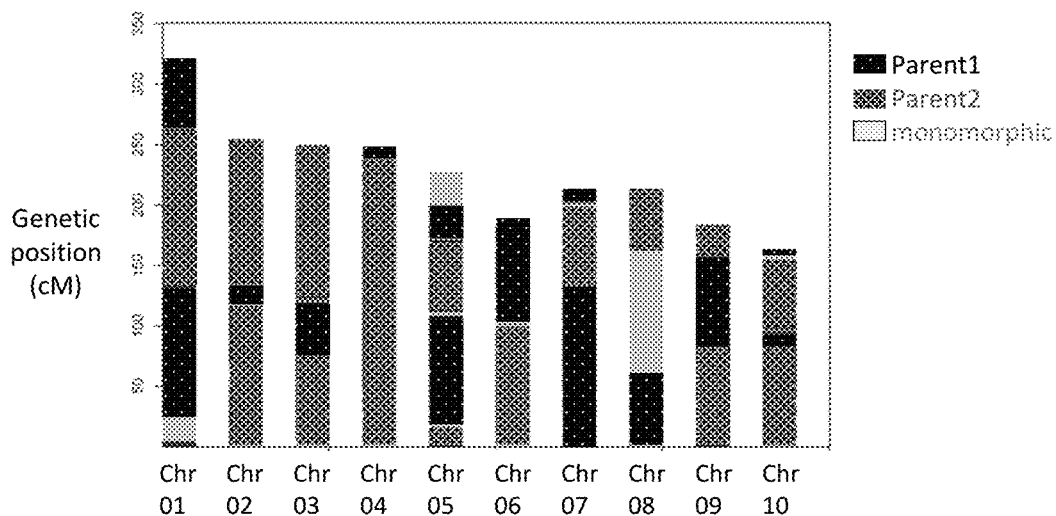
FIG. 8C shows an ideogram depicting meiotic recombination breakpoints per maize chromosome one to ten (Chr; x axis) with inherited allelic patterns (Parent1—black regions; Parent 2—gray regions; non-informative, monomorphic—light gray regions) positioned in respect to genetic map position (cM (centimorgan); y axis).

This regenerated plantlet was genotyped using methods known in the art and the inheritance of its genetic markers was mapped along the maize genome (FIG. 8C). As shown in FIG. 8C the inheritance of parental alleles along each maize chromosome was consistent with meiotic recombination patterns expected from a hybrid parent, thus confirming that this was a microspore-derived plant. As these results demonstrate the methods of the disclosure developed recombinant inbred lines without requiring pollination control methods or without propagating self-fertilized lines into isogenic states.

Microspores isolated from the tassels of the hemizygous $F_1$ hybrids (which have undergone in planta cellular reprogramming and initiation of microspore embryogenesis within the locule during microgametogenesis) can be subjected to tissue culture methods including, but not limited to, further cellular reprogramming and embryogenesis induction methods as described herein.

Figure 7:
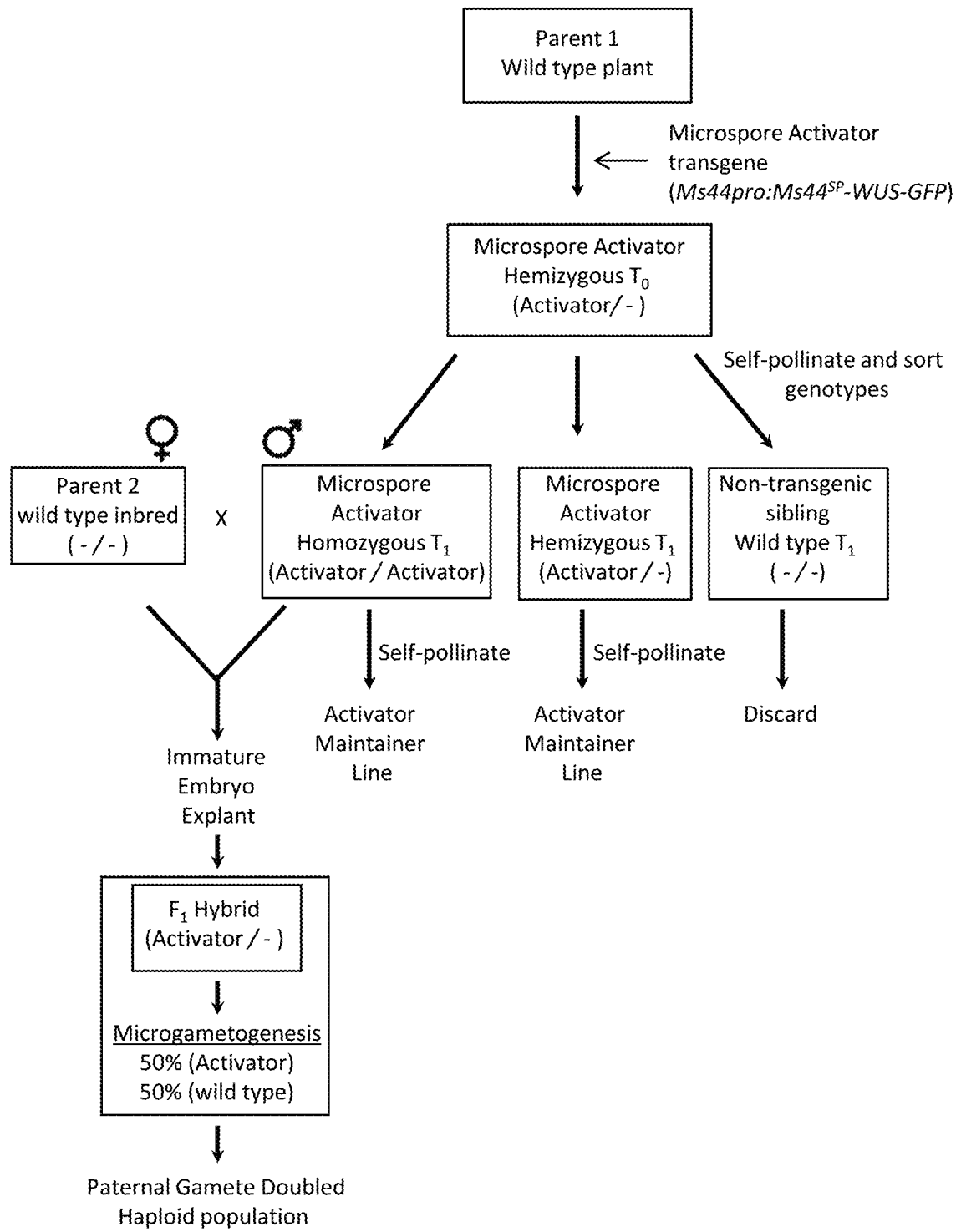
FIG. 7 is a schematic diagram depicting a method for selecting wild type microspore-derived embryos from a hemizygous Ms44-WUS microspore activator hybrid cross.

Using methods known in the art, wild-type microspore-derived embryos from the hemizygous $F_1$ hybrid can be genotyped and selected to create paternal gamete (androgenic) doubled haploid populations (FIG. 7).

Maintenance of the desired single-copy homozygous $T_1$ microspore activator event for use as the microspore activator parent can be performed by further propagation of selected, stable transgenic individuals, including methods to self-fertilize a homozygous transgenic line or by self-fertilization of a hemizygous line followed by selection of homozygous progeny.

For some breeding purposes, it can be of particular interest to create segregating material from crosses including, but not limited to, $F_2$ or later filial generations derived from the hemizygous $F_1$ hybrid, from back-crossed material after a first or later generation and/or later self-fertilized generations of back-crossed derived material, and/or using wide crosses between distantly related species, such as interspecific and intergeneric hybrids resultant from crossing species or genera that do not normally sexually reproduce with each other (maize×wheat, maize×sorghum, maize×rice, etc.). The methods disclosed herein can be particularly useful for such breeding purposes.

Example 9

Creation of Paternal Gamete-Derived Doubled Haploids

Haploid microspores generated by any of the methods disclosed herein that are used to develop embryos are then contacted with an amount of a chromosome doubling agent to promote chromosome doubling and to regenerate homozygous diploid plants from the treated haploid microspore derived haploid embryos, embryo-like structures, or embryoids. The haploid microspore cells may be in contact with the doubling agent before, during, or after initiation of microspore embryogenesis, embryo maturation, or plant regeneration. Various compounds are known in the art to have chromosome doubling properties, including, but not limited to, those disclosed in Table 1.

For example, microspore-derived embryoids generated by any of the methods disclosed herein are transferred to a medium containing colchicine for approximately 24 hours and then transferred onto a medium without colchicine to achieve a population of doubled haploid embryos. After approximately 6-10 days plantlets are transferred to a light culture room. Approximately 7-14 days later, plantlets are transferred to flats containing potting soil and grown for 1 week in a growth chamber and subsequently grown an additional 1-2 weeks in a greenhouse, then transferred to pots and grown to maturity.

Example 10

Creation of a Maize Microspore Activator Strain with Embryogenesis Inducing Properties To improve embryogenesis inducing morphogenic developmental gene protein transport, translocation, and/or uptake by microspores expression cassettes, similar to those shown in FIG. 5A are constructed and are used in the methods of the present disclosure. For example, the WUSCHEL polynucleotide is replaced with a polynucleotide encoding the 36 amino acid C-terminal translocation signal of the *Agrobacterium tumefaciens* virF protein fused to the C-terminal end of a WUSCHEL polypeptide (SEQ ID NO: 13 and SEQ ID NO:14), a polynucleotide encoding the 127 amino acid C-terminal translocation signal of the *Agrobacterium tumefaciens* virF protein fused to the C-terminal end of a WUSCHEL polypeptide (SEQ ID NO: 15 and SEQ ID NO:16), a polynucleotide encoding the C-terminal 27 amino acids of the GALLS polypeptide from the root-inducing (Ri) plasmid of *Agrobacterium rhizogenes* fused to the C-terminal end of a WUSCHEL polypeptide (SEQ ID NO: 17 and SEQ ID NO:18), a polynucleotide encoding any of the WUSCHEL sequences described in this Example 10 or the WUSCHEL sequences described in Examples 3 and 4 in combination with a translational fusion protein comprising the Ms44 secretion signal peptide (SEQ ID NO:5), the ODP2 polypeptide (SEQ ID NO:20), and a C-terminal CPP polypeptide (any one of SEQ ID NO:22, SEQ ID NO:24, SEQ ID NO:26, SEQ ID NO:28, and SEQ ID NO:30), and a polynucleotide encoding a WUSCHEL polypeptide fused to a glucocorticoid receptor (GR) (SEQ ID NO: 48 and SEQ ID NO 49).

When the expression cassettes are used as described in Example 7, increased microspore embryogenesis in planta prior to microspore isolation is expected. These expression cassettes are expected to facilitate protein expression and transport of the embryogenesis inducing morphogenic developmental gene protein from the tapetum cells to the locule of the anther to induce cellular reprogramming and initiate microspore embryogenesis within the spatiotemporal localization of tapetum cells resulting in protein processing and secretion of the WUSCHEL embryogenesis modulation factor into the locule during microgametogenesis. In the case of the expression cassette encoding the WUSCHEL protein fused to a glucocorticoid receptor (GR) (SEQ ID NO: 48 and SEQ ID NO 49) it is expected that protein activity is conditionally localized to the nucleus by external application of animal hormone analogs into the in vitro tissue culture. Following this treatment, the activatable chimeric transcription factors provides a means for activating microspore embryogenesis for improved embryo regeneration and plant propagation.

A microspore activator hemizygous $T_0$ plant (comprising the expression cassettes described above in this Example 10) generated as in Example 7 is used as described in Example 8 to create a hemizygous $F_1$ hybrid and ultimately to create populations of paternal gamete-derived (androgenic) doubled haploids in maize. During microsporangium development, it is expected that the embryogenesis inducing WUSCHEL fusion polypeptide is delivered into the locule where all microspores are developing which allows all microspores to be treated with the embryogenesis inducing morphogenic developmental polypeptide in vivo which improves microspore embryogenesis response in vitro following microspore isolation. It is expected that microspores isolated from the hemizygous $F_1$ hybrid and subjected to standard tissue culture conditions (induction media without any embryogenesis inducing compounds) post isolation exhibit an increased generation of embryoids and/or an increased generation of embryo-like structures when compared to a Null or wild type $F_1$ hybrid microspores subjected to the same post isolation tissue culture conditions. Microspores isolated from the tassels of the hemizygous $F_1$ hybrids (which have undergone in planta cellular reprogramming and initiation of microspore embryogenesis within the locule during microgametogenesis) can be subjected to tissue culture methods including, but not limited to, further cellular reprogramming and embryogenesis induction methods as described herein. Further, using methods known in the art, wild-type microspore-derived embryos from the hemizygous $F_1$ hybrid can be genotyped and selected to create paternal gamete (androgenic) doubled haploid populations. Maintenance of a desired single-copy homozygous $T_1$ microspore activator event for use as the microspore activator parent can be performed by further propagation of selected, stable transgenic individuals, including methods to self-fertilize a homozygous transgenic line or by self-fertilization of a hemizygous line followed by selection of homozygous progeny. For some breeding purposes, it can be of particular interest to create segregating material from crosses including, but not limited to, $F_2$ or later filial generations derived from the hemizygous $F_1$ hybrid, from back-crossed material after a first or later generation and/or later self-fertilized generations of back-crossed derived material, and/or using wide crosses between distantly related species, such as interspecific and intergeneric hybrids resultant from crossing species or genera that do not normally sexually reproduce with each other (maize×wheat, maize×sorghum, maize×rice, etc.). The methods disclosed herein can be particularly useful for such breeding purposes.

When the sequences described above in this Example 10 are used as described in Examples 3-6 microspores so treated are expected to demonstrate improved microspore responsiveness and embryogenesis induction when compared to controls.

Example 11

Selection of Wild-Type Microspore Embryos from a Hemizygous to Transgenic F1 Hybrid A wild type inbred parent 1 is crossed with a wild type inbred parent 2 to provide $F_1$ zygotic embryos developing within the fertilized ear of the maternal parent. Each $F_1$ zygotic embryo has two sets of chromosomes, one from each parent. After fertilization, for example 8 to 16 days post-fertilization, immature $F_1$ zygotic embryos from the maternal ear are isolated for transformation purposes to integrate into the $F_1$ plant genome any of the expression cassettes described herein.

Figure 9:
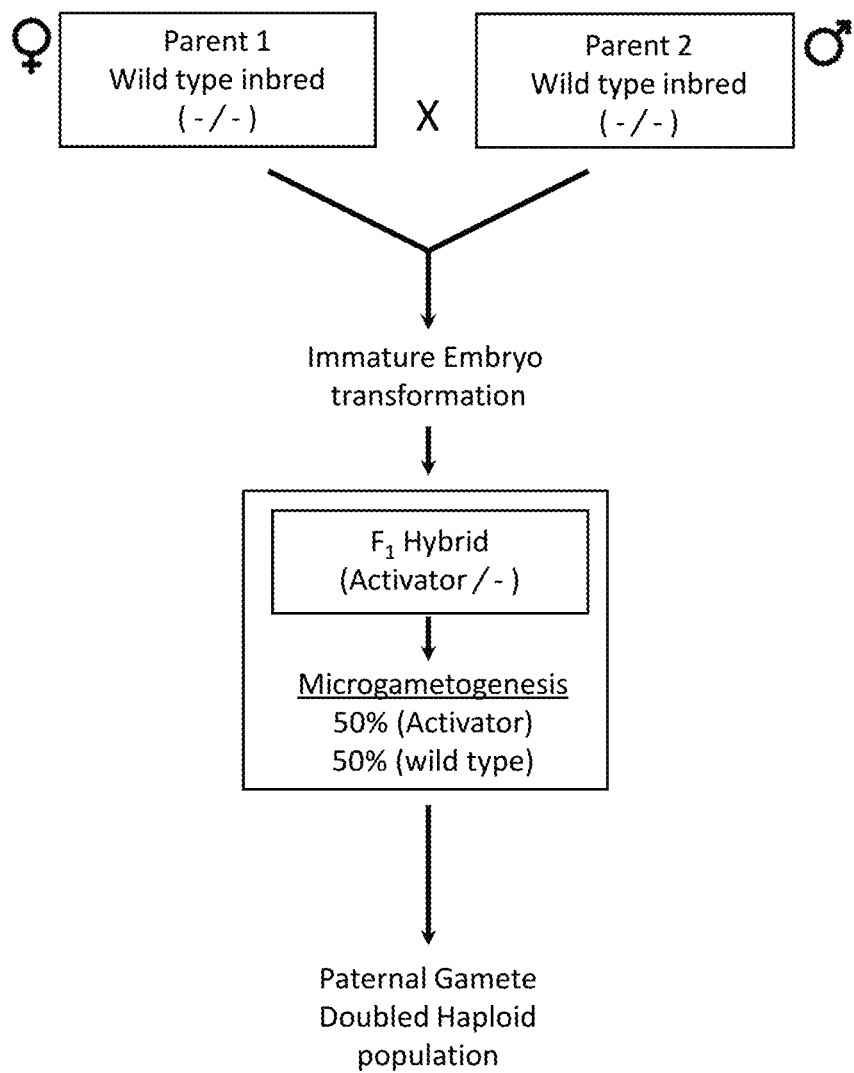
FIG. 9 is a schematic diagram depicting a method for selecting wild type microspore-derived embryos from a hemizygous Ms44-WUS microspore activator $T_0$ transgenic hybrid using an immature $F_1$ embryo explant for transformation.

Plants are selected having a single copy of the genetic construct comprising any of the expression cassettes described herein in a hemizygous state in which cellular reprogramming of developing microspores within the anthers occurs in planta (see FIG. 9).

The microspores segregate in a 1:1 ratio during gametogenesis resulting in half of the gametes being wild type and the other half of the gametes being transgenic (having inherited the transgenic locus). It is expected that the wild-type microspores will have improved embryogenesis responsiveness from a hemizygous $T_0$ generation $F_1$ hybrid to create doubled haploid populations (FIG. 9).

Example 12

Maize Maternal Haploid Inducer Line Transformation with Endosperm Activator Trait A construct (see FIG. 10) with three expression cassettes in operable linkage was used to create a stable maize endosperm activator line.

The first expression cassette comprised in operable linkage a polynucleotide sequence encoding the ZmBETL9 promoter and 5' untranslated region (SEQ ID NO: 33), the N-terminal ZmBETL9 basal endosperm transfer layer secretion signal peptide (SEQ ID NO: 31 and SEQ ID NO: 32), and the WUSCHEL peptide fused to the 127-amino acid C-terminal translocation signal of the *Agrobacterium tumefaciens* virF protein (SEQ ID NO:15 and SEQ ID NO:16) (alternatively, any of the WUSCHEL variant translational fusions described herein can be used and operably linked to a promoter expressed in the basal endosperm transfer layer). The second expression cassette comprised in operable linkage a polynucleotide sequence encoding the ZmBETL9-like promoter and 5' untranslated region (SEQ ID NO: 36), the N-terminal ZmBETL9-like basal endosperm transfer layer secretion signal peptide (SEQ ID NO: 34 and SEQ ID NO: 35), the 445-amino acid C-terminal ODP2 peptide, the GALLS$^{C27}$ peptide, a minimal FLAG epitope (SEQ ID NO:37 and SEQ ID NO:38), and the KNOTTED1 cell penetrating peptide (SEQ ID NO:21 and SEQ ID NO:22) (alternatively any of the ODP2 variant translational fusions described herein can be used and operably linked to a promoter expressed in the basal endosperm transfer layer).

The third expression cassette, used to verify paternal allele expression in endosperm cells, comprised in operable linkage a polynucleotide sequence encoding the *Anemonia*

Figure 10:
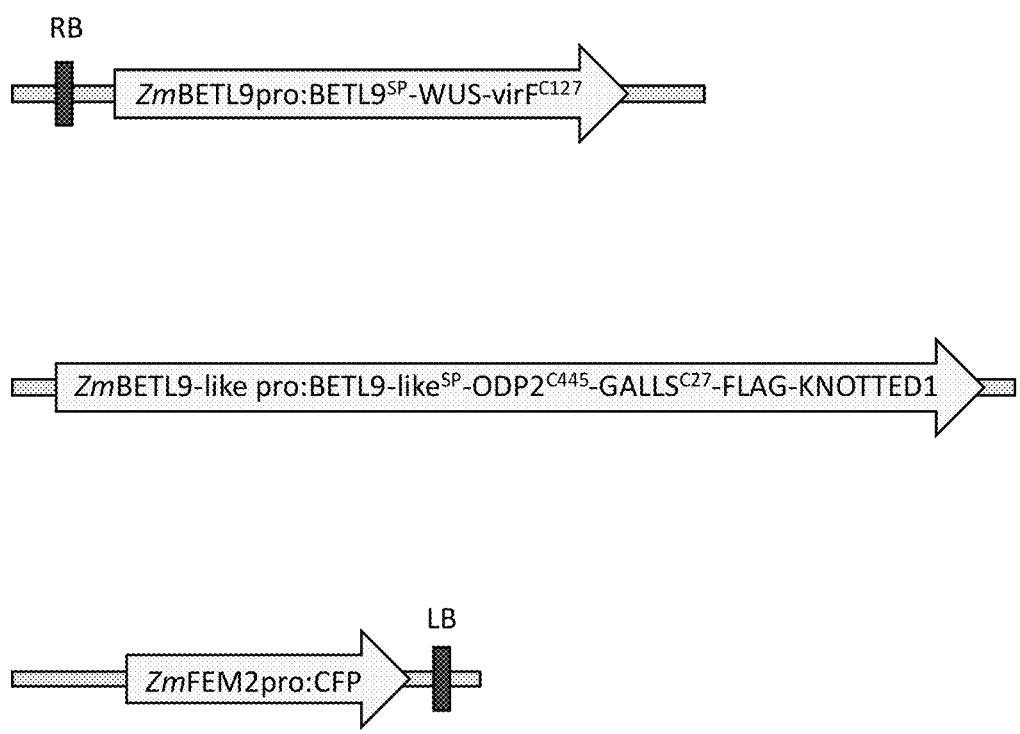
FIG. 10 is a schematic diagram showing a construct with three expression cassettes useful for creating a stable maize endosperm activator strain.

*majano* Cyan Fluorescent Protein (CFP) operably linked to the ZmFEM2 promoter (SEQ ID NO: 39). (FIG. 10).

Figure 11:
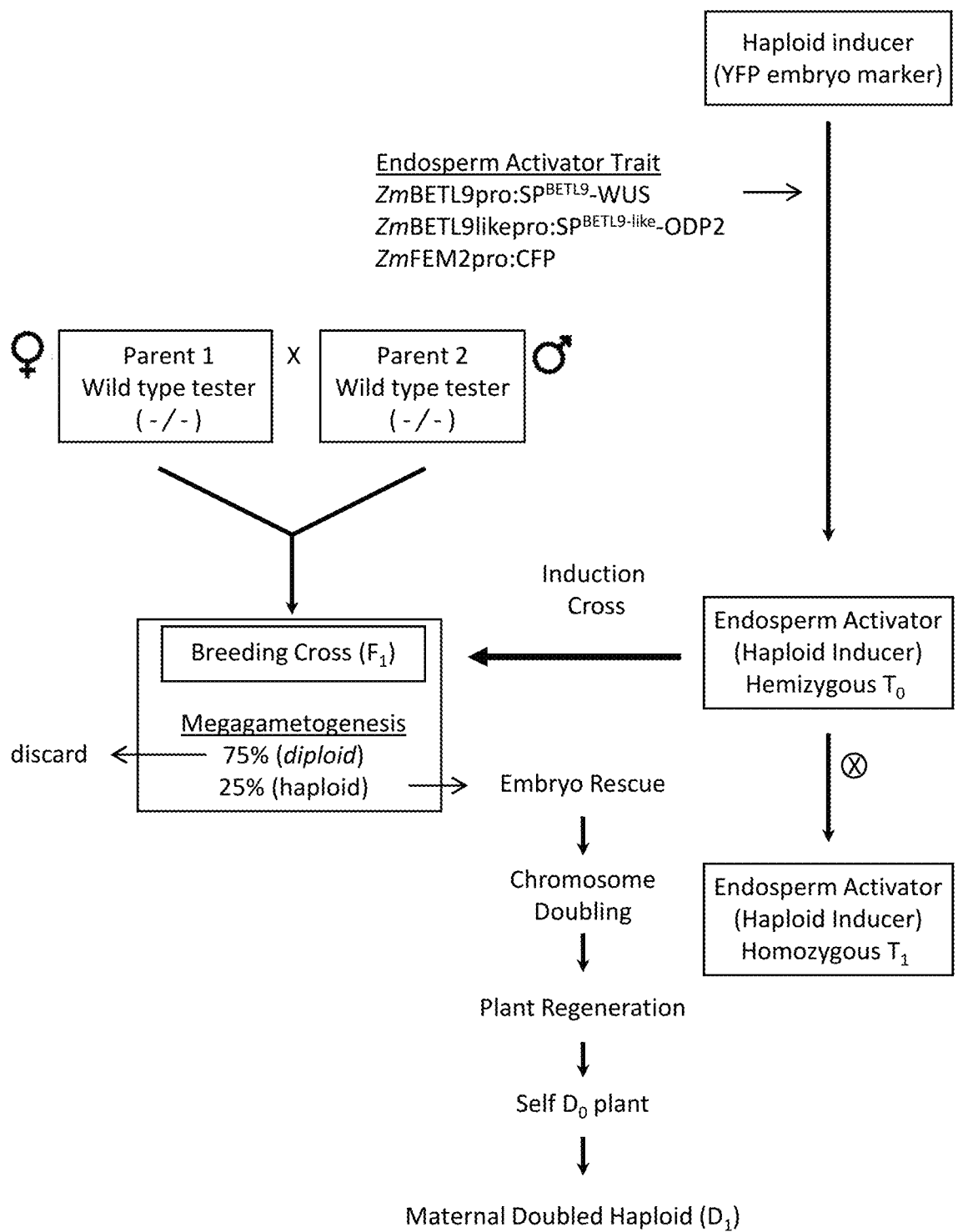
FIG. 11 is a schematic diagram depicting a method for selecting wild type $F_{1:2}$ derived maternal haploids resultant from an induction cross using a hemizygous endosperm activator line to improve maternal doubled haploid production.

Immature, diploid embryo explants isolated from developing maize kernels 12-14 days post self-fertilization of a maize haploid inducer line were transformed with the endosperm activator trait construct (see FIG. 10 and FIG. 11) by *Agrobacterium*-mediated transformation. The inducer line expresses a R-scm2 color marker in diploid embryos based on a paternal genome contribution to the embryo (Kato A. (2002) Plant breeding 121:370-377 and U.S. Patent Application 20030005479 incorporated herein by reference in its entirety). The embryo color marker was useful for identifying maternal haploid embryos that do not express the R-scm2 morphological marker due to the absence of the paternal genome in the haploid embryo. Additionally, this inducer line was previously stably transformed with an expression cassette comprising a polynucleotide encoding a maize ubiquitin promoter operably linked to a yellow fluorescent protein (YFP) which permits the discernment of diploid embryos with a paternal genome contribution from the maternal haploid embryos based on detecting the presence and absence of expression of the YFP protein, respectively.

*Agrobacterium*-mediated transformation of the inducer created a transgenic maize endosperm activator haploid inducer hemizygous $T_0$ line (FIG. 11) expressing two embryogenesis inducing morphogenic developmental fusion proteins with N-terminus secretion signal peptides, each under the regulation of an endosperm promoter (these fusion proteins were expressed in the triploid endosperm cells, more specifically in the basal endosperm transfer layer cells, which allowed protein translocation and cellular reprogramming in the maternal haploid embryos and improved the creation of maternally-derived maize haploid plants.

Example 13

Improved Plantlet Regeneration of Double Haploid Maize Plants Using a Maize Maternal Haploid Inducer Endosperm Activator Two parental lines, Parent 1 wild type tester and Parent 2 wild type tester, were selected, crossed, and the resultant breeding cross $F_1$ seeds then were planted and grown and the female flower, or ear of these breeding cross $F_1$ plants was used for fertilization (pollen receiver). Seeds from the transgenic maize endosperm activator haploid inducer hemizygous $T_0$ line generated in Example 12 were planted and grown and the male flower, or tassel of these transgenic maize endosperm activator haploid inducer hemizygous $T_0$ plants was used for fertilization (pollen donor) (see FIG. 11). An induction cross was performed namely, the ears of the pollen receiver were shoot-bagged before silk emergence and the silks of the ears of these pollen receivers were pollinated with pollen grains collected from the anthers of the pollen donor plants (see FIG. 11). This induction cross employed methods regularly used in maize breeding programs to avoid any foreign pollen contamination.

This induction cross pollination method results in the production of haploid embryos in each ear at a frequency ranging between 25% to approximately 50%. At approximately 9-16 days after pollination, the immature ears were harvested. The immature ears were surface sterilized in 30% Clorox bleach plus 0.5% Micro detergent for 20 minutes, and rinsed two times with sterile water and immature embryos from within the developing kernels were dissected and placed onto a plant tissue culture medium under asceptic conditions. Using methods known in the art, the plant tissue culture medium can be supplemented with a chromosome doubling agent (see Table 1) to generate maize doubled haploids.

Plants fertilized in induction crosses develop both diploid embryos and haploid embryos and all endosperm tissues are triploid with 3 sets of chromosomes in endosperm cells, two of the chromosomes are from the pollen receiver and one of the chromosomes is from the pollen donor. This induction cross allowed a direct comparison between the presence and the absence of the paternal allele expressing the endosperm activator trait, as detected by presence or absence of the ZmFEM2:CFP endosperm color marker, respectively.

After scoring endosperm for wild type endosperm or endosperm having the endosperm activator trait as described above, haploid embryos were rescued and isolated within the two endosperm classes and diploid and haploid embryos were then sorted by determining marker gene products inherited from the inducer line. Paternal contribution to the embryo was detectable by YFP expression thereby detecting diploid embryos expressing the paternal allele, whereas haploid embryos were colorless and observed as YFP negative.

The two classes of haploid maize embryos, those isolated from wild type endosperm (CFP negative endosperm) and those isolated after in planta contact with morphological developmental proteins derived from the endosperm activator trait (CFP positive endosperm) were isolated using a scalpel and placed on a medium containing colchicine. After approximately 24 hours the embryos were transferred onto a medium without colchicine and placed in the dark. After approximately 6-10 days plantlets were transferred to a light culture room. Approximately 7-14 days later, plantlets are transferred to flats containing potting soil and grown for 1 week in a growth chamber, are subsequently grown an additional 1-2 weeks in a greenhouse, and then are transferred to pots and grown to maturity. These plants are a heterogeneous population of doubled haploid plants. These fertile doubled haploid maize plants are selfed and evaluated for breeding purposes.

Haploid embryos that developed from in planta contact with embryogenesis inducing morphogenic developmental gene proteins which were transported to the embryo from the endosperm transfer cells and were treated with a chromosome doubling agent are expected to have increased levels plantlet regeneration relative to haploid embryos generated using conventional (wild type) haploid inducer lines.

Figure 12A:
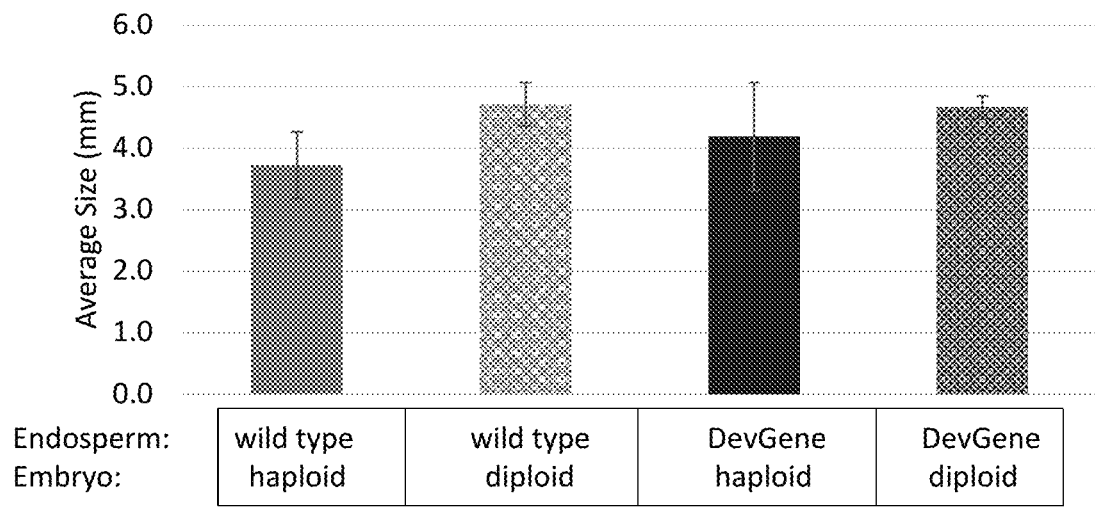
FIG. 12A is a bar graph showing embryos $F_{1:2}$ resultant from a haploid induction cross using a hemizygous haploid inducer line. The average haploid embryo size (millimeters (mm); y axis) were determined for CFP-minus and CFP-positive endosperm (wild type and morphological developmental gene, "DevGene", classes, respectively) for each haploid and diploid embryo, respectively.

For plants fertilized in induction crosses, diploid embryos were equal in average embryo size independent of endosperm activity. The average size of the rescued embryos that developed in planta in the presence of morphological developmental gene proteins had increased haploid embryo sizes in comparison to the haploid embryos with a wild type endosperm (FIG. 12A). These results demonstrated that in planta contact of a plant cell derived from a maternal haploid embryo with an embryogenesis inducing morphogenic developmental translational fusion protein derived from the endosperm activator trait improved haploid embryo development.

Figure 12B:
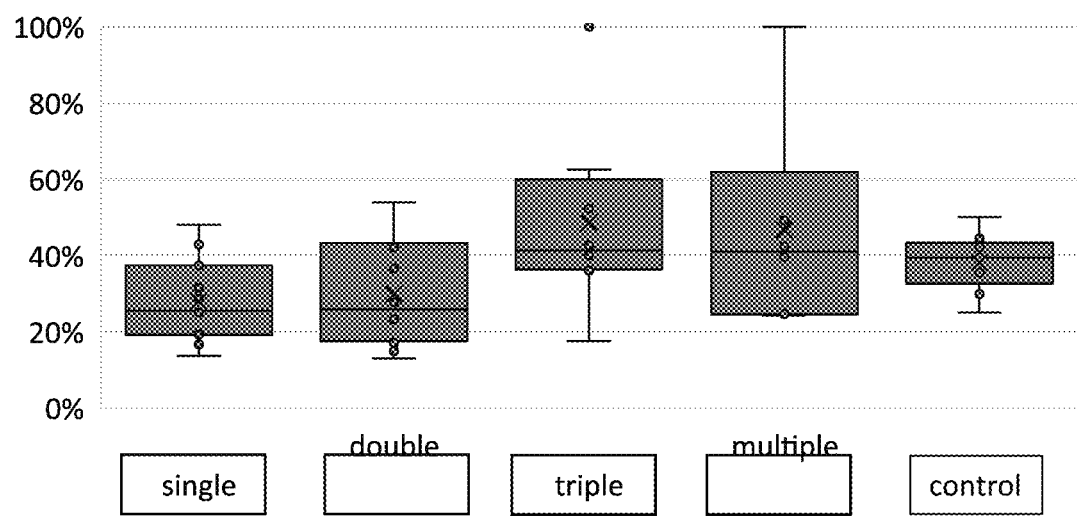
FIG. 12B is a bar graph showing the percent of germinated haploid embryos (y axis) per haploid induction cross using transgenic lines with varying copy number of the endosperm activator trait (x axis).

Rescued embryos that were colchicine-treated and then transferred to a light culture room, were each scored for an assessment of haploid plant regeneration in response to in planta developmental gene expression in the endosperm. The regeneration of haploid plants had a positive correlation in response to the copy number abundance of the transgene encoding the endosperm activator trait, and thus the protein dosage, in the paternal haploid inducer line (FIG. 12B). Increased levels of WUSCHEL and ODP2 fusion proteins in the endosperm positively impacted plantlets regenerated from haploid embryos during in vitro culture under light conditions, and when practiced in combination with a chromosome doubling treatment will improve productivity for creating doubled haploids maize plants using a maternal (gynogenic) system.

Example 14

Figure 13:
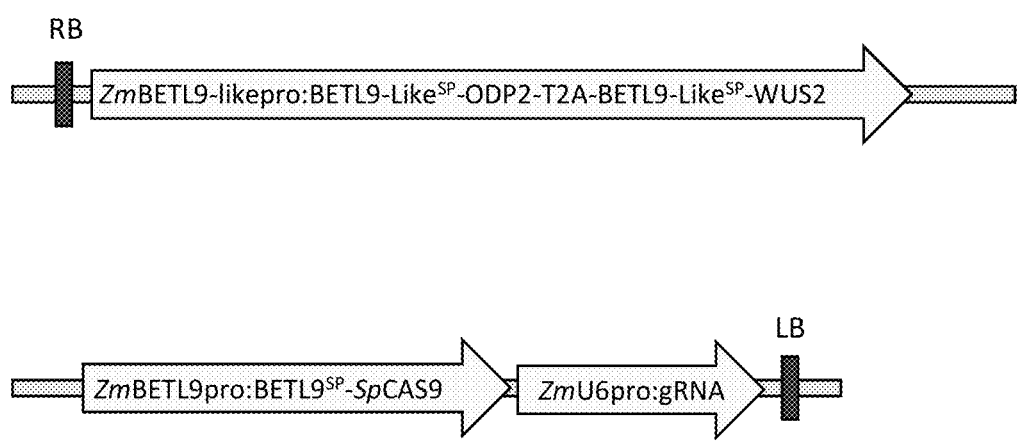
FIG. 13 is a schematic diagram of a construct useful for creating a stable maize endosperm activator strain with gene editing activity.
Figure 14:
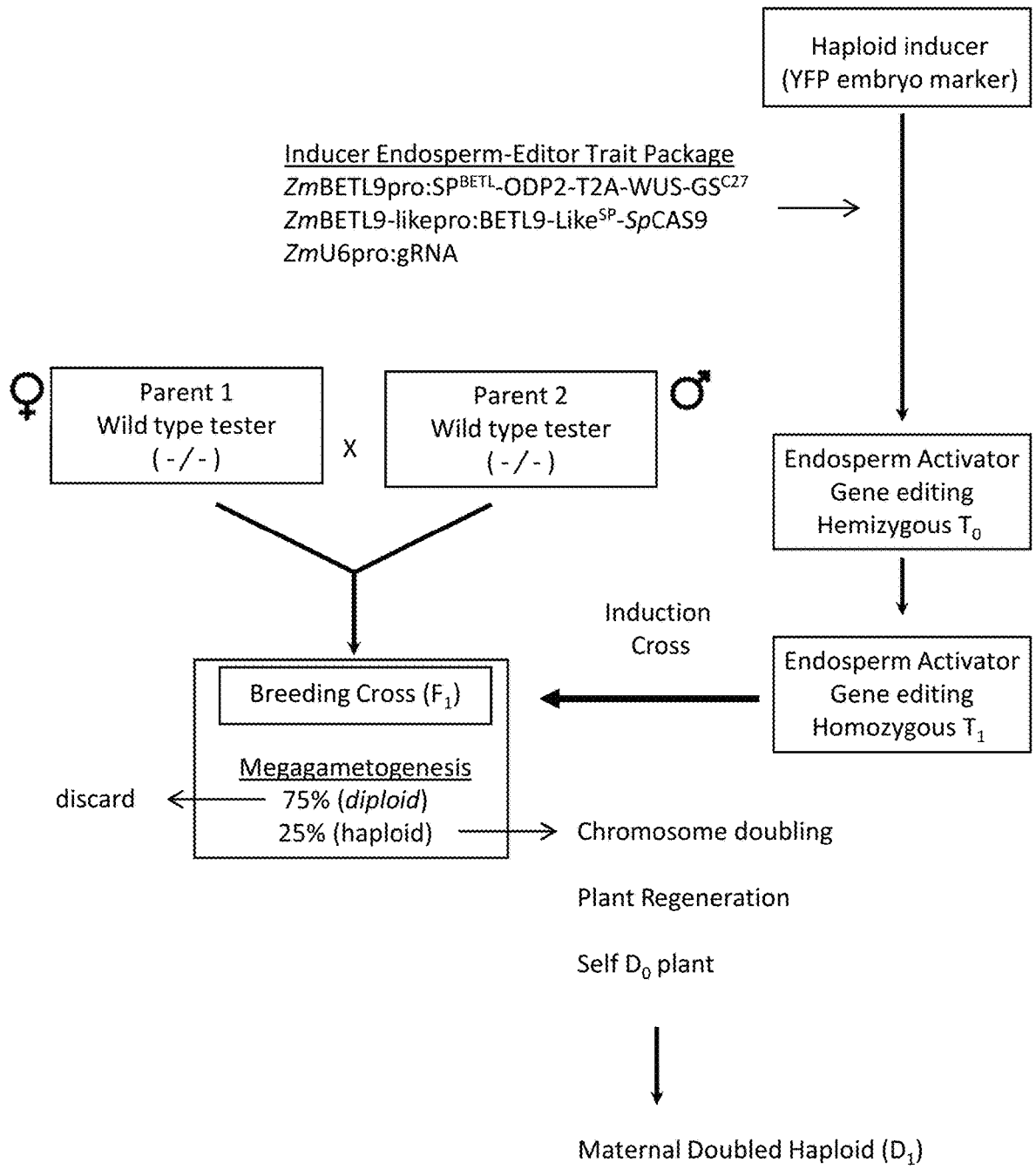
FIG. 14 is a schematic diagram depicting a method for selecting wild type $F_{1:2}$ derived maternal haploids resultant from an induction cross using a hemizygous endosperm activator line in combination with CAS9 delivery from the endosperm to maternal haploid embryos to improve maternal doubled haploid production of gene-edited progeny.

Maize Maternal Haploid Inducer Line Transformation with Endosperm Activator-Editor Traits Constructs (see FIG. 13A and FIG. 13B) with expression cassettes in operable linkage are used to create a stable maize endosperm activator line used in methods to facilitate selecting wild type $F_{1:2}$ derived maternal haploids resultant from an induction cross using an "endosperm activator" line in combination with nuclease protein delivery method to improve maternal doubled haploid production of gene-edited progeny (see FIG. 14).

The first construct comprises an expression cassette comprising a polynucleotide sequence encoding in operable linkage the ZmBETL9-like promoter and 5' untranslated region (SEQ ID NO: 36), the N-terminal ZmBETL9-like basal endosperm transfer layer secretion signal peptide (SEQ ID NO: 34 and SEQ ID NO: 35), the ODP2 peptide (SEQ ID NO: 19 and SEQ ID NO: 20), the *Thosea asigna* polycistronic-like T2A linker (SEQ ID NO: 40 and SEQ ID NO:41) (mediates a ribosome-skipping event enabling generation of multiple, separate peptide products from one mRNA), the N-terminal ZmBETL9-like basal endosperm transfer layer secretion signal peptide (SEQ ID NO: 34 and SEQ ID NO: 35), and the WUSCHEL peptide (SEQ ID NO: 6 and SEQ ID NO: 7). (alternatively, any of the WUSCHEL and/or ODP2 variant translational fusions described herein can be used and operably linked to a promoter expressed in the basal endosperm transfer layer).

The same expression cassette or a second construct comprises in operable linkage, comprising a polynucleotide sequence encoding the BETL9 promoter and 5' UTR (SEQ ID NO: 33), the N-terminal ZmBETL9 basal endosperm transfer layer secretion signal peptide (SEQ ID NO: 31 and SEQ ID NO: 32), and the *Streptococcus pyogenes* Cas9 (SpCAS9 MO) (SEQ ID NO: 42 and SEQ ID NO: 43) (alternatively, any of the gene editing nucleases described herein can be used and operably linked to a promoter expressed in the basal endosperm transfer layer). Further, the *Thosea asigna* polycistronic-like T2A linker (SEQ ID NO: 40 and SEQ ID NO:41) which mediates a ribosome-skipping event enabling generation of multiple, separate peptide products from one mRNA can be used to combine two or more gene editing components in the second construct.

In a particular configuration, the second expression cassette of the second construct is designed to transcribe a guide RNA molecule in operable linkage with a regulatory element (see Svitashev et al., Plant Physiol (2015) 169:931-45 (use of the ZmU6 promoter with various guide RNAs). Guide RNAs are designed depending on the gene editing target. Alternatively, other promoters are used in operably linkage with the guide RNA, for example an endosperm preferred promoter. Further, a synthetic guide RNA molecule, or combination of synthetic guide RNA molecules, can be exogenously delivered using methods known in the art, including, but not limited to, biolistic delivery, electroporation, or *Agrobacterium*-mediated delivery into cells with a pre-integrated gene editing trait as previously described by Svitashev et al., (2015). In another option, the guide RNA need not be expressed from an expression cassette and can be delivered exogenously, for example, in the culturing media. Similarly, the ribounucleoprotein ("RNP") complex comprising the guide RNA and the Cas endonuclease can be delivered through an exogenous application to the embryogenic maternal haploid embryos. Such delivery of RNP directly to the embryogenic maternal haploid embryos need not involve a transformation step.

Immature, diploid embryo explants are isolated from developing maize kernels 12-14 days post self-fertilization of a maize haploid inducer are transformed with the endosperm activator trait package construct (see FIG. 13 and FIG. 14) by *Agrobacterium*-mediated transformation. The inducer line expresses a R-scm2 color marker in diploid embryos based on a paternal genome contribution to the embryo (Kato A. (2002) Plant breeding 121:370-377 and U.S. Patent Application 20030005479 incorporated herein by reference in its entirety). The embryo color marker is useful for identifying maternal haploid embryos that do not express the R-scm2 morphological marker due to the absence of the paternal genome in the haploid embryo. Additionally, this inducer line was previously stably transformed with an expression cassette comprising a polynucleotide encoding a maize ubiquitin promoter operably linked to a yellow fluorescent protein (YFP) which permits the discernment of diploid embryos with a paternal genome contribution from the maternal haploid embryos based on detecting the presence and absence of expression of the YFP protein, respectively.

*Agrobacterium*-mediated transformation of the inducer creates a transgenic maize endosperm activator gene editing hemizygous $T_0$ line (FIG. 14) expressing two embryogenesis inducing morphogenic developmental fusion proteins with N-terminus secretion signal peptides, each under the regulation of an endosperm promoter (these fusion proteins are expressed in the triploid endosperm cells, more specifically in the basal endosperm transfer layer cells, which allows protein translocation and cellular reprogramming in the maternal haploid embryos and improves the creation of maternally-derived maize haploid plants.

Example 15

Improved Plantlet Regeneration of Genome Edited, Double Haploid Maize Plants Using a Maize Maternal Haploid Inducer with Endosperm Activator-Embryo Editor Traits Two parental lines, Parent 1 wild type tester and Parent 2 wild type tester, are selected, crossed, and the resultant breeding cross $F_1$ seeds then are planted and grown and the female flower, or ear of these breeding cross $F_1$ plants is used for fertilization (pollen receiver). An endosperm activator gene editing homozygous $T_1$ line is generated employing methods regularly used in maize breeding programs from the transgenic maize endosperm activator gene editing hemizygous $T_0$ line generated in Example 14. Seeds from this transgenic maize endosperm activator gene editing homozygous $T_1$ line are planted and grown and the male flower, or tassel of these transgenic maize endosperm activator gene editing homozygous $T_1$ plants are used for fertilization (pollen donor) (see FIG. 14). An induction cross is performed namely, the ears of the pollen receiver are shoot-bagged before silk emergence and the silks of the ears of these pollen receivers are pollinated with pollen grains collected from the anthers of the pollen donor plants (see FIG. 14). This induction cross employs methods regularly used in maize breeding programs to avoid any foreign pollen contamination. Alternatively, the induction cross can be performed using the transgenic maize endosperm activator gene editing hemizygous $T_0$ line as the pollen donor.

It is expected that this induction cross pollination method will result in the production of haploid embryos in each ear at a frequency ranging between 25% to approximately 50%. At approximately 9-16 days after pollination, the immature ears are harvested. The immature ears are surface sterilized in 30% Clorox bleach plus 0.5% Micro detergent for 20 minutes, and rinsed two times with sterile water and immature embryos from within the developing kernels are dissected and placed onto a plant tissue culture medium under aseptic conditions. Using methods known in the art, the plant tissue culture medium is supplemented with a chromosome doubling agent (see Table 1) to generate maize doubled haploids.

Plants fertilized in induction crosses develop both diploid embryos and haploid embryos and all endosperm tissues are triploid with 3 sets of chromosomes in endosperm cells, two of the chromosomes are from the pollen receiver and one of the chromosomes is from the pollen donor. This induction cross allows a direct comparison between the presence and the absence of the paternal allele expressing the endosperm activator trait, as detected by presence or absence of the ZmFEM2:CFP endosperm color marker, respectively.

After scoring endosperm for wild type endosperm or endosperm having the endosperm activator trait as described above, haploid embryos are rescued and isolated within the two endosperm classes and diploid and haploid embryos are then sorted by determining marker gene products inherited from the inducer line. Paternal contribution to the embryo is detectable by YFP expression thereby detecting diploid embryos expressing the paternal allele, whereas haploid embryos were colorless and observed as YFP negative.

The two classes of haploid maize embryos, those isolated from wild type endosperm (CFP negative endosperm) and those isolated after in planta contact with morphological developmental proteins derived from the endosperm activator trait (CFP positive endosperm) are isolated using a scalpel and placed on a medium containing colchicine. After approximately 24 hours the embryos are transferred onto a medium without colchicine and placed in the dark. After approximately 6-10 days plantlets are transferred to a light culture room. Approximately 7-14 days later, plantlets are transferred to flats containing potting soil and grown for 1 week in a growth chamber, are subsequently grown an additional 1-2 weeks in a greenhouse, and then are transferred to pots and grown to maturity. These plants are a heterogeneous population of doubled haploid plants. These fertile doubled haploid maize plants are selfed and evaluated for breeding purposes.

It is expected that the haploid embryos that developed from in planta contact with embryogenesis inducing morphogenic developmental gene proteins and the gene editing machinery which were transported to the embryo from the endosperm transfer cells and were treated with a chromosome doubling agent will have increased levels genome edited plantlet regeneration relative to haploid embryos generated using conventional (wild type) haploid inducer lines.

For plants fertilized in induction crosses, it is expected that diploid embryos will be equal in average embryo size independent of endosperm activity. The average size of the rescued embryos that developed in planta in the presence of morphological developmental gene proteins have increased haploid embryo sizes in comparison to the haploid embryos with a wild type endosperm. These results demonstrate that in planta contact of a plant cell derived from a maternal haploid embryo with an embryogenesis inducing morphogenic developmental translational fusion protein derived from the endosperm activator trait improve haploid embryo development in planta.

Rescued embryos that are colchicine-treated and then transferred to a light culture room, are each scored for an assessment of haploid plant regeneration in response to in planta developmental gene expression in the endosperm. The regeneration of haploid plants has a positive correlation in response to the copy number abundance of the transgene encoding the endosperm activator trait, and thus the protein dosage, in the paternal haploid inducer line. Increased levels of WUSCHEL and ODP2 fusion proteins in the endosperm positively impact plantlets regenerated from haploid embryos, and when practiced in combination with a chromosome doubling treatment demonstrate an improved productivity for creating doubled haploids maize plants using a maternal (gynogenic) system.

Example 16

Creation of a Maize Microspore Activator-Editor Line and Transformation with Same Provides Improved Plantlet Regeneration of Genome Edited Plants Constructs with expression cassettes in operable linkage are designed to increase microspore embryogenesis and provide gene editing in planta prior to microspore isolation. Genome editing is also performed during the microspore embryogenesis induction phase through the selective presence of a site-specific nuclease, e.g., Cas endonuclease in the target cell of interest.

In one example, the first construct comprises an expression cassette comprising in operable linkage a polynucleotide encoding a tapetum cell preferred regulatory element, a tapetum cell signal peptide sequence fused to anembryogenesis inducing morphogenic developmental gene sequence with a linker sequence and the fluorescent protein gene.

In one example, the second construct comprises a tapetum cell preferred regulatory element, a tapetum cell signal peptide sequence, a Cas9, and a polycistronic-like linker which mediates a ribosome-skipping event enabling generation of multiple, separate peptide products from one mRNA is used to combine two or more gene editing components in the second construct. The second expression element of the second construct comprises in operable linkage a regulatory element and a guide RNA molecule designed to transcribe the guide RNA molecule in operable linkage with the regulatory element. These constructs are expected to facilitated protein expression and transport of the embryogenesis inducing morphogenic developmental gene protein and gene editing components from the tapetum cells to the locule of the anther inducing cellular reprogramming, initiating microspore embryogenesis within the spatiotemporal localization of tapetum cells resulting in protein processing and secretion of the embryogenesis modulation factor and the gene editing components into the locule during microgametogenesis. In another option, the guide RNA need not be expressed from an expression cassette and can be delivered exogenously, for example, in the culturing media. Similarly, the ribounucleoprotein ("RNP") complex comprising the guide RNA and the Cas endonuclease can be delivered through an exogenous application to the embryogenic microspores. Such delivery of RNP directly to the embryogenic microspores need not involve a transformation step.

In an aspect, the constructs are incorporated into an *Agrobacterium* transformation vector. *Agrobacterium* transformation is preformed using standard protocols known in the art. Alternatively, transformation vectors can be introduced to plant cells by biolistic transformation methods, which are also known in the art.

Following transformation, a microspore activator-editor hemizygous $T_0$ plant is regenerated, self-pollinated and the genotypes are sorted. A single-copy homozygous $T_1$ microspore activator-editor event is selected. Genetic crosses are made between the single-copy event, homozygous $T_1$ microspore activator-editor and a parent 2 wild type inbred to create a hemizygous $F_1$ hybrid (see FIG. 7) and ultimately to create populations of paternal gamete-derived gene-edited (androgenic) doubled haploids in maize. Alternatively, a single copy hemizygous $T_0$ microspore activator-editor event is crossed with a parent 2 wild type inbred to create a hemizygous $F_1$ hybrid. Similarly, a single copy hemizygous $T_1$ microspore activator-editor event is crossed with a parent 2 wild type inbred to create a hemizygous $F_1$ hybrid.

Upon growth of the hemizygous $F_1$ hybrids, microgametogenesis occurs in the reproductive tissues and the transgene insertion site segregates in a Mendelian fashion. Independently of gametogenesis, the diploid sporophytic tapetum cells transformed with a single copy of the heterologous expression cassette encoding the embryogenesis inducing morphogenic developmental gene polypeptide and the genome editing components (e.g., Cas9 nuclease, guide RNA and optionally a donor DNA template for repair or for insertion) in a hemizygous state expresses and secretes the embryogenesis inducing morphogenic developmental polypeptide and the gene editing components within one or more tapetum cells. During microsporangium development the embryogenesis inducing morphogenic developmental polypeptide and the gene editing components are delivered/secreted/transported into the locule where a population of microspores are developing which allows all microspores to be treated with the embryogenesis inducing morphogenic developmental polypeptide and the gene editing components in vivo which provides gene-edited microspores and improves microspore embryogenesis response in vitro following microspore isolation. Thus, induction of embryogenesis of microspores along with performing genome editing reactions increase the overall efficiency and effectiveness of generating several genome-edited, double-haploid plants for breeding purposes.

Microspores isolated from the tassels of the hemizygous $F_1$ hybrids (which have undergone in planta gene-editing, cellular reprogramming and initiation of microspore embryogenesis within the locule during microgametogenesis) can be subjected to tissue culture methods including, but not limited to, further cellular reprogramming and embryogenesis induction methods as described herein.

Using methods known in the art, wild-type microspore-derived embryos from the hemizygous $F_1$ hybrid can be genotyped and selected to create paternal gamete (androgenic) doubled haploid populations.

Maintenance of the desired single-copy homozygous $T_1$ microspore activator-editor event for use as the microspore activator-editor parent can be performed by further propagation of selected, stable transgenic individuals, including methods to self-fertilize a homozygous transgenic line or by self-fertilization of a hemizygous line followed by selection of homozygous progeny.

For some breeding purposes, it can be of particular interest to create segregating material from crosses including, but not limited to, $F_2$ or later filial generations derived from the hemizygous $F_1$ hybrid, from back-crossed material after a first or later generation and/or later self-fertilized generations of back-crossed derived material, and/or using wide crosses between distantly related species, such as interspecific and intergeneric hybrids resultant from crossing species or genera that do not normally sexually reproduce with each other (maize×wheat, maize×sorghum, maize×rice, etc.). The methods disclosed herein can be particularly useful for such breeding purposes.

Although the foregoing disclosure has been described in some detail by way of illustration and example for purposes of clarity of understanding, certain changes and modifications may be practiced within the scope of the appended claims.

That which is claimed:

1. A method of generating a haploid plant embryo comprising:
   (a) providing a plant microspore with an embryogenesis inducing compound to promote microspore embryogenesis in the plant microspore, wherein the embryogenesis inducing compound is hemin or a kinase inhibitor selected from N-[(2R)-2,3-dihydroxypropoxy]-3,4-difluoro-2-(2-fluoro-4-iodoanilino)benzamide, anthra(1,9-cd)pyrazol-6(2H)-one:4-(4-Fluorophenyl)-2-(4-methylsulfinylphenyl)-5-(4-pyridyl)1H-imidazole, or N-benzyl-2-(pyrimidin-4-ylamino)-1,3-thiazole-4-carboxamide;
   (b) isolating an embryogenic microspore from the plant microspore; and
   (c) culturing the embryogenic microspore to generate the haploid plant embryo.

2. The method of claim 1, wherein the embryogenesis inducing compound is present in a tissue culture media.

3. The method of claim 1, further comprising culturing the haploid plant embryo.

4. The method of claim 3, comprising contacting the haploid plant embryo with a chromosome doubling agent for a period sufficient to generate a doubled haploid plant embryo.

5. The method of claim 1, wherein the plant microspore is obtained from maize, rice, sorghum, *brassica*, soybean, wheat, or cotton.

* * * * *

SEQUENCE LISTING

```
<160> NUMBER OF SEQ ID NOS: 49

<210> SEQ ID NO 1
<211> LENGTH: 927
<212> TYPE: DNA
<213> ORGANISM: artificial sequence
<220> FEATURE:
<223> OTHER INFORMATION: synthetic

<400> SEQUENCE: 1
atggctgcta acgccggcgg cggaggagcc ggaggcggaa gtggcagtgg ctcggttgcc      60
gcgcctgccg tatgtaggcc tagtggttcc agatggactc caacacctga gcagatacgc     120
atgctcaagg aactttacta cggttgtggt atccgctcgc cttctagtga acagattcaa     180
cgcataacag cgatgttgcg tcagcacggc aaaatcgaag gcaaaaacgt attttactgg     240
tttcaaaatc ataaagcccg cgagcgtcaa aagaggagac tcacgagttt ggacgtgaac     300
gtacctgctg ccggagctgc cgacgccacc acgtcccaac ttggagttct gagtcttagc     360
```

-continued

```
tccccgccgc cttccggagc cgccccaccg agtcccactc ttggatttta tgccgctgga    420
aatggaggag gttccgccgt gcttttggac acttcgtctg attggggttc cagcggcgct    480
gcaatggcga ctgagacttg tttccttcag gactatatgg gtgtcaccga tacgggaagt    540
tcatcacaat ggcccaggtt ttcaagtagt gacactataa tggctgcggc tgccgcgaga    600
gcagctacga ccagggcacc cgagacactg cctctcttcc caacttgcgg tgacgacggc    660
ggctccggtt cctcgagtta tttgcctttc tggggcgcgg cctccacaac agcaggcgcg    720
acaagttccg ttgcaatcca gcagcaacat caacttcagg agcagtatag ttttactcc    780 aatagtaact ccacccaact cgcgggcacg ggcaaccaag acgtgagtgc gacagcagcg    840
gcagcagcgg ctttggagct gagtctgtct tcgtggtgct ctccctatcc agcggcaggt    900
tcaatgggac atcatcacca ccaccat                                        927
```

<210> SEQ ID NO 2
<211> LENGTH: 309
<212> TYPE: PRT
<213> ORGANISM: artificial sequence
<220> FEATURE:
<223> OTHER INFORMATION: synthetic

<400> SEQUENCE: 2

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Pro Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Asp Gly Ser Gly Ser
    210                 215                 220

Ser Ser Tyr Leu Pro Phe Trp Gly Ala Ala Ser Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn

```
            260                 265                 270
Gln Asp Val Ser Ala Thr Ala Ala Ala Ala Ala Leu Glu Leu Ser
                275                 280                 285

Leu Ser Ser Trp Cys Ser Pro Tyr Pro Ala Ala Gly Ser Met Gly His
            290                 295                 300

His His His His His
305

<210> SEQ ID NO 3
<211> LENGTH: 1221
<212> TYPE: DNA
<213> ORGANISM: Zea mays

<400> SEQUENCE: 3
aattcgccct tgttgttgc tcatcggtcg tcggactctt aatagccggc tttaggatat      60
tgtccgggga gatatcggtg tgatctttag aaccggccat tgatggcct gagttttagt    120 agatctagac acatttcccc aacggagtcg ccaaaaagtg tgttggcgcc gatccaggcg    180
cgaaacactg gagatggacc gtttggcggt gttctctgcg gaggtgagga cggtccgcga    240
cctggcgcag cagcgactct cctctacgtg tgtccgacg tccgcgtct ggggctcgga    300 cggtccgcga tggcgcagag ggtcttcttc ttcgcagccg acctagatct cgcctcccgg    360
gagggacccc gtcggggagg agagattgta gggtgtgtct tggcgtcgac aggccacaca    420
atacgcctct agtcgacgta gagccgaaga gaggtgaagg attgaggtag aaggaggcta    480
aacttgggct aaactagaac tactgctaat gcataaggta aaacgagaa gtggacttca    540 tttgatcgat tgtggaaggt ttaatcgact gtagccctt atctatataa aggggaggta    600
tggacccgtt acaagcygtt tcccgagcta atctcacggt tttagttaat aaatcctgcg    660
agaaactcgg aactctaact gattctactc atgcgcgaac cattcgtgcc gccaccgctg    720
cccgtccggc tacgctcagt taaccctgtg ttgtgcgctg tgatttggtg gcatataaaa    780
ccacatttgc aataaaaatt tgtagggatt taacatacca agtgctgcgg aaaggaatcg    840
ttttcggagg acccaaaatt aaagaggcag atgctagagc tcgtccagct cagcgctgag    900
cacctgtgtt gtcttcctcg tccacgccgg cggagatgaa cggcaacaaa ggcggaaagg    960
ccgagacgct gagctcaagg acgtgacacc gcgcgtacct cgcgttcagt tggctcacac   1020
aacagcagct cgctcgcccc aagctcccgc gtcctgatcc gtaggtgagc catgcaaagg   1080
tcgccgcgcg ccctgatcca ttgcaccctt caaagctcga acctacaaat agcgtgcacc   1140
aggcatcctg gccacaccca cacagcaagc cagcagagca gaaagcagcc gcagccccag   1200
cccccacaag acgaggcaac a                                              1221

<210> SEQ ID NO 4
<211> LENGTH: 111
<212> TYPE: DNA
<213> ORGANISM: Zea mays

<400> SEQUENCE: 4
atggcgctag aagcagccac cgccccccgc gcactcctcg ccgcgtgcct cgtcctgctg     60
gtcctcggcg gcggcaccgg cccgtcgtcg gtgctgcgcg gcgccggggc g              111

<210> SEQ ID NO 5
<211> LENGTH: 37
<212> TYPE: PRT
<213> ORGANISM: Zea mays
```

<400> SEQUENCE: 5

Met Ala Leu Glu Ala Ala Thr Ala Pro Arg Ala Leu Ala Ala Cys
1               5                   10                  15

Leu Val Leu Leu Val Leu Gly Gly Ser Thr Gly Pro Ser Ser Val Leu
            20                  25                  30

Arg Gly Ala Gly Ala
        35

<210> SEQ ID NO 6
<211> LENGTH: 897
<212> TYPE: DNA
<213> ORGANISM: Zea mays

<400> SEQUENCE: 6
caggcgggcg gcggtggagc gggaggaggc agcggcagcg gcagcgtggc tgcgccggcg      60
gtgtgccgcc ccagcggctc gcggtggacg ccgacgccgg agcagatcag gatgctgaag     120
gagctctact acggctgcgg catccggtcg cccagctcgg agcagatcca gcgcatcacc     180
gccatgctgc ggcagcacgg caagatcgag ggcaagaacg tcttctactg gttccagaac     240
cacaaggccc gcgagcgcca gaagcgccgc ctcaccagcc tcgacgtcaa cgtgcccgcc     300
gccggcgcgg ccgacgccac caccagccaa ctcggcgtcc tctcgctgtc gtcgccgccg     360
ccttcaggcg cggcgcctcc ctcgcccacc ctcggcttct acgccgccgg caatggcggc     420
ggatcggctg tgctgctgga cacgagttcc gactggggca gcagcggcgc tgccatggcc     480
accgagacat gcttcctgca ggactacatg ggcgtgacgg acacgggcag ctcgtcgcag     540
tggccacgct tctcgtcgtc ggacacgata atggcggcgg ccgcggcgcg gcggcgacg     600
acgcgggcgc ccgagacgct ccctctcttc ccgacctgcg cgacgacgg cggcagcggt     660
agcagcagct acttgccgtt ctggggtgcc gcgtccacaa ctgccggcgc cacttcttcc     720
gttgcgatcc agcagcaaca ccagctgcag gagcagtaca gcttttacag caacagcaac     780
agcacccagc tggccggcac cggcaaccaa gacgtatcgg caacagcagc agcagccgcc     840
gccctggagc tgagcctcag ctcatggtgc tccccttacc ctgctgcagg gagtatg        897

<210> SEQ ID NO 7
<211> LENGTH: 299
<212> TYPE: PRT
<213> ORGANISM: Zea mays

<400> SEQUENCE: 7

Gln Ala Gly Gly Gly Ala Gly Gly Ser Gly Ser Gly Ser Val
1               5                   10                  15

Ala Ala Pro Ala Val Cys Arg Pro Ser Gly Ser Arg Trp Thr Pro Thr
            20                  25                  30

Pro Glu Gln Ile Arg Met Leu Lys Glu Leu Tyr Tyr Gly Cys Gly Ile
        35                  40                  45

Arg Ser Pro Ser Ser Glu Gln Ile Gln Arg Ile Thr Ala Met Leu Arg
    50                  55                  60

Gln His Gly Lys Ile Glu Gly Lys Asn Val Phe Tyr Trp Phe Gln Asn
65                  70                  75                  80

His Lys Ala Arg Glu Arg Gln Lys Arg Arg Leu Thr Ser Leu Asp Val
                85                  90                  95

Asn Val Pro Ala Ala Gly Ala Ala Asp Ala Thr Thr Ser Gln Leu Gly
            100                 105                 110

Val Leu Ser Leu Ser Ser Pro Pro Ser Gly Ala Ala Pro Pro Ser

```
                115                 120                 125
Pro Thr Leu Gly Phe Tyr Ala Ala Gly Asn Gly Gly Ser Ala Val
    130                 135                 140
Leu Leu Asp Thr Ser Ser Asp Trp Gly Ser Gly Ala Ala Met Ala
145                 150                 155                 160
Thr Glu Thr Cys Phe Leu Gln Asp Tyr Met Gly Val Thr Asp Thr Gly
                165                 170                 175
Ser Ser Ser Gln Trp Pro Arg Phe Ser Ser Ser Asp Thr Ile Met Ala
            180                 185                 190
Ala Ala Ala Arg Ala Ala Thr Thr Arg Ala Pro Glu Thr Leu Pro
        195                 200                 205
Leu Phe Pro Thr Cys Gly Asp Asp Gly Gly Ser Gly Ser Ser Ser Tyr
    210                 215                 220
Leu Pro Phe Trp Gly Ala Ala Ser Thr Thr Ala Gly Ala Thr Ser Ser
225                 230                 235                 240
Val Ala Ile Gln Gln Gln His Gln Leu Gln Glu Gln Tyr Ser Phe Tyr
                245                 250                 255
Ser Asn Ser Asn Ser Thr Gln Leu Ala Gly Thr Gly Asn Gln Asp Val
            260                 265                 270
Ser Ala Thr Ala Ala Ala Ala Ala Leu Glu Leu Ser Leu Ser Ser
        275                 280                 285
Trp Cys Ser Pro Tyr Pro Ala Ala Gly Ser Met
    290                 295

<210> SEQ ID NO 8
<211> LENGTH: 45
<212> TYPE: DNA
<213> ORGANISM: artificial sequence
<220> FEATURE:
<223> OTHER INFORMATION: synthetic

<400> SEQUENCE: 8
ggtggaggcg gctccggtgg cggaggctcc ggaggcggtg gctcc           45

<210> SEQ ID NO 9
<211> LENGTH: 15
<212> TYPE: PRT
<213> ORGANISM: artificial sequence
<220> FEATURE:
<223> OTHER INFORMATION: synthetic

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 720
<212> TYPE: DNA
<213> ORGANISM: Aequorea coerulescens

<400> SEQUENCE: 10
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
ctggtgacca ccctgagcta cggcgtgcag tgcttctcac gctaccccga tcacatgaag     240
cagcacgact tcttcaagag cgccatgcct gagggctaca tccaggagcg caccatcttc     300
ttcgaggatg acggcaacta caagtcgcgc gccgaggtga agttcgaggg cgataccctg     360
```

| | | | |
|---|---|---|---|
| gtgaatcgca tcgagctgac cggcaccgat ttcaaggagg atggcaacat cctgggcaat | 420 |
| aagatggagt acaactacaa cgcccacaat gtgtacatca tgaccgacaa ggccaagaat | 480 |
| ggcatcaagg tgaacttcaa gatccgccac aacatcgagg atggcagcgt gcagctggcc | 540 |
| gaccactacc agcagaatac ccccatcggc gatggccctg tgctgctgcc cgataaccac | 600 |
| tacctgtcca cccagagcgc cctgtccaag gaccccaacg agaagcgcga tcacatgatc | 660 |
| tacttcggct tcgtgaccgc cgccgccatc acccacggca tggatgagct gtacaagtga | 720 |

<210> SEQ ID NO 11
<211> LENGTH: 239
<212> TYPE: PRT
<213> ORGANISM: Aequorea coerulescens

<400> SEQUENCE: 11

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys
225                 230                 235

<210> SEQ ID NO 12
<211> LENGTH: 722
<212> TYPE: DNA
<213> ORGANISM: Zea mays

<400> SEQUENCE: 12

| | | |
|---|---|---|
| agcagggacc tggcacgcgt gctgcaatgg atggcaggag gggagaggaa taagaagtgt | 60 |
| ttccatttca cagtgagagc agtcgagctc caacgttgtc gtcgtcgtcg tcttcttctt | 120 |
| ttgatattca cactctgtct tgcggtctat atcatcagca taataataat aaaataagta | 180 |

```
aaaccaaacc atgcatgacc atgctataca tgttgcgagt tccagcgaga cggttaacta      240
taatgactgc aacaaggat tctgttcgtt ttgacacgtg atcacgtaag aataccgctc        300
aggagaccaa cacggatggt ctaaaccact atctccaaag taaaccatac tcaagtctta      360
aaaccgcaag agctacagtt gttctgaaat ctgaatgtag aactgcccat ctgcacagtc      420
agatcgaaac acctccgttt cagagcacag aagatggcga cgggatctct agagatcagt      480
aatcattcaa ccgctgcagt attttcatga acacacgcca ggcacgatct aaatgaccga     540
ttttataagt gcatatacta ctcgaccata actccagaac cttgtactct acgcagacgg      600
tttttctagg aacagagctt cctgcttgct agtgagaccg agatcgctca gtgacatctg     660
gctctccaat tcagtgaagg cacgcctggg ataagacctc gcctgtccaa agaaaaaggg     720
cg                                                                      722
```

<210> SEQ ID NO 13
<211> LENGTH: 1005
<212> TYPE: DNA
<213> ORGANISM: artificial sequence
<220> FEATURE:
<223> OTHER INFORMATION: synthetic

<400> SEQUENCE: 13

```
caggcgggcg gcggtggagc gggaggaggc agcggcagcg gcagcgtggc tgcgccggcg       60
gtgtgccgcc ccagcggctc gcggtggacg ccgacgccgg agcagatcag gatgctgaag      120
gagctctact acggctgcgg catccggtcg cccagctcgg agcagatcca gcgcatcacc      180
gccatgctgc ggcagcacgg caagatcgag ggcaagaacg tcttctactg gttccagaac      240
cacaaggccc gcgagcgcca gaagcgccgc tcaccagcc tcgacgtcaa cgtgcccgcc       300
gccggcgcgg ccgacgccac caccagccaa ctcggcgtcc tctcgctgtc gtcgccgccg     360
ccttcaggcg cggcgcctcc ctcgcccacc ctcggcttct acgccgcgg caatggcggc      420 ggatcggctg tgctgctgga cacgagttcc gactggggca gcagcggcgc tgccatggcc     480
accgagacat gcttcctgca ggactacatg ggcgtgacgg acacgggcag ctcgtcgcag     540
tggccacgct tctcgtcgtc ggacacgata atggcggcgg ccgcggcgcg ggcggcgacg     600
acgcgggcgc ccgagacgct ccctctcttc ccgacctgcg gcgacgacgg cggcagcggt     660
agcagcagct acttgccgtt ctggggtgcc gcgtccacaa ctgccggcgc cacttcttcc     720
gttgcgatcc agcagcaaca ccagctgcag gagcagtaca gcttttacag caacagcaac     780
agcacccagc tggccggcac cggcaaccaa gacgtatcgg caacagcagc agcagccgcc    840
gccctggagc tgagcctcag ctcatggtgc tccccttacc ctgctgcagg gagtatggaa     900 gttatggcg aggttcggcc aatagcccgg agcataaaga cggcccacga cgacgcaagg     960
gcagaactta tgtctgccga tagaccacgc tcaacacgcg gactg                    1005
```

<210> SEQ ID NO 14
<211> LENGTH: 335
<212> TYPE: PRT
<213> ORGANISM: artificial sequence
<220> FEATURE:
<223> OTHER INFORMATION: synthetic

<400> SEQUENCE: 14

Gln Ala Gly Gly Gly Gly Ala Gly Gly Gly Ser Gly Ser Gly Ser Val
1               5                   10                  15

Ala Ala Pro Ala Val Cys Arg Pro Ser Gly Ser Arg Trp Thr Pro Thr

```
            20                  25                  30
Pro Gln Ile Arg Met Leu Lys Glu Leu Tyr Tyr Gly Cys Gly Ile
        35                  40                  45
Arg Ser Pro Ser Ser Glu Gln Ile Gln Arg Ile Thr Ala Met Leu Arg
50                  55                  60
Gln His Gly Lys Ile Glu Gly Lys Asn Val Phe Tyr Trp Phe Gln Asn
65                  70                  75                  80
His Lys Ala Arg Glu Arg Gln Lys Arg Arg Leu Thr Ser Leu Asp Val
                85                  90                  95
Asn Val Pro Ala Ala Gly Ala Ala Asp Ala Thr Thr Ser Gln Leu Gly
            100                 105                 110
Val Leu Ser Leu Ser Ser Pro Pro Ser Gly Ala Ala Pro Pro Ser
        115                 120                 125
Pro Thr Leu Gly Phe Tyr Ala Ala Gly Asn Gly Gly Ser Ala Val
        130                 135                 140
Leu Leu Asp Thr Ser Ser Asp Trp Gly Ser Ser Gly Ala Ala Met Ala
145                 150                 155                 160
Thr Glu Thr Cys Phe Leu Gln Asp Tyr Met Gly Val Thr Asp Thr Gly
                165                 170                 175
Ser Ser Ser Gln Trp Pro Arg Phe Ser Ser Asp Thr Ile Met Ala
        180                 185                 190
Ala Ala Ala Arg Ala Ala Thr Thr Arg Ala Pro Glu Thr Leu Pro
        195                 200                 205
Leu Phe Pro Thr Cys Gly Asp Asp Gly Gly Ser Gly Ser Ser Ser Tyr
    210                 215                 220
Leu Pro Phe Trp Gly Ala Ala Ser Thr Thr Ala Gly Ala Thr Ser Ser
225                 230                 235                 240
Val Ala Ile Gln Gln Gln His Gln Leu Gln Glu Gln Tyr Ser Phe Tyr
                245                 250                 255
Ser Asn Ser Asn Ser Thr Gln Leu Ala Gly Thr Gly Asn Gln Asp Val
            260                 265                 270
Ser Ala Thr Ala Ala Ala Ala Ala Leu Glu Leu Ser Leu Ser Ser
        275                 280                 285
Trp Cys Ser Pro Tyr Pro Ala Ala Gly Ser Met Glu Val Met Ala Glu
    290                 295                 300
Val Arg Pro Ile Ala Arg Ser Ile Lys Thr Ala His Asp Asp Ala Arg
305                 310                 315                 320
Ala Glu Leu Met Ser Ala Asp Arg Pro Arg Ser Thr Arg Gly Leu
                325                 330                 335

<210> SEQ ID NO 15
<211> LENGTH: 1278
<212> TYPE: DNA
<213> ORGANISM: artificial sequence
<220> FEATURE:
<223> OTHER INFORMATION: synthetic

<400> SEQUENCE: 15
caggcgggcg gcggtggagc gggaggaggc agcggcagcg gcagcgtggc tgcgccggcg        60
gtgtgccgcc ccagcggctc gcggtggacg ccgacgccgg agcagatcag gatgctgaag       120
gagctctact acggctgcgg catccggtcg cccagctcgg agcagatcca gcgcatcacc       180
gccatgctgc ggcagcacgg caagatcgag ggcaagaacg tcttctactg gttccagaac       240
cacaaggccc gcgagcgcca gaagcgccgc ctcaccagcc tcgacgtcaa cgtgcccgcc       300
```

```
gccggcgcgg ccgacgccac caccagccaa ctcggcgtcc tctcgctgtc gtcgccgccg    360
ccttcaggcg cggcgcctcc ctcgcccacc ctcggcttct acgccgccgg caatggcggc    420
ggatcggctg tgctgctgga cacgagttcc gactggggca gcagcggcgc tgccatggcc    480
accgagacat gcttcctgca ggactacatg ggcgtgacgg acacgggcag ctcgtcgcag    540
tggccacgct tctcgtcgtc ggacacgata atggcggcgg ccgcggcgcg gcggcggacg    600
acgcgggcgc ccgagacgct ccctctcttc ccgacctgcg cgacgacgg cggcagcggt    660 agcagcagct acttgccgtt ctggggtgcc gcgtccacaa ctgccggcgc cacttcttcc    720
gttgcgatcc agcagcaaca ccagctgcag gagcagtaca gcttttacag caacagcaac    780
agcacccagc tggccggcac cggcaaccaa gacgtatcgg caacagcagc agcagccgcc    840
gccctggagc tgagcctcag ctcatggtgc tccccttacc ctgctgcagg gagtatgctg    900
aaaattctct cccggaatgc taaactcttg tcacacgcag ttcgccacgc agcaactctt    960
ccagatgggg agcagctgtc cgaggccag cttagccaga tgcgctccga ggtggcaaca   1020
aggcccgtgc tgggtgttgc gtacacacat caagatggtc agcctgagga cgccttca   1080 ggtaatcatc tggaccacaa aatcaacaac atccccaact tggtctttaa cgtggcggag   1140
cccattatgt tcaatgaaat ttccgctctg gaggttatgg ccgaggtcag accgatagcg   1200
agaagcatca aaactgcaca tgatgatgca agagccgaac tgatgtcggc ggaccgccca   1260
agatcgacga ggggcctg                                                 1278
```

<210> SEQ ID NO 16
<211> LENGTH: 426
<212> TYPE: PRT
<213> ORGANISM: artificial sequence
<220> FEATURE:
<223> OTHER INFORMATION: synthetic

<400> SEQUENCE: 16

```
Gln Ala Gly Gly Gly Ala Gly Gly Ser Gly Ser Gly Ser Val
1               5                   10                  15

Ala Ala Pro Ala Val Cys Arg Pro Ser Gly Ser Arg Trp Thr Pro Thr
            20                  25                  30

Pro Glu Gln Ile Arg Met Leu Lys Glu Leu Tyr Tyr Gly Cys Gly Ile
        35                  40                  45

Arg Ser Pro Ser Ser Glu Gln Ile Gln Arg Ile Thr Ala Met Leu Arg
    50                  55                  60

Gln His Gly Lys Ile Glu Gly Lys Asn Val Phe Tyr Trp Phe Gln Asn
65                  70                  75                  80

His Lys Ala Arg Glu Arg Gln Lys Arg Arg Leu Thr Ser Leu Asp Val
                85                  90                  95

Asn Val Pro Ala Ala Gly Ala Ala Asp Ala Thr Thr Ser Gln Leu Gly
            100                 105                 110

Val Leu Ser Leu Ser Ser Pro Pro Ser Gly Ala Ala Pro Pro Ser
        115                 120                 125

Pro Thr Leu Gly Phe Tyr Ala Ala Gly Asn Gly Gly Ser Ala Val
    130                 135                 140

Leu Leu Asp Thr Ser Ser Asp Trp Gly Ser Gly Ala Ala Met Ala
145                 150                 155                 160

Thr Glu Thr Cys Phe Leu Gln Asp Tyr Met Gly Val Thr Asp Thr Gly
                165                 170                 175

Ser Ser Ser Gln Trp Pro Arg Phe Ser Ser Ser Asp Thr Ile Met Ala
            180                 185                 190
```

Ala Ala Ala Ala Arg Ala Ala Thr Thr Arg Ala Pro Glu Thr Leu Pro
            195                 200                 205

Leu Phe Pro Thr Cys Gly Asp Asp Gly Gly Ser Gly Ser Ser Ser Tyr
    210                 215                 220

Leu Pro Phe Trp Gly Ala Ala Ser Thr Thr Ala Gly Ala Thr Ser Ser
225                 230                 235                 240

Val Ala Ile Gln Gln Gln His Gln Leu Gln Glu Gln Tyr Ser Phe Tyr
                245                 250                 255

Ser Asn Ser Asn Ser Thr Gln Leu Ala Gly Thr Gly Asn Gln Asp Val
            260                 265                 270

Ser Ala Thr Ala Ala Ala Ala Ala Leu Glu Leu Ser Leu Ser Ser
            275                 280                 285

Trp Cys Ser Pro Tyr Pro Ala Ala Gly Ser Met Leu Lys Ile Leu Ser
    290                 295                 300

Arg Asn Ala Lys Leu Leu Ser His Ala Val Arg His Ala Ala Thr Leu
305                 310                 315                 320

Pro Asp Gly Glu Gln Leu Ser Glu Ala Gln Leu Ser Gln Met Arg Ser
                325                 330                 335

Glu Val Ala Thr Arg Pro Val Leu Gly Val Ala Tyr Thr His Gln Asp
            340                 345                 350

Gly Gln Pro Glu Glu Arg Leu Ser Gly Asn His Leu Asp His Lys Ile
            355                 360                 365

Asn Asn Ile Pro Asn Leu Val Phe Asn Val Ala Glu Pro Ile Met Phe
370                 375                 380

Asn Glu Ile Ser Ala Leu Glu Val Met Ala Glu Val Arg Pro Ile Ala
385                 390                 395                 400

Arg Ser Ile Lys Thr Ala His Asp Asp Ala Arg Ala Glu Leu Met Ser
                405                 410                 415

Ala Asp Arg Pro Arg Ser Thr Arg Gly Leu
            420                 425

<210> SEQ ID NO 17
<211> LENGTH: 978
<212> TYPE: DNA
<213> ORGANISM: artificial sequence
<220> FEATURE:
<223> OTHER INFORMATION: synthetic

<400> SEQUENCE: 17
caggcgggcg gcggtggagc gggaggaggc agcggcagcg gcagcgtggc tgcgccggcg      60
gtgtgccgcc ccagcggctc gcggtggacg ccgacgccgg agcagatcag gatgctgaag     120
gagctctact acggctgcgg catccggtcg cccagctcgg agcagatcca gcgcatcacc     180
gccatgctgc ggcagcacgg caagatcgag ggcaagaacg tcttctactg gttccagaac     240
cacaaggccc gcgagcgcca gaagcgccgc ctcaccagcc tcgacgtcaa cgtgcccgcc     300
gccggcgcgg ccgacgccac caccagccaa ctcggcgtcc tctcgctgtc gtcgccgccg     360
ccttcaggcg cggcgcctcc ctcgcccacc ctcggcttct acgccgccgg caatggcggc     420
ggatcggctg tgctgctgga cacgagttcc gactggggca gcagcggcgc tgccatggcc     480
accgagacat gcttcctgca ggactacatg ggcgtgacgg acacgggcag ctcgtcgcag     540
tggccacgct ctcgtcgtc ggacacgata atggcggcgg ccgcggcgcg ggcggcgacg     600
acgcgggcgc ccgagacgct ccctctcttc ccgacctgcg cgacgacgg cggcagcggt     660 agcagcagct acttgccgtt ctggggtgcc gcgtccacaa ctgccggcgc cacttcttcc     720

```
gttgcgatcc agcagcaaca ccagctgcag gagcagtaca gcttttacag caacagcaac    780
agcacccagc tggccggcac cggcaaccaa gacgtatcgg caacagcagc agcagccgcc    840
gccctggagc tgagcctcag ctcatggtgc tccccttacc ctgctgcagg gagtatgccg    900
aaagcggcca atgatgtgga tcggttgaca cgggacttcg atgagcggat acgggttaga    960
ggcgacggca gggggctg                                                  978
```

```
<210> SEQ ID NO 18
<211> LENGTH: 326
<212> TYPE: PRT
<213> ORGANISM: artificial sequence
<220> FEATURE:
<223> OTHER INFORMATION: synthetic

<400> SEQUENCE: 18
```

```
Gln Ala Gly Gly Gly Ala Gly Gly Ser Gly Ser Gly Ser Val
1               5                   10                  15

Ala Ala Pro Ala Val Cys Arg Pro Ser Gly Ser Arg Trp Thr Pro Thr
            20                  25                  30

Pro Glu Gln Ile Arg Met Leu Lys Glu Leu Tyr Tyr Gly Cys Gly Ile
        35                  40                  45

Arg Ser Pro Ser Ser Glu Gln Ile Gln Arg Ile Thr Ala Met Leu Arg
    50                  55                  60

Gln His Gly Lys Ile Glu Gly Lys Asn Val Phe Tyr Trp Phe Gln Asn
65                  70                  75                  80

His Lys Ala Arg Glu Arg Gln Lys Arg Arg Leu Thr Ser Leu Asp Val
                85                  90                  95

Asn Val Pro Ala Ala Gly Ala Ala Asp Ala Thr Thr Ser Gln Leu Gly
            100                 105                 110

Val Leu Ser Leu Ser Ser Pro Pro Ser Gly Ala Ala Pro Pro Ser
            115                 120                 125

Pro Thr Leu Gly Phe Tyr Ala Ala Gly Asn Gly Gly Ser Ala Val
            130                 135                 140

Leu Leu Asp Thr Ser Ser Asp Trp Gly Ser Ser Gly Ala Ala Met Ala
145                 150                 155                 160

Thr Glu Thr Cys Phe Leu Gln Asp Tyr Met Gly Val Thr Asp Thr Gly
                165                 170                 175

Ser Ser Ser Gln Trp Pro Arg Phe Ser Ser Asp Thr Ile Met Ala
            180                 185                 190

Ala Ala Ala Arg Ala Ala Thr Thr Arg Ala Pro Glu Thr Leu Pro
            195                 200                 205

Leu Phe Pro Thr Cys Gly Asp Asp Gly Gly Ser Gly Ser Ser Ser Tyr
    210                 215                 220

Leu Pro Phe Trp Gly Ala Ala Ser Thr Thr Ala Gly Ala Thr Ser Ser
225                 230                 235                 240

Val Ala Ile Gln Gln Gln His Gln Leu Gln Glu Gln Tyr Ser Phe Tyr
                245                 250                 255

Ser Asn Ser Asn Ser Thr Gln Leu Ala Gly Thr Gly Asn Gln Asp Val
            260                 265                 270

Ser Ala Thr Ala Ala Ala Ala Leu Glu Leu Ser Leu Ser Ser
            275                 280                 285

Trp Cys Ser Pro Tyr Pro Ala Ala Gly Ser Met Pro Lys Ala Ala Asn
            290                 295                 300

Asp Val Asp Arg Leu Thr Arg Asp Phe Asp Glu Arg Ile Arg Val Arg
```

| 305 | 310 | 315 | 320 |

Gly Asp Gly Arg Gly Leu
             325

<210> SEQ ID NO 19
<211> LENGTH: 2133
<212> TYPE: DNA
<213> ORGANISM: Zea mays

<400> SEQUENCE: 19

| | | | | | |
|---|---|---|---|---|---|
| atggccactg | tgaacaactg | gctcgctttc | tccctctccc | cgcaggagct | gccgccctcc | 60 |
| cagacgacgg | actccacact | catctcggcc | gccaccgccg | accatgtctc | cggcgatgtc | 120 |
| tgcttcaaca | tcccccaaga | ttggagcatg | aggggatcag | agctttcggc | gctcgtcgcg | 180 |
| gagccgaagc | tggaggactt | cctcggcggc | atctccttct | ccgagcagca | tcacaaggcc | 240 |
| aactgcaaca | tgatacccag | cactagcagc | acagtttgct | acgcgagctc | aggtgctagc | 300 |
| accggctacc | atcaccagct | gtaccaccag | cccaccagct | cagcgctcca | cttcgcggac | 360 |
| tccgtaatgg | tggcttcctc | ggccggtgtc | cacgacggcg | gtgccatgct | cagcgcggcc | 420 |
| gccgctaacg | tgtcgctgg | cgctgccagt | gccaacggcg | gcggcatcgg | gctgtccatg | 480 |
| attaagaact | ggctgcggag | ccaaccggcg | cccatgcagc | cgagggtggc | ggcggctgag | 540 |
| ggcgcgcagg | ggctctcttt | gtccatgaac | atggcgggga | cgacccaagg | cgctgctggc | 600 |
| atgccacttc | tcgctggaga | gcgcgcacgg | gcgcccgaga | gtgtatcgac | gtcagcacag | 660 |
| ggtggagccg | tcgtcgtcac | ggcgccgaag | gaggatagcg | gtggcagcgg | tgttgccggc | 720 |
| gctctagtag | ccgtgagcac | ggacacgggt | ggcagcggcg | gcgcgtcggc | tgacaacacg | 780 |
| gcaaggaaga | cggtggacac | gttcgggcag | cgcacgtcga | tttaccgtgg | cgtgacaagg | 840 |
| catagatgga | ctgggagata | tgaggcacat | cttgggata | acagttgcag | aagggaaggg | 900 |
| caaactcgta | aggtcgtca | agtctattta | ggtggctatg | ataaagagga | gaaagctgct | 960 |
| agggcttatg | atcttgctgc | tctgaagtac | tggggtgcca | caacaacaac | aaatttttcca | 1020 |
| gtgagtaact | acgaaaagga | gctcgaggac | atgaagcaca | tgacaaggca | ggagtttgta | 1080 |
| gcgtctctga | aaggaagag | cagtggtttc | tccagaggtg | catccattta | caggggagtg | 1140 |
| actaggcatc | accaacatgg | aagatggcaa | gcacggattg | gacgagttgc | agggaacaag | 1200 |
| gatctttact | tgggcacctt | cagcacccag | gaggaggcag | cggaggcgta | cgacatcgcg | 1260 |
| gcgatcaagt | tccgcggcct | caacgccgtc | accaacttcg | acatgagccg | ctacgacgtg | 1320 |
| aagagcatcc | tggacagcag | cgccctcccc | atcggcagcg | ccgccaagcg | cctcaaggag | 1380 |
| gccgaggccg | cagcgtccgc | gcagcaccac | cacgccggcg | tggtgagcta | cgacgtcggc | 1440 |
| cgcatcgcct | cgcagctcgg | cgacggcgga | gccctggcgg | cggcgtacgg | cgcgcactac | 1500 |
| cacggcgccg | cctggccgac | catcgcgttc | cagccgggcg | ccgccagcac | aggcctgtac | 1560 |
| cacccgtacg | cgcagcagcc | aatgcgcggc | ggcgggtggt | gcaagcagga | gcaggaccac | 1620 |
| gcggtgatcg | cggccgcgca | cagcctgcag | gacctccacc | acctgaacct | gggcgcggcc | 1680 |
| ggcgcgcacg | acttttttctc | ggcagggcag | caggccgccg | ccgctgcgat | gcacggcctg | 1740 |
| ggtagcatcg | acagtgcgtc | gctcgagcac | agcaccggct | ccaactccgt | cgtctacaac | 1800 |
| ggcggggtcg | cgacagcaa | cggcgccagc | gccgtcggcg | gcagtggcgg | tggctacatg | 1860 |
| atgccgatga | cgctgccgg | agcaaccact | acatcggcaa | tggtgagcca | cgagcaggtg | 1920 |
| catgcacggg | cctacgacga | agccaagcag | gctgctcaga | tggggtacga | gagctacctg | 1980 |

-continued

```
gtgaacgcgg agaacaatgg tggcggaagg atgtctgcat gggggactgt cgtgtctgca    2040
gccgcggcgg cagcagcaag cagcaacgac aacatggccg ccgacgtcgg gcatggcggc    2100
gcgcagctct tcagtgtctg gaacgacact taa                                 2133
```

<210> SEQ ID NO 20
<211> LENGTH: 710
<212> TYPE: PRT
<213> ORGANISM: Zea mays

<400> SEQUENCE: 20

```
Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110

Ser Ser Ala Leu His Phe Ala Asp Ser Val Met Val Ala Ser Ser Ala
        115                 120                 125

Gly Val His Asp Gly Gly Ala Met Leu Ser Ala Ala Ala Ala Asn Gly
    130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
    210                 215                 220

Val Val Thr Ala Pro Lys Glu Asp Ser Gly Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350
```

```
His Met Thr Arg Gln Glu Phe Val Ala Ser Leu Arg Arg Lys Ser Ser
            355                 360                 365
Gly Phe Ser Arg Gly Ala Ser Ile Tyr Arg Gly Val Thr Arg His His
    370                 375                 380
Gln His Gly Arg Trp Gln Ala Arg Ile Gly Arg Val Ala Gly Asn Lys
385                 390                 395                 400
Asp Leu Tyr Leu Gly Thr Phe Ser Thr Gln Glu Glu Ala Ala Glu Ala
                405                 410                 415
Tyr Asp Ile Ala Ala Ile Lys Phe Arg Gly Leu Asn Ala Val Thr Asn
            420                 425                 430
Phe Asp Met Ser Arg Tyr Asp Val Lys Ser Ile Leu Asp Ser Ser Ala
            435                 440                 445
Leu Pro Ile Gly Ser Ala Ala Lys Arg Leu Lys Glu Ala Glu Ala Ala
    450                 455                 460
Ala Ser Ala Gln His His His Ala Gly Val Val Ser Tyr Asp Val Gly
465                 470                 475                 480
Arg Ile Ala Ser Gln Leu Gly Asp Gly Gly Ala Leu Ala Ala Ala Tyr
                485                 490                 495
Gly Ala His Tyr His Gly Ala Ala Trp Pro Thr Ile Ala Phe Gln Pro
            500                 505                 510
Gly Ala Ala Ser Thr Gly Leu Tyr His Pro Tyr Ala Gln Gln Pro Met
            515                 520                 525
Arg Gly Gly Gly Trp Cys Lys Gln Glu Gln Asp His Ala Val Ile Ala
    530                 535                 540
Ala Ala His Ser Leu Gln Asp Leu His His Leu Asn Leu Gly Ala Ala
545                 550                 555                 560
Gly Ala His Asp Phe Phe Ser Ala Gly Gln Gln Ala Ala Ala Ala Ala
                565                 570                 575
Met His Gly Leu Gly Ser Ile Asp Ser Ala Ser Leu Glu His Ser Thr
            580                 585                 590
Gly Ser Asn Ser Val Val Tyr Asn Gly Gly Val Gly Asp Ser Asn Gly
    595                 600                 605
Ala Ser Ala Val Gly Gly Ser Gly Gly Gly Tyr Met Met Pro Met Ser
    610                 615                 620
Ala Ala Gly Ala Thr Thr Thr Ser Ala Met Val Ser His Glu Gln Val
625                 630                 635                 640
His Ala Arg Ala Tyr Asp Glu Ala Lys Gln Ala Ala Gln Met Gly Tyr
                645                 650                 655
Glu Ser Tyr Leu Val Asn Ala Glu Asn Asn Gly Gly Arg Met Ser
            660                 665                 670
Ala Trp Gly Thr Val Val Ser Ala Ala Ala Ala Ala Ala Ser Ser
            675                 680                 685
Asn Asp Asn Met Ala Ala Asp Val Gly His Gly Gly Ala Gln Leu Phe
    690                 695                 700
Ser Val Trp Asn Asp Thr
705                 710

<210> SEQ ID NO 21
<211> LENGTH: 48
<212> TYPE: DNA
<213> ORGANISM: Zea mays

<400> SEQUENCE: 21
aaacagatca acaactggtt tatcaatcaa aggaagcggc actggaaa                48
```

<210> SEQ ID NO 22
<211> LENGTH: 16
<212> TYPE: PRT
<213> ORGANISM: Zea mays

<400> SEQUENCE: 22

```
Lys Gln Ile Asn Asn Trp Phe Ile Asn Gln Arg Lys Arg His Trp Lys
1               5                   10                  15
```

<210> SEQ ID NO 23
<211> LENGTH: 63
<212> TYPE: DNA
<213> ORGANISM: Schizosaccharomyces pombe

<400> SEQUENCE: 23

```
gcgggctacc ttctcggtaa aataaacctc aaagcatgcg ctgcttgcgc gaaaaaata    60 ctg                                                                 63
```

<210> SEQ ID NO 24
<211> LENGTH: 21
<212> TYPE: PRT
<213> ORGANISM: Schizosaccharomyces pombe

<400> SEQUENCE: 24

```
Ala Gly Tyr Leu Leu Gly Lys Ile Asn Leu Lys Ala Cys Ala Ala Cys
1               5                   10                  15

Ala Lys Lys Ile Leu
            20
```

<210> SEQ ID NO 25
<211> LENGTH: 162
<212> TYPE: DNA
<213> ORGANISM: Candida albicans

<400> SEQUENCE: 25

```
gaatgtgact cggaactgga gattaaacgg tataagcggg tcagagtcgc atccagaaag   60
tgtcgggcca aatttaagca acttttgcaa cattataggg aggttgcagc agcaaaatct  120
tcagaaaatg atcgcttgag gctcctcctc aagcagatgt gc                     162
```

<210> SEQ ID NO 26
<211> LENGTH: 54
<212> TYPE: PRT
<213> ORGANISM: Candida albicans

<400> SEQUENCE: 26

```
Glu Cys Asp Ser Glu Leu Glu Ile Lys Arg Tyr Lys Arg Val Arg Val
1               5                   10                  15

Ala Ser Arg Lys Cys Arg Ala Lys Phe Lys Gln Leu Leu Gln His Tyr
            20                  25                  30

Arg Glu Val Ala Ala Ala Lys Ser Ser Glu Asn Asp Arg Leu Arg Leu
        35                  40                  45

Leu Leu Lys Gln Met Cys
    50
```

<210> SEQ ID NO 27
<211> LENGTH: 63
<212> TYPE: DNA
<213> ORGANISM: artificial sequence
<220> FEATURE:
<223> OTHER INFORMATION: synthetic

<400> SEQUENCE: 27
aaagagacat ggtgggaaac atggtggacc gagtggagcc agccaaagaa aaaaagaaaa    60
gtg    63

<210> SEQ ID NO 28
<211> LENGTH: 21
<212> TYPE: PRT
<213> ORGANISM: artificial sequence
<220> FEATURE:
<223> OTHER INFORMATION: synthetic

<400> SEQUENCE: 28

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 29
<211> LENGTH: 33
<212> TYPE: DNA
<213> ORGANISM: human immunodeficiency virus

<400> SEQUENCE: 29
tatgggagga aaaacgcag gcaaaggaga cgc    33

<210> SEQ ID NO 30
<211> LENGTH: 11
<212> TYPE: PRT
<213> ORGANISM: human immunodeficiency virus

<400> SEQUENCE: 30

Tyr Gly Arg Lys Lys Arg Arg Gln Arg Arg Arg
1               5                   10

<210> SEQ ID NO 31
<211> LENGTH: 63
<212> TYPE: DNA
<213> ORGANISM: Zea mays

<400> SEQUENCE: 31
atggcaaaac tactcttggg tttgctcctt gcccttgcta ttctagggac aacatcggct    60
gct    63

<210> SEQ ID NO 32
<211> LENGTH: 21
<212> TYPE: PRT
<213> ORGANISM: Zea mays

<400> SEQUENCE: 32

Met Ala Lys Leu Leu Leu Gly Leu Leu Leu Ala Leu Ala Ile Leu Gly
1               5                   10                  15

Thr Thr Ser Ala Ala
            20

<210> SEQ ID NO 33
<211> LENGTH: 1621
<212> TYPE: DNA
<213> ORGANISM: Zea mays

<400> SEQUENCE: 33
ctacatctaa tgcatagaaa caccaagatc acattgtact agcaaaatgt catagaagac    60

```
tagttaaaac cttgtttggt ccgctcaacc ttaaaaatca cctaggagac atgctagaag     120
tatctcaaca gagaatgaca ccatatagta gtggcaccaa gtgcctaatc tgcacacaaa     180
aaatcgtaca atacatgaca tcaaggctta ataatagagt gtatgttaaa gcgagcatgc     240
aacctatgag tggtatgtag gagttaggtt taaacaaggt aatggctcaa gcaccacaca     300
tcctaccaca atgtcgtaat aaatataaaa gcactagcaa tctatttagc atgcctaaat     360
gggatactat gaggttgggt gggatgtggc acctttgtat aatggcccag ttccttagtg     420
tagtcttgat cctccccgtt aggttcagac tcctctaggg attttgtagg aatcatcaaa     480
ttttcataag caatttcttg tgcacaaaga accaaataga ttgaaaaagt tccaaattca     540
ctcaaacaca aaaccatggc acatagctta tgtgacaaaa tatttggaca ctagtttcat     600
attttttgag atcatataag tttattatca aactccaagg attaaattat tttttgaaaa     660
aaaaagaaaa agggaaaaca tcataaggtg acacatggca acctctgaat gactagactt     720
ttaccatctc tcaggtgggt ctggtcaaca atcactgttg gtcggtcctt accttgccta     780
gacgggtcct tagtaggcct actgggttga gttatgggat aaattgtggc ctagaaacat     840
accagtccac caaccttggg accacttaaa aaattgcatc ttgcaccatt atactattta     900
gatgttttta aaaacaata ataacttta catcgaaatc aaaactagac aaatttata      960 ctttcacaga gcagcagaaa tttatacaat atgattgaat acaagatgta ggacccaatg    1020
gagagaattt ttttgtctcc tatatgcttg aatacccaac ataatatctt cgcagcatac    1080
tatctatcta atagaaaaat tataatatag ttaaatactt aagtagtatc tagtggatag    1140
aattcaatat ctcatacatg catgaggagt aatatctact agacatgcaa catatttta    1200 tctatctaat agaatatata taataaagtt aaatattata tgcatcacct actatatata    1260
atttgatatc ttttagatgt ataagggact aagaataata tctctagcac acatgcaatg    1320
cattatctat ctaaatatat tatataatag ttaaatatta attatacgta gtctaaacct    1380
acatataagc ctacccatcc ccacttaaag atctcagtgt cacacataga ccatacatct    1440
cacttcgcca aaaaatttc gtcaacagtt gaagttatac ccataatagt taaatattaa    1500
ttatacgtag tctaaaccta catataagcc tacccatccc cacttaaaga tctcagtgtc    1560
acacatagac catacatctc acttcgccaa aaaatttcg tcaacagttg aagttatacc    1620
c                                                                    1621

<210> SEQ ID NO 34
<211> LENGTH: 72
<212> TYPE: DNA
<213> ORGANISM: Zea mays

<400> SEQUENCE: 34
atggcaaaac tgttgagcct gttcttagcc ctctcctttg tagcagctat gtttgccata      60
ggctctcatg ct                                                          72

<210> SEQ ID NO 35
<211> LENGTH: 24
<212> TYPE: PRT
<213> ORGANISM: Zea mays

<400> SEQUENCE: 35

Met Ala Lys Leu Leu Ser Leu Phe Leu Ala Leu Ser Phe Val Ala Ala
1               5                   10                  15

Met Phe Ala Ile Gly Ser His Ala
```

<210> SEQ ID NO 36
<211> LENGTH: 1454
<212> TYPE: DNA
<213> ORGANISM: Zea mays

<400> SEQUENCE: 36

```
tcaaattcaa atataattct tcaaatgtta tatatggtcc actcaaaagt ttgccacgtt      60
attttagatt aaaaaaagtt gttagatatg tatgtctgtc cattcgatta ggggtgctaa     120
aaatattatc aaaactaatt aactaaaaaa atttcattta aaaagtaatt gaacccaaaa     180
tatcatggta tgtttggtga agacagtgat cagtgatttt tttatatcta tatatatatc     240
aaagatactt gattttctag aaggttcttt ttgttgtttt cccttatgtt tttacgcatg     300
atgcaattct ttttgagagg tttccgatgc attgatgtta ttgtattatc tcctatatat     360
aggtcgacgt acattatgta ttgcaataac cagttaactg gatccagctt cgcttagttt     420
ttagttttg gcagaaaaaa tgatcaatgt ttcacaaacc aaatattttt ataacttttg      480
atgaaagaag atcaccacgg tcatatctag gggtggtaac aaattgcgat ctaaatgttt     540
cttcataaaa aataaggctt cttaataaat tttagttcaa aataaatacg aataaagtct     600
gattctaatc tgattcgatc cttaaatttt ataatgcaaa atttagagct cattaccacc     660
tctagtcata tgtctagtct gaggtatatc caaaaagccc tttctctaaa ttccacaccc     720
aactcagatg tttgcaaata aatactccga ctccaaaatg taggtgaagt gcaactttct     780
ccattttata tcaacatttg ttattttttg tttaacattt cacactcaaa actaattaat     840
aaaatacgtg gttgttgaac gtgcgcacat gtctccctta cattatgttt ttttattat     900
gtattattgt tgttttcctc cgaacaactt gtcaacatat catcattggt ctttaatatt     960
tatgaatatg gaagcctagt tatttacact tggctacaca ctagttgtag ttttgccact    1020
tgtctaacat gcaactctag tagttttgcc acttgcctgg catgcaactc tagtattgac    1080
acttgtatag catataatgc caatacgaca cctgccttac atgaaacatt attttgaca     1140
cttgtatacc atgcaacatt accattgaca tttgtccata cacattatat caaatatatt    1200
gagcgcatgt cacaaactcg atacaaagct ggatgaccct ccctcaccac atctataaaa    1260
acccgagcgc tactctaaat cactcacaac acaacacata tcttttagta acctttcaat    1320
aggcgtcccc caagaactag taaaccctc cctcaccaca tctataaaaa cccgagcgct    1380
actctaaatc actcacaaca caacacatat cttttagtaa cctttcaata ggcgtccccc    1440
aagaactagt aaac                                                      1454
```

<210> SEQ ID NO 37
<211> LENGTH: 1560
<212> TYPE: DNA
<213> ORGANISM: Zea mays

<400> SEQUENCE: 37

```
atggcaaaac tgttgagcct gttcttagcc ctctcctttg tagcagctat gtttgccata     60
ggctctcatg ctgacacgtt cgggcagcgc acgtcgattt accgtggcgt gacaaggcat    120
agatggactg ggagatatga ggcacatctt tgggataaca gttgcagaag ggaagggcaa    180
actcgtaagg gtcgtcaagt ctatttaggt ggctatgata agaggagaa agctgctagg     240
gcttatgatc ttgctgctct gaagtactgg ggtgccacaa caacaacaaa ttttccagtg    300
agtaactacg aaaaggagct cgaggacatg aagcacatga caaggcagga gtttgtagcg    360
```

```
tctctgagaa ggaagagcag tggtttctcc agaggtgcat ccatttacag gggagtgact    420
aggcatcacc aacatggaag atggcaagca cggattggac gagttgcagg gaacaaggat    480
ctttacttgg gcaccttcag cacccaggag gaggcagcgg aggcgtacga catcgcggcg    540
atcaagttcc gcggcctcaa cgccgtcacc aacttcgaca tgagccgcta cgacgtgaag    600
agcatcctgg acagcagcgc cctccccatc ggcagcgccg ccaagcgcct caaggaggcc    660
gaggccgcag cgtccgcgca gcaccaccac gccggcgtgg tgagctacga cgtcggccgc    720
atcgcctcgc agctcggcga cggcggagcc ctggcggcgg cgtacggcgc gcactaccac    780
ggcgccgcct ggccgaccat cgcgttccag ccgggcgccg ccagcacagg cctgtaccac    840
ccgtacgcgc agcagccaat gcgcggcggc gggtggtgca agcaggagca ggaccacgcg    900
gtgatcgcgg ccgcgcacag cctgcaggac ctccaccacc tgaacctggg cgcggccggc    960
gcgcacgact ttttctcggc agggcagcag gccgccgccg ctgcgatgca cggcctgggt    1020
agcatcgaca gtgcgtcgct cgagcacagc accggctcca actccgtcgt ctacaacggc    1080
ggggtcggcg acagcaacgg cgccagcgcc gtcggcggca gtggcggtgg ctacatgatg    1140
ccgatgagcg ctgccggagc aaccactaca tcggcaatgg tgagccacga gcaggtgcat    1200
gcacgggcct acgacgaagc caagcaggct gctcagatgg ggtacgagag ctacctggtg    1260
aacgcggaga caatggtgg cggaaggatg tctgcatggg ggactgtcgt gtctgcagcc    1320
gcggcggcag cagcaagcag caacgacaac atggccgccg acgtcggcca tggcggcgcg    1380
cagctcttca gtgtctggaa cgacactccg aaagcggcca atgatgtgga tcggttgaca    1440
cgggacttcg atgagcggat acgggttaga ggcgacggca ggggctgga ctataaggat     1500
gacgacgata agaaacagat caacaactgg tttatcaatc aaaggaagcg gcactggaaa    1560
```

<210> SEQ ID NO 38
<211> LENGTH: 520
<212> TYPE: PRT
<213> ORGANISM: Zea mays

<400> SEQUENCE: 38

```
Met Ala Lys Leu Leu Ser Leu Phe Leu Ala Leu Ser Phe Val Ala Ala
1               5                   10                  15

Met Phe Ala Ile Gly Ser His Ala Asp Thr Phe Gly Gln Arg Thr Ser
                20                  25                  30

Ile Tyr Arg Gly Val Thr Arg His Arg Trp Thr Gly Arg Tyr Glu Ala
            35                  40                  45

His Leu Trp Asp Asn Ser Cys Arg Arg Glu Gly Gln Thr Arg Lys Gly
        50                  55                  60

Arg Gln Val Tyr Leu Gly Gly Tyr Asp Lys Glu Glu Lys Ala Ala Arg
65                  70                  75                  80

Ala Tyr Asp Leu Ala Ala Leu Lys Tyr Trp Gly Ala Thr Thr Thr Thr
                85                  90                  95

Asn Phe Pro Val Ser Asn Tyr Glu Lys Glu Leu Glu Asp Met Lys His
                100                 105                 110

Met Thr Arg Gln Glu Phe Val Ala Ser Leu Arg Arg Lys Ser Ser Gly
            115                 120                 125

Phe Ser Arg Gly Ala Ser Ile Tyr Arg Gly Val Thr Arg His His Gln
        130                 135                 140

His Gly Arg Trp Gln Ala Arg Ile Gly Arg Val Ala Gly Asn Lys Asp
145                 150                 155                 160
```

Leu Tyr Leu Gly Thr Phe Ser Thr Gln Glu Ala Ala Glu Ala Tyr
                     165                 170                 175

Asp Ile Ala Ala Ile Lys Phe Arg Gly Leu Asn Ala Val Thr Asn Phe
            180                 185                 190

Asp Met Ser Arg Tyr Asp Val Lys Ser Ile Leu Asp Ser Ser Ala Leu
        195                 200                 205

Pro Ile Gly Ser Ala Ala Lys Arg Leu Lys Glu Ala Glu Ala Ala
    210                 215                 220

Ser Ala Gln His His His Ala Gly Val Val Ser Tyr Asp Val Gly Arg
225                 230                 235                 240

Ile Ala Ser Gln Leu Gly Asp Gly Gly Ala Leu Ala Ala Tyr Gly
                245                 250                 255

Ala His Tyr His Gly Ala Ala Trp Pro Thr Ile Ala Phe Gln Pro Gly
            260                 265                 270

Ala Ala Ser Thr Gly Leu Tyr His Pro Tyr Ala Gln Gln Pro Met Arg
        275                 280                 285

Gly Gly Gly Trp Cys Lys Gln Glu Gln Asp His Ala Val Ile Ala Ala
    290                 295                 300

Ala His Ser Leu Gln Asp Leu His His Leu Asn Leu Gly Ala Ala Gly
305                 310                 315                 320

Ala His Asp Phe Phe Ser Ala Gly Gln Gln Ala Ala Ala Ala Met
                325                 330                 335

His Gly Leu Gly Ser Ile Asp Ser Ala Ser Leu Glu His Ser Thr Gly
            340                 345                 350

Ser Asn Ser Val Val Tyr Asn Gly Gly Val Gly Asp Ser Asn Gly Ala
        355                 360                 365

Ser Ala Val Gly Gly Ser Gly Gly Tyr Met Met Pro Met Ser Ala
    370                 375                 380

Ala Gly Ala Thr Thr Thr Ser Ala Met Val Ser His Glu Gln Val His
385                 390                 395                 400

Ala Arg Ala Tyr Asp Glu Ala Lys Gln Ala Ala Gln Met Gly Tyr Glu
                405                 410                 415

Ser Tyr Leu Val Asn Ala Glu Asn Asn Gly Gly Gly Arg Met Ser Ala
            420                 425                 430

Trp Gly Thr Val Val Ser Ala Ala Ala Ala Ala Ser Ser Asn
        435                 440                 445

Asp Asn Met Ala Ala Asp Val Gly His Gly Gly Ala Gln Leu Phe Ser
    450                 455                 460

Val Trp Asn Asp Thr Pro Lys Ala Ala Asn Asp Val Asp Arg Leu Thr
465                 470                 475                 480

Arg Asp Phe Asp Glu Arg Ile Arg Val Arg Gly Asp Gly Arg Gly Leu
                485                 490                 495

Asp Tyr Lys Asp Asp Asp Asp Lys Lys Gln Ile Asn Asn Trp Phe Ile
            500                 505                 510

Asn Gln Arg Lys Arg His Trp Lys
        515                 520

<210> SEQ ID NO 39
<211> LENGTH: 1536
<212> TYPE: DNA
<213> ORGANISM: artificial sequence
<220> FEATURE:
<223> OTHER INFORMATION: synthetic

<400> SEQUENCE: 39

```
tgctagtgaa cctcaaggat tgggggtgat aaatgcgtgc ttaattttg aggatctagt      60 aatcaagagt gagaggaggc aaaacatcga ttcttcatag tgcttaaata gaaaagagtg    120
ataatactac tcctttgttc gtcgagtact aaaagactac tacatccatt ttacaattat    180
tttttagata cataaacttt attattataa atctagacgt agttaagtgc aatgcaaaca    240
acttatattt tagtaataca taccattaat aaataatcct agtagatagt atatatatct    300
aataagatga tattaaagga tgataataat aacaattaat aaatactact agtcacaaaa    360
agataagttt agcaacaatt aagtttagta gtgcatgaag ttgttttacg atattgataa    420
tatttatcac gcaaattttg tatattatag tgatgttttt tgttccatat ctatgtttta    480
tacaaatttt ttactgccgc aatgcactgc acatatctag ttttagtact atatacaatt    540
aataaataat agataaatact agcacatagt atatatctaa tgaaacgata ttaaaaggat    600
ggtaataata gcaattaata aatactagta gtatacaaaa gataagttta gcaacaatca    660
aactaaaaga tagccagtag aattttattt attttatatt actgaaaaca tcctcaagtg    720
ttcaccctgc agcccatcgc ctattctatt taagaaatgc ccgccctccc atactgctat    780
cactcaagcc tattctccat tgtggaacca acaaatctcc aagctctccc aatttagaaa    840
cgagccatgg ccctgtccaa caagttcatc ggcgacgaca tgaagatgac gtaccacatg    900
gacgggtgcg tcaacggcca ctacttcacc gtcaagggcg aagggtccgg taagccatac    960
gagggcacga gacctccac attcaaggtc acgatggcta acggtggtcc gctggccttc   1020
tcattcgata tcctgagcac cgtcttcatg tacgggaaca ggtgcttcac ggcgtacccg   1080
acctcaatgc cagactactt caagcaggcc ttcccggacg gcatgtcgta cgagaggacc   1140
ttcacctacg aggacggtgg cgtggcgact gcttcgtggg agatctccct caagggcaac   1200
tgcttcgaac acaagtcgac gttccacggc gtgaatttcc cagcggacgg gccagtcatg   1260
gcaaagaaga cgactggctg ggacccgagc ttcgagaaga tgacggtctg cgacggcatc   1320
ctcaagggcg acgttacggc ttttctcatg ctgcagggcg agggaatta taggtgccag   1380 ttccacacca gctacaagac gaagaagccg gtcacgatgc cgccgaacca cgtcgtcgag   1440
cacaggatag cgaggaccga ccttgacaag ggcggcaact cggtgcagct cactgagcac   1500
gccgtcgcac acatcacgtc agtcgtgccg ttctag                             1536

<210> SEQ ID NO 40
<211> LENGTH: 63
<212> TYPE: DNA
<213> ORGANISM: Thosea asigna virus

<400> SEQUENCE: 40
ggctccggcg agggtcgcgg ttccctcctg acctgcggcg acgtggagga aaaccccggt     60
ccc                                                                  63

<210> SEQ ID NO 41
<211> LENGTH: 21
<212> TYPE: PRT
<213> ORGANISM: Thosea asigna virus

<400> SEQUENCE: 41

Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 42
<211> LENGTH: 4104
<212> TYPE: DNA
<213> ORGANISM: Streptococcus pyogenes

<400> SEQUENCE: 42

| | |
|---|---|
| atggacaaga aatactcaat tggtcttgat atcggaacaa acagcgttgg atgggcggtt | 60 |
| attaccgacg aatataaagt tccttcgaag aaatttaaag tgcttggaaa cacggaccgg | 120 |
| cactcaatca agaagaatct gattggagct ttgctgtttg attctggtga gactgcggaa | 180 |
| gcaacacggc tgaagcgcac cgcacggcgc cgctacacgc ggcggaaaaa cagaatttgc | 240 |
| tacctccaag agattttag caacgaaatg gctaaagtgg acgattcttt tttccacaga | 300 |
| cttgaggaat ctttcctcgt cgaagaggat aaaaagcacg agcgccatcc tatttttggt | 360 |
| aatatagtgg atgaagttgc gtaccatgag aaatatccta cgatttacca cctcaggaag | 420 |
| aagctcgtgg attctacgga caaagcagac cttcggctca tttatttggc cctcgcacac | 480 |
| atgattaagt tcagaggtca tttttcttatc gagggggacc ttaatcccga taactccgac | 540 |
| gtcgataagc ttttcatcca gctcgtccaa acctataatc aattgtttga ggagaaccct | 600 |
| ataaatgcgt caggagtgga cgcaaaagcc atcttgagcg ctagactctc caaatctcgg | 660 |
| aggctcgaga atctgatcgc acagcttcct ggtgaaaaga gaatggact ctttggtaac | 720 |
| ttgattgcgc tctcactcgg tctgacaccc aatttcaaga caatttcga ccttgctgaa | 780 |
| gatgccaagt tgcaactctc taaagatacc tacgacgacg accttgacaa tctgttggca | 840 |
| caaataggg accagtacgc cgatctttc cttgctgcca aaaatttgtc tgacgctatt | 900 |
| ttgttgtccg atattctgcg cgtgaatacg gagatcacta agcccctct ttccgctagc | 960 |
| atgattaagc ggtacgacga gcaccatcaa gaccttacgc tcctgaaagc tctcgtcagg | 1020 |
| caacagctcc cagaaaagta caaagaaata ttcttcgatc agagcaagaa cgggtatgca | 1080 |
| ggatacattg atgggggagc atcccaagag gagttctata agttcatcaa gccgatattg | 1140 |
| gagaaaatgg atggaactga agaactgctt gtcaagttga atcgcgaaga tcttttgagg | 1200 |
| aaacagagga cttttgataa tgggtccatc ccgcaccaaa ttcatttggg agagttgcat | 1260 |
| gcaatcttga agacagga ggattttac ccatttctga agacaacag agaaagata | 1320 |
| gagaaaatat tgactttccg catcccgtat tatgtcggtc cactggcgag gggcaatagc | 1380 |
| cgctttgcgt ggatgacgag gaaaagcgag gagaccataa cccctggaa cttcgaggaa | 1440 |
| gttgtggata gggtgcatc cgcacagtcg ttcattgaaa ggatgaccaa cttcgataag | 1500 |
| aaccttccta tgagaaagt ccttcctaaa cactccctgc tgtatgagta ctttaccgtg | 1560 |
| tacaacgagc tcacgaaagt gaaatatgtc acagagggga tgcgcaagcc agccttcctt | 1620 |
| tctggtgaac aaaaaaggc gatagtcgac ttgctcttta aaactaatag aaggtgaca | 1680 |
| gtcaaacagc tcaaagaaga ttatttaaa aaatagaat gctttgatag cgttgaaatc | 1740 |
| tccggtgtcg aggatcggtt taatgcgtct ctgggaacat accacgatct tcttaaaatc | 1800 |
| attaaagata agacttcct tgacaatgaa gaaacgaag acatattgga ggatatagtc | 1860 |
| ctgacccta ccctcttcga ggacaggaa atgatagagg agagacttaa aacgtatgct | 1920 |
| catctgtttg atgacaaggt tatgaaacag cttaaacgga ggcgctacac aggatggggg | 1980 |
| agactctcca gaaaattgat aaatgggatc cgcgataagc agtctggaaa gaccatcctc | 2040 |
| gacttcttga aaagcgatgg attcgcaaat cggaatttta tgcaactcat ccatgatgac | 2100 |
| agcctgacgt tcaaggaaga tattcaaaag gcacaagtta gcgggcaagg tgactctttg | 2160 |

```
catgaacata tagcgaacct tgcaggttcc cccgcgatca aaagggaat actccaaacg    2220 gtgaaagtcg tcgatgaact ggttaaagtg atgggacgcc ataagcccga gaatatagtc    2280
atcgaaatgg cgagagaaaa tcaaaccacg caaaagggcc agaaaaactc cagggagcgg    2340
atgaagagaa tagaggaagg catcaaggag ctcgggtctc agatcctcaa agaacatccg    2400
gtggagaata cgcagttgca aaacgagaag ctctaccttt actacctgca aaatgggaga    2460
gatatgtacg ttgaccagga attggatatt aacaggcttt ccgactatga cgtcgaccac    2520
atcgttccgc agtcgttctt gaaggacgac tctatagata taaggttct gacacgcagc    2580 gacaaaaacc ggggaaagtc agacaatgtc cccagcgaag aagttgttaa gaaaatgaaa    2640
aactattggc ggcagctcct taatgctaaa ttgattaccc aacgcaagtt cgataacctt    2700
acgaaggccg aacgcggcgg cttgtccgaa ctggacaagg cgggattcat caaacggcaa    2760
cttgtggaaa cccggcagat cacaaaacac gtggcacaaa tccttgattc taggatgaat    2820
accaaatatg atgagaatga taactgata cgcgaagtga agtgattac tttgaagagc    2880 aaactcgtgt cagatttccg gaaagatttt cagttttata agtcagaga gataaataac    2940 taccatcatg cacatgatgc atatctgaac gccgtcgtgg aacagctct tataaagaag    3000 taccccaaac tggaatctga gttcgtctac ggagattaca agtttacga tgtcagaaag    3060 atgatagcaa atcagagca agaaataggt aaggctactg ctaagtattt cttttactct    3120
aacattatga atttcttcaa gaccgaaatt accctggcca acggtgagat aagaaagcgc    3180
cccctcattg aaactaacgg cgaaacaggc gagatcgtgt gggataaagg tagagatttc    3240
gccacagttc ggaaagtgct cagcatgcct caggtgaaca tagttaaaaa gactgaggtt    3300
cagacaggcg gattctccaa agaatcaata cttcctaaga ggaactcaga taaactgatt    3360
gcaagaaaaa aagactggga tccaaagaaa tatggcggtt ttgactcccc cacagtcgcg    3420
tactcagtcc tggtcgtggc caaggtcgag aaggggaagt ccaaaaagct caagtcagtg    3480
aaggagctcc tgggcattac gatcatggaa aggtcatctt ttgaaaagaa cccaattgat    3540
ttccttgaag ccaaggggta taggaggtt aaaaaggacc tgatcatcaa gcttccgaaa    3600
tattcactgt ttgagctcga aaatggccgc aagaggatgt tggcctctgc tggcgaactt    3660
caaaaaggca acgagcttgc tctcccctcg aagtatgtga atttctgta tctggcctcg    3720 cactatgaga aattgaaagg atctccggaa gataacgaac aaaagcagct tttcgtcgag    3780
caacataagc actacctcga tgaaataata gaacagatct cagagtttag caagagggtc    3840
atactggccg atgcgaatct tgataaggtt ctctctgctt ataacaaaca tagggacaag    3900
cctatacggg agcaagccga gaacattatt catctcttta ccctcactaa tctcggtgcg    3960
cctgcggctt tcaagtattt tgacactacg atagacagaa aacgctatac ttcgaccaag    4020
gaagtcctgg acgcaaccct tattcaccag agcattacgg gactttatga gacgagaatc    4080
gatttgtctc aactcggtgg tgat                                           4104
```

<210> SEQ ID NO 43
<211> LENGTH: 1368
<212> TYPE: PRT
<213> ORGANISM: Streptococcus pyogenes

<400> SEQUENCE: 43

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30
```

```
Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                    100                 105                 110

His Glu Arg His Pro Ile Phe Gly Asn Ile Val Asp Glu Val Ala Tyr
                    115                 120                 125

His Glu Lys Tyr Pro Thr Ile Tyr His Leu Arg Lys Lys Leu Val Asp
                    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                    165                 170                 175

Asp Asn Ser Asp Val Asp Lys Leu Phe Ile Gln Leu Val Gln Thr Tyr
                    180                 185                 190

Asn Gln Leu Phe Glu Glu Asn Pro Ile Asn Ala Ser Gly Val Asp Ala
                    195                 200                 205

Lys Ala Ile Leu Ser Ala Arg Leu Ser Lys Ser Arg Arg Leu Glu Asn
                    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                    260                 265                 270

Asp Asp Leu Asp Asn Leu Leu Ala Gln Ile Gly Asp Gln Tyr Ala Asp
                    275                 280                 285

Leu Phe Leu Ala Ala Lys Asn Leu Ser Asp Ala Ile Leu Leu Ser Asp
                    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                    340                 345                 350

Asp Gln Ser Lys Asn Gly Tyr Ala Gly Tyr Ile Asp Gly Gly Ala Ser
                    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445
```

```
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
```

-continued

```
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
```

| | | | | | | | | | | | |
|---|---|---|---|---|---|---|---|---|---|---|---|
| Arg | Val | Ile | Leu | Ala | Asp | Ala | Asn | Leu | Asp | Lys | Val | Leu | Ser | Ala |
| | 1280 | | | | 1285 | | | | 1290 | | |

| | | | | | | | | | | | |
|---|---|---|---|---|---|---|---|---|---|---|---|
| Tyr | Asn | Lys | His | Arg | Asp | Lys | Pro | Ile | Arg | Glu | Gln | Ala | Glu | Asn |
| | 1295 | | | | 1300 | | | | 1305 | | |

| | | | | | | | | | | | |
|---|---|---|---|---|---|---|---|---|---|---|---|
| Ile | Ile | His | Leu | Phe | Thr | Leu | Thr | Asn | Leu | Gly | Ala | Pro | Ala | Ala |
| | 1310 | | | | 1315 | | | | 1320 | | |

| | | | | | | | | | | | |
|---|---|---|---|---|---|---|---|---|---|---|---|
| Phe | Lys | Tyr | Phe | Asp | Thr | Thr | Ile | Asp | Arg | Lys | Arg | Tyr | Thr | Ser |
| | 1325 | | | | 1330 | | | | 1335 | | |

| | | | | | | | | | | | |
|---|---|---|---|---|---|---|---|---|---|---|---|
| Thr | Lys | Glu | Val | Leu | Asp | Ala | Thr | Leu | Ile | His | Gln | Ser | Ile | Thr |
| | 1340 | | | | 1345 | | | | 1350 | | |

| | | | | | | | | | | | |
|---|---|---|---|---|---|---|---|---|---|---|---|
| Gly | Leu | Tyr | Glu | Thr | Arg | Ile | Asp | Leu | Ser | Gln | Leu | Gly | Gly | Asp |
| | 1355 | | | | 1360 | | | | 1365 | | |

<210> SEQ ID NO 44
<211> LENGTH: 3921
<212> TYPE: DNA
<213> ORGANISM: Acidaminococcus

<400> SEQUENCE: 44

```
atgactcagt tcgaaggttt caccaacctg taccaagtgt ccaaaacgtt gaggttcgag      60
ctgattccac aggggaaaac gctcaagcat atccaagaac agggcttcat tgaggaagat     120
aaagctcgca acgatcacta caaggagctt aagcctatta ttgacaggat ctacaaaacc     180
tacgctgatc aatgcctcca actggttcag ctggattggg agaatctctc cgccgcgatc     240
gattcctacc ggaaggagaa gacggaagaa cacgcaacg ctcttataga agaacaggcg      300
acgtatcgca atgctattca cgactatttt ataggacgga ctgataatct cacggacgca     360
atcaataaaa ggcatgcaga gatctacaaa ggtctcttta agctgaatt gtttaacgga     420
aaagttctca acaactggg tacagtgact acgacggaaac acgagaatgc gctgctgaga     480
tccttcgata gttcactac ctatttctcg ggcttttacg agaacaggaa gaatgtgttc      540
tccgctgagg atatcagcac agctatacct caccggatcg tgcaagacaa tttcccaaag     600
ttcaaagaaa actgtcacat attcacaagg ctcattaccg ctgtccccag cctgagggaa     660
catttcgaga cgttaaaaa agccattgga atcttcgtct cgacgagcat agaggaggtt     720
ttctctttc ccttttacaa tcaacttctg acccaaacac aaattgattt gtacaaccaa     780
ttgttgggag gcatatcgag ggaggcgggg actgagaaaa ttaagggcct taacgaagtc     840
ctgaaccttg cgattcaaaa gaatgacgaa acggcgcata ttatagcttc acttcctcat     900
cgcttcatcc cacttttcaa acaaatcctc tccgaccgga tacacttag cttcatactg     960
gaggagttta atcggacga ggaagtcata cagtcctttt gcaagtataa aacgttgctc    1020
cggaatgaaa atgtcctgga aacggctgag gcgctcttta tgagctgaa ctcaattgac    1080
ttgacccaca tctttatctc gcataaaaaa ttggaaacta tctcttcagc gctgtgtgat    1140
cattgggaca ccctcaggaa cgcattgtat gaaggagaa tttcagaact acgggcaag    1200
atcaccaaat cagcgaagga aaaagtgcag cggagcttga agcatgaaga cataaatctt    1260
caagagatta tatctgcagc aggcaaagaa ctgtccgagg cttttaagca gaagacatcc    1320
gaaattcttt ctcacgcgca cgcggcattg gaccaacccc tcccaaccac tttgaagaag    1380
caggaggaaa aggagattct gaagtcacag cttgattcgc ttctgggct ctaccatctg    1440
ttggattggt ttgctgtgga cgaatccaat gaagtcgacc ccgaattctc agcgaggctc    1500
accggaataa aactggagat ggaaccgtcc ttgtctttct acaataaagc caggaattac    1560
```

```
gccacgaaga agccatactc agtggagaaa tttaaactga acttccaaat gcctactctg      1620
gcttcaggtt gggatgtcaa caaggagaaa acaacggag caatcctttt tgtcaagaac       1680
ggtctctatt acctcggaat tatgccgaaa cagaagggtc gctataaagc actgagcttt      1740
gaacccacgg agaaaacgtc cgagggcttc gacaagatgt attatgacta tttccccgac      1800
gccgcgaaaa tgattccgaa atgcagcact caactcaagg ccgtgacagc ccactttcag      1860
actcacacaa ctccaatact tttgtcgaat aattttattg agcctctcga ataactaaa       1920 gagatatatg accttaataa tccagagaaa gaaccaaaaa aattccaaac tgcctacgct      1980
aagaagactg gtgatcagaa gggctacaga gaggcgttgt gtaaatggat cgacttcact      2040
agggactttc tgtcaaagta cactaaaaca acttctatag atctgagctc cctccgccca      2100
tcatctcagt acaaggatct tggtgaatac tatgccgagc tcaacccact cctctaccat      2160
atcagcttcc agcgcatagc tgaaaaagaa ataatggatg ctgttgaaac aggcaaactg      2220
tatctctttc agatctacaa caaggatttt gctaaagggc atcacgggaa gcctaacctt      2280
cacacattgt actggaccgg cctctttttca ccagagaatt tggcaaaaac ttcgattaaa     2340
ctcaacgggc aagcagagct tttctaccgg cccaagtccc gcatgaaacg catggcacac      2400
aggctgggag aaaagatgct gaacaagaaa ttgaaggacc agaagacacc aataccagat      2460
actctgtatc aggagctcta cgactatgtt aaccataggc tctctcacga cctctctgac      2520
gaagccaggg cacttctgcc caatgtgatc acgaaggagg tgtctcacga gataattaag      2580
gacagacggt tcacgtcgga caagttttt ttccatgtcc cgattacgct gaactaccaa       2640
gctgccaact ctccatcaaa atttaatcag agggttaatg cgtatttgaa ggaacatcct      2700
gagactccaa tcataggtat agatcggggc gagaggaacc ttatttacat aaccgttatt     2760
gattccacgg gcaaaattct ggagcagcgg tcgctgaata cgatacaaca atttgattat      2820
caaaagaagc ttgacaatcg cgagaaagaa agggtcgccg caagacaggc gtggagcgtc      2880
gtcggtacta taaaggatct taaacaaggt tatttgtcac aagttataca tgaaatagtt      2940
gaccttatga tacactatca ggctgtcgtt gtccttgaaa acctcaactt tgggtttaag      3000
agcaagcgga caggaattgc agagaaggcc gtgtatcagc agttcgaaaa gatgcttatt      3060
gataagctca actgcctggt gcttaaagac tacccagcag agaaagttgg cggtgttctg      3120
aatccttacc agctcacaga ccagtttact tcctttgcaa aaatgggcac ccagtcgggt      3180
ttcctctttt atgttcctgc accgtatacg tctaagatag atcctctgac aggctttgtg      3240
gacccctttg tttggaaaac tatcaaaaat catgaatcga ggaaacactt cctcgagggt      3300
ttcgattttc tccactatga tgtgaagact ggcgacttta tacttcattt taaaatgaac      3360
cgcaatcttt cgtttcaacg cggacttcca ggatttatgc cggcctggga tatcgttttc      3420
gaaaagaatg agacgcaatt tgacgctaag ggaacgcctt tcatcgcggg gaaacggatt      3480
gtcccggtca tagaaaatca tagatttacg ggtcggtaca gggacctgta tcccgcgaac      3540
gaactcatcg cgcttctcga agagaaaggt atagtgtttc gcgatggatc aaacatcttg      3600
cctaaactcc tggaaaacga cgattcacac gctatagaca cgatggtggc actgatccgc      3660
tcggtgctgc agatgcggaa ttcaaacgct gcgactgggg aagactatat aaactcacca      3720
gtgagagatt tgaacggcgt ttgctttgat tcgcggttcc aaaatcccga atggcccatg      3780
gacgctgatg ccaatggagc gtatcacatt gcgcttaagg gtcagttgct tctgaaccac      3840
ttgaaagaat ctaaagatct taagcttcaa aacggtattt caaaccaaga ctggctcgcc      3900
tatatacagg aactccgcaa c                                                3921
```

<210> SEQ ID NO 45
<211> LENGTH: 1307
<212> TYPE: PRT
<213> ORGANISM: Acidaminococcus

<400> SEQUENCE: 45

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
```

```
              370             375             380
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
        610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
        690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800
```

```
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
                820                 825                 830
Arg Leu Ser His Asp Leu Ser Asp Glu Ala Arg Ala Leu Leu Pro Asn
                835                 840                 845
Val Ile Thr Lys Glu Val Ser His Glu Ile Ile Lys Asp Arg Arg Phe
                850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
                900                 905                 910
Asn Leu Ile Tyr Ile Thr Val Ile Asp Ser Thr Gly Lys Ile Leu Glu
                915                 920                 925
Gln Arg Ser Leu Asn Thr Ile Gln Gln Phe Asp Tyr Gln Lys Lys Leu
                930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
                980                 985                 990
Glu Asn Leu Asn Phe Gly Phe Lys Ser Lys Arg Thr Gly Ile Ala Glu
                995                 1000                1005
Lys Ala Val Tyr Gln Gln Phe Glu Lys Met Leu Ile Asp Lys Leu
                1010                1015                1020
Asn Cys Leu Val Leu Lys Asp Tyr Pro Ala Glu Lys Val Gly Gly
                1025                1030                1035
Val Leu Asn Pro Tyr Gln Leu Thr Asp Gln Phe Thr Ser Phe Ala
                1040                1045                1050
Lys Met Gly Thr Gln Ser Gly Phe Leu Phe Tyr Val Pro Ala Pro
                1055                1060                1065
Tyr Thr Ser Lys Ile Asp Pro Leu Thr Gly Phe Val Asp Pro Phe
                1070                1075                1080
Val Trp Lys Thr Ile Lys Asn His Glu Ser Arg Lys His Phe Leu
                1085                1090                1095
Glu Gly Phe Asp Phe Leu His Tyr Asp Val Lys Thr Gly Asp Phe
                1100                1105                1110
Ile Leu His Phe Lys Met Asn Arg Asn Leu Ser Phe Gln Arg Gly
                1115                1120                1125
Leu Pro Gly Phe Met Pro Ala Trp Asp Ile Val Phe Glu Lys Asn
                1130                1135                1140
Glu Thr Gln Phe Asp Ala Lys Gly Thr Pro Phe Ile Ala Gly Lys
                1145                1150                1155
Arg Ile Val Pro Val Ile Glu Asn His Arg Phe Thr Gly Arg Tyr
                1160                1165                1170
Arg Asp Leu Tyr Pro Ala Asn Glu Leu Ile Ala Leu Leu Glu Glu
                1175                1180                1185
Lys Gly Ile Val Phe Arg Asp Gly Ser Asn Ile Leu Pro Lys Leu
                1190                1195                1200
```

| Leu | Glu | Asn | Asp | Asp | Ser | His | Ala | Ile | Asp | Thr | Met | Val | Ala | Leu |
|-----|-----|-----|-----|-----|-----|-----|-----|-----|-----|-----|-----|-----|-----|-----|
| 1205 | | | | | 1210 | | | | | 1215 | | | | |
| Ile | Arg | Ser | Val | Leu | Gln | Met | Arg | Asn | Ser | Asn | Ala | Ala | Thr | Gly |
| 1220 | | | | | 1225 | | | | | 1230 | | | | |
| Glu | Asp | Tyr | Ile | Asn | Ser | Pro | Val | Arg | Asp | Leu | Asn | Gly | Val | Cys |
| 1235 | | | | | 1240 | | | | | 1245 | | | | |
| Phe | Asp | Ser | Arg | Phe | Gln | Asn | Pro | Glu | Trp | Pro | Met | Asp | Ala | Asp |
| 1250 | | | | | 1255 | | | | | 1260 | | | | |
| Ala | Asn | Gly | Ala | Tyr | His | Ile | Ala | Leu | Lys | Gly | Gln | Leu | Leu | Leu |
| 1265 | | | | | 1270 | | | | | 1275 | | | | |
| Asn | His | Leu | Lys | Glu | Ser | Lys | Asp | Leu | Lys | Leu | Gln | Asn | Gly | Ile |
| 1280 | | | | | 1285 | | | | | 1290 | | | | |
| Ser | Asn | Gln | Asp | Trp | Leu | Ala | Tyr | Ile | Gln | Glu | Leu | Arg | Asn | |
| 1295 | | | | | 1300 | | | | | 1305 | | | | |

<210> SEQ ID NO 46
<211> LENGTH: 1002
<212> TYPE: DNA
<213> ORGANISM: Artificial Sequence
<220> FEATURE:
<223> OTHER INFORMATION: WUS-HISTAG-GZCPP coding sequence

<400> SEQUENCE: 46

```
gtgaggctcc ctcctcccgt gaggctccct cccctctcg tgagacccc tcccttgcat      60
catcatcatc atcatatggc ggctaacgca ggtggtgggg gcgcaggagg cggtagcgga    120
tcggggtcag tcgcggcacc cgcagtgtgc aggccatcag gttctcggtg gactccgact    180
ccggaacaga ttcgcatgct caaggagttg tattacgggt gcggaattag gtcaccatca    240
tctgagcaga ttcaaaggat aacagcaatg ttgcggcaac atggtaagat cgagggaaag    300
aatgtctttt actggttcca gaatcataaa gctcgcgagc gccagaaaag gcggttgacg    360
tccctcgacg tgaatgttcc cgcagcgggg gccgcagatg caaccacctc acagttgggt    420
gttctctcgt tgtcttctcc gccaccatcc ggcgcagcgc ccccgtcccc gactctcgga    480
ttctacgccg cgggaaatgg tgggggctcc gcagtgttgc tggacacatc ttctgactgg    540
ggaagctctg gggcggcgat ggccacagag acatgctttt tgcaggacta catgggcgtt    600
acagataccg gtcctcgtc gcagtggcca cggttttcct cctccgacac cataatggcg    660
gctgctgctg ccagggcagc gacaacaagg gctccggaga cacttcctct gttcccaacg    720
tgcggagatg acgtgggtc gggttcgtcc agctacctcc ctttctgggg cgcagcgagc    780
actaccgcgg gcgcaacgtc tagcgtcgcc atccaacaac aacatcaatt gcaggaacaa    840
tattcgttct attcaaactc aaattctacg caactggcag gcacagggaa tcaagacgtg    900
tcggctaccg ctgcagcggc agctgcactt gagttgtctc tcagctcatg gtgtagcccc    960
tatcctgcag ccgggtcgat ggggcatcat catcatcatc at                      1002
```

<210> SEQ ID NO 47
<211> LENGTH: 334
<212> TYPE: PRT
<213> ORGANISM: Artificial Sequence
<220> FEATURE:
<223> OTHER INFORMATION: WUS-HISTAG-GZCPP protein sequence

<400> SEQUENCE: 47

| Val | Arg | Leu | Pro | Pro | Pro | Val | Arg | Leu | Pro | Pro | Pro | Leu | Val | Arg | Pro |
|-----|-----|-----|-----|-----|-----|-----|-----|-----|-----|-----|-----|-----|-----|-----|-----|
| 1 | | | | 5 | | | | | 10 | | | | | 15 | |

| Pro | Pro | Leu | His | His | His | His | His | His | Met | Ala | Ala | Asn | Ala | Gly | Gly |

```
            20                  25                  30
Gly Gly Ala Gly Gly Ser Gly Ser Gly Val Ala Ala Pro Ala
            35                  40                  45

Val Cys Arg Pro Ser Gly Ser Arg Trp Thr Pro Thr Pro Glu Gln Ile
50                  55                  60

Arg Met Leu Lys Glu Leu Tyr Tyr Gly Cys Gly Ile Arg Ser Pro Ser
65                  70                  75                  80

Ser Glu Gln Ile Gln Arg Ile Thr Ala Met Leu Arg Gln His Gly Lys
                85                  90                  95

Ile Glu Gly Lys Asn Val Phe Tyr Trp Phe Gln Asn His Lys Ala Arg
            100                 105                 110

Glu Arg Gln Lys Arg Arg Leu Thr Ser Leu Asp Val Asn Val Pro Ala
        115                 120                 125

Ala Gly Ala Ala Asp Ala Thr Thr Ser Gln Leu Gly Val Leu Ser Leu
    130                 135                 140

Ser Ser Pro Pro Pro Ser Gly Ala Ala Pro Ser Pro Thr Leu Gly
145                 150                 155                 160

Phe Tyr Ala Ala Gly Asn Gly Gly Ser Ala Val Leu Leu Asp Thr
                165                 170                 175

Ser Ser Asp Trp Gly Ser Ser Gly Ala Ala Met Ala Thr Glu Thr Cys
            180                 185                 190

Phe Leu Gln Asp Tyr Met Gly Val Thr Asp Thr Gly Ser Ser Gln
        195                 200                 205

Trp Pro Arg Phe Ser Ser Ser Asp Thr Ile Met Ala Ala Ala Ala
    210                 215                 220

Arg Ala Ala Thr Thr Arg Ala Pro Glu Thr Leu Pro Leu Phe Pro Thr
225                 230                 235                 240

Cys Gly Asp Asp Gly Gly Ser Gly Ser Ser Ser Tyr Leu Pro Phe Trp
                245                 250                 255

Gly Ala Ala Ser Thr Thr Ala Gly Ala Thr Ser Ser Val Ala Ile Gln
            260                 265                 270

Gln Gln His Gln Leu Gln Glu Gln Tyr Ser Phe Tyr Ser Asn Ser Asn
        275                 280                 285

Ser Thr Gln Leu Ala Gly Thr Gly Asn Gln Asp Val Ser Ala Thr Ala
    290                 295                 300

Ala Ala Ala Ala Ala Leu Glu Leu Ser Leu Ser Ser Trp Cys Ser Pro
305                 310                 315                 320

Tyr Pro Ala Ala Gly Ser Met Gly His His His His His
                325                 330

<210> SEQ ID NO 48
<211> LENGTH: 1773
<212> TYPE: DNA
<213> ORGANISM: Artificial Sequence
<220> FEATURE:
<223> OTHER INFORMATION: WUS-GR coding sequence

<400> SEQUENCE: 48
atggctgcta acgccggcgg cggaggagcc ggaggcggaa gtggcagtgg ctcggttgcc      60
gcgcctgccg tatgtaggcc tagtggttcc agatggactc caacacctga gcagatacgc     120
atgctcaagg aactttacta cggttgtggt atccgctcgc cttctagtga acagattcaa     180
cgcataacag cgatgttgcg tcagcacggc aaaatcgaag caaaaacgt attttactgg     240 tttcaaaatc ataaagcccg cgagcgtcaa aagagggagc tcacgagttt ggacgtgaac     300
```

```
gtacctgctg ccggagctgc cgacgccacc acgtcccaac ttggagttct gagtcttagc    360
tccccgccgc cttccggagc cgccccaccg agtcccactc ttggatttta tgccgctgga    420
aatggaggag gttccgccgt gcttttggac acttcgtctg attggggttc cagcggcgct    480
gcaatggcga ctgagacttg tttccttcag gactatatgg gtgtcaccga tacgggaagt    540
tcatcacaat ggcccaggtt ttcaagtagt gacactataa tggctgcggc tgccgcgaga    600
gcagctacga ccagggcacc cgagacactg cctctcttcc aacttgcgg tgacgacggc     660
ggctccggtt cctcgagtta tttgcctttc tggggcgcgg cctccacaac agcaggcgcg    720
acaagttccg ttgcaatcca gcagcaacat caacttcagg agcagtatag ttttttactcc   780
aatagtaact ccacccaact cgcgggcacg ggcaaccaag acgtgagtgc gacagcagcg    840
gcagcagcgg ctttggagct gagtctgtct tcgtggtgct ctccctatcc agcggcaggt    900
tcaatgggag aagctcgcaa aactaaaaaa aaaataaagg gcattcaaca agctacggcc    960
ggagtgagcc aggacactag cgagaaccct aacaagacaa tcgtcccggc ggcacttccg   1020
caactcaccc ctacgctggt ctcgcttttg gaggttatag aacctgaagt gctctacgca   1080
ggctatgact cgagcgtccc tgattctgcg tggcggataa tgactacttt gaatatgctg   1140
gggggtcgca aggttattgc cgcagtgaaa tgggccaaag caatcttggg actccgcaat   1200
ctgcacctcg acgaccaaat gactctcctc caatatagct ggatgtttct gatggccttt   1260
gcgctgggtt ggcgcagcta taggcagtca tcaggtaacc tcttgtgttt cgccctgat    1320
ttgataatta cgaacagcg gatgtctctt ccctgtatgt atgaccagtg taaacatatg    1380
ttgtttgtgt catcagagct tcagagactt caggtgagct acgaagaata tctttgtatg   1440
aaaacacttc ttttgttgag cagcgtgcct aaggagggcc ttaagagcca ggaactcttc   1500
gatgaaatca gaatgactta tatcaaagaa cttggcaaag caattgtgaa acgggaagga   1560
aatagctcgc agaactggca acggttctac cagttgacga aactgttgga ttcgatgcac   1620
gaggtcgtcg aaaacttgct tacctactgt tttcaaacat tcctcgataa aaccatgagc   1680
atagagtttc cagagatgtt ggccgaaata attacaaacc agatacccaa atactcaaat   1740
ggcaatatta agaaacttct gtttcaccaa aaa                                1773
```

<210> SEQ ID NO 49
<211> LENGTH: 591
<212> TYPE: PRT
<213> ORGANISM: Artificial Sequence
<220> FEATURE:
<223> OTHER INFORMATION: WUS-GR protein sequence

<400> SEQUENCE: 49

```
Met Ala Asn Ala Gly Gly Gly Ala Gly Gly Gly Ser Gly Ser
 1               5                  10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
        50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
```

```
                100                 105                 110
Gln Leu Gly Val Leu Ser Leu Ser Pro Pro Ser Gly Ala Ala
            115                 120                 125
Pro Pro Ser Pro Thr Leu Gly Phe Tyr Ala Ala Gly Asn Gly Gly
            130                 135                 140
Ser Ala Val Leu Leu Asp Thr Ser Ser Asp Trp Gly Ser Ser Gly Ala
145                 150                 155                 160
Ala Met Ala Thr Glu Thr Cys Phe Leu Gln Asp Tyr Met Gly Val Thr
                165                 170                 175
Asp Thr Gly Ser Ser Ser Gln Trp Pro Arg Phe Ser Ser Ser Asp Thr
                180                 185                 190
Ile Met Ala Ala Ala Ala Arg Ala Ala Thr Thr Arg Ala Pro Glu
                195                 200                 205
Thr Leu Pro Leu Phe Pro Thr Cys Gly Asp Asp Gly Gly Ser Gly Ser
            210                 215                 220
Ser Ser Tyr Leu Pro Phe Trp Gly Ala Ala Ser Thr Thr Ala Gly Ala
225                 230                 235                 240
Thr Ser Ser Val Ala Ile Gln Gln His Gln Leu Gln Glu Gln Tyr
                245                 250                 255
Ser Phe Tyr Ser Asn Ser Asn Ser Thr Gln Leu Ala Gly Thr Gly Asn
                260                 265                 270
Gln Asp Val Ser Ala Thr Ala Ala Ala Ala Ala Leu Glu Leu Ser
                275                 280                 285
Leu Ser Ser Trp Cys Ser Pro Tyr Pro Ala Ala Gly Ser Met Gly Glu
            290                 295                 300
Ala Arg Lys Thr Lys Lys Ile Lys Gly Ile Gln Gln Ala Thr Ala
305                 310                 315                 320
Gly Val Ser Gln Asp Thr Ser Glu Asn Pro Asn Lys Thr Ile Val Pro
                325                 330                 335
Ala Ala Leu Pro Gln Leu Thr Pro Thr Leu Val Ser Leu Leu Glu Val
                340                 345                 350
Ile Glu Pro Glu Val Leu Tyr Ala Gly Tyr Asp Ser Ser Val Pro Asp
                355                 360                 365
Ser Ala Trp Arg Ile Met Thr Thr Leu Asn Met Leu Gly Gly Arg Gln
                370                 375                 380
Val Ile Ala Ala Val Lys Trp Ala Lys Ala Ile Leu Gly Leu Arg Asn
385                 390                 395                 400
Leu His Leu Asp Asp Gln Met Thr Leu Leu Gln Tyr Ser Trp Met Phe
                405                 410                 415
Leu Met Ala Phe Ala Leu Gly Trp Arg Ser Tyr Arg Gln Ser Ser Gly
                420                 425                 430
Asn Leu Leu Cys Phe Ala Pro Asp Leu Ile Ile Asn Glu Gln Arg Met
                435                 440                 445
Ser Leu Pro Cys Met Tyr Asp Gln Cys Lys His Met Leu Phe Val Ser
            450                 455                 460
Ser Glu Leu Gln Arg Leu Gln Val Ser Tyr Glu Glu Tyr Leu Cys Met
465                 470                 475                 480
Lys Thr Leu Leu Leu Leu Ser Ser Val Pro Lys Glu Gly Leu Lys Ser
                485                 490                 495
Gln Glu Leu Phe Asp Glu Ile Arg Met Thr Tyr Ile Lys Glu Leu Gly
                500                 505                 510
Lys Ala Ile Val Lys Arg Glu Gly Asn Ser Ser Gln Asn Trp Gln Arg
                515                 520                 525
```

```
Phe Tyr Gln Leu Thr Lys Leu Leu Asp Ser Met His Glu Val Val Glu
            530             535             540

Asn Leu Leu Thr Tyr Cys Phe Gln Thr Phe Leu Asp Lys Thr Met Ser
545             550             555             560

Ile Glu Phe Pro Glu Met Leu Ala Glu Ile Ile Thr Asn Gln Ile Pro
                565             570             575

Lys Tyr Ser Asn Gly Asn Ile Lys Lys Leu Leu Phe His Gln Lys
            580             585             590
```